(12) United States Patent
Wang et al.

(10) Patent No.: US 12,072,403 B2
(45) Date of Patent: Aug. 27, 2024

(54) SYSTEM AND METHOD OF PERCEPTIVE QUANTITATIVE MAPPING OF PHYSICAL PROPERTIES

(71) Applicant: Cornell University, Ithaca, NY (US)

(72) Inventors: Yi Wang, New York, NY (US); Zhe Liu, New York, NY (US); Jinwei Zhang, New York, NY (US); Qihao Zhang, New York, NY (US); Junghun Cho, New York, NY (US); Pascal Spincemaille, New York, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 18/474,048

(22) Filed: Sep. 25, 2023

(65) Prior Publication Data

US 2024/0012080 A1    Jan. 11, 2024

Related U.S. Application Data

(63) Continuation of application No. 17/614,277, filed as application No. PCT/IB2020/055079 on May 28, 2020, now Pat. No. 11,782,112.
(Continued)

(51) Int. Cl.
G01R 33/56       (2006.01)
A61B 5/00        (2006.01)
(Continued)

(52) U.S. Cl.
CPC ........ *G01R 33/5608* (2013.01); *A61B 5/0042* (2013.01); *A61B 5/055* (2013.01);
(Continued)

(58) Field of Classification Search
None
See application file for complete search history.

(56) References Cited

U.S. PATENT DOCUMENTS 7,069,068 B1 *   6/2006   Ostergaard ............. A61B 6/507
                                                600/407
10,890,641 B2    1/2021   Wang et al.
(Continued)

OTHER PUBLICATIONS

Zhang, J., et al., "Fidelity Imposed Network Edit (FINE) for Solving Ill-Posed Image Reconstruction," May 17, 2019, retrieved from: https://arxiv.org/pdf/1905.07284.
(Continued)

*Primary Examiner* — Rodney E Fuller
(74) *Attorney, Agent, or Firm* — Leydig, Voit & Mayer, Ltd.

(57) ABSTRACT

Exemplary methods for quantitative mapping of physical properties, systems and computer-accessible medium can be provided to generate images of tissue magnetic susceptibility, transport parameters and oxygen consumption from magnetic resonance imaging data using the Bayesian inference approach, which minimizes a data fidelity term under a constraint of a structure prior knowledge. The data fidelity term is constructed directly from the magnetic resonance imaging data. The structure prior knowledge can be characterized from known anatomic images using image feature extraction operation or artificial neural network. Thus, according to the exemplary embodiment, system, method and computer-accessible medium can be provided for determining physical properties associated with at least one structure.

19 Claims, 38 Drawing Sheets

Related U.S. Application Data

(60) Provisional application No. 62/853,290, filed on May 28, 2019.

(51) Int. Cl.
*A61B 5/055* (2006.01)
*G01R 33/565* (2006.01)
*G06T 7/00* (2017.01)

(52) U.S. Cl.
CPC .......... *A61B 5/7221* (2013.01); *A61B 5/7267* (2013.01); *G01R 33/56536* (2013.01); *G06T 7/0012* (2013.01); *G06T 2207/10088* (2013.01); *G06T 2207/20081* (2013.01); *G06T 2207/20084* (2013.01)

(56) References Cited

U.S. PATENT DOCUMENTS

| | | |
|---|---|---|
| 2015/0145515 A1 | 5/2015 | Liu et al. |
| 2017/0059682 A1 | 3/2017 | Dagher et al. |
| 2018/0321347 A1 | 11/2018 | Wang et al. |
| 2019/0204401 A1 | 7/2019 | O'Brien et al. |
| 2019/0246938 A1 | 8/2019 | Gharagouzloo et al. |
| 2023/0320611 A1* | 10/2023 | Wang .................... G16H 50/70 382/128 |

OTHER PUBLICATIONS

Cho, J., et al., "Cerebral metabolic rate of oxygen (CMRO2) mapping by combining quantitative susceptibility mapping (QSM) and quantitative blood oxygenation level-dependent imaging (qBOLD)," Magnetic Resonance in Medicine, vol. 80, No. 4, Mar. 7, 2018, pp. 1595-1604.

Liu, Z., et al., "Preconditioned total field inversion (TFI) method for quantitative susceptibility mapping: QSM Using Preconditioned Total Field Inversion," Magnetic Resonance in Medicine, vol. 78, No. 1, Jul. 28, 2016, pp. 303-315.

International Search Report in International Patent Application No. PCT/IB2020/055079 dated Oct. 28, 2020.

* cited by examiner e)

f)

g)

h)

a)

|      | Fidelity | SSIM |
|------|----------|------|
| MEDI | 5.83     | 0.98 |
| DL   | 6.47     | 0.97 |
| DLL2 | 5.17     | 0.98 |
| FINE | 4.71 | 0.98 | b)

|         |      | Fidelity    | SSIM          |
|---------|------|-------------|---------------|
| T2w     | DTV  | 249 ± 45    | 0.97 ± 0.01   |
|         | DL   | 1987 ± 560  | 0.93 ± 0.03   |
|         | DLL2 | 211 ± 46    | 0.96 ± 0.02   |
|         | FINE | 191 ± 57| 0.98 ± 0.01 |
| T2FLAIR | DTV  | 285 ± 64    | 0.97 ± 0.01   |
|         | DL   | 2740 ± 1002 | 0.93 ± 0.03   |
|         | DLL2 | 266 ± 79    | 0.97 ± 0.01   |
|         | FINE | 196 ± 76| 0.98 ± 0.01 |

SYSTEM AND METHOD OF PERCEPTIVE QUANTITATIVE MAPPING OF PHYSICAL PROPERTIES

CROSS-REFERENCE TO RELATED APPLICATIONS

This patent application is a continuation of copending U.S. patent application Ser. No. 17/614,277, filed Nov. 24, 2021, which is national stage entry of International Patent Application No. PCT/IB2020/055079, filed May 28, 2020, which claims the benefit of U.S. Provisional Patent Application No. 62/853,290, filed May 28, 2019. The aforementioned patent applications are incorporated by reference herein in their entireties.

STATEMENT REGARDING FEDERALLY SPONSORED RESEARCH AND DEVELOPMENT

"This invention was made with government support under Grant No. R01 CA181566, DK116126, NS072370, NS090464, NS095562, NS105144 and R21EB024366 awarded by the National Institutes of Health. The government has certain rights in this invention." This statement is included solely to comply with 37 C.P.R. § 401.14(f)(4) and should not be taken as an assertion or admission that the application discloses and/or claims only one invention.

TECHNICAL FIELD

This invention relates to magnetic resonance imaging, and more particularly to quantitatively mapping material intrinsic physical properties using signals collected in magnetic resonance imaging.

BACKGROUND

Quantitative susceptibility mapping (QSM) in magnetic resonance imaging (MRI) has received increasing clinical and scientific interest. QSM has shown promise in characterizing and quantifying chemical compositions such as iron, calcium, and contrast agents including gadolinium and superparamagnetic iron oxide nanoparticles. Tissue composition of these compounds may be altered in various neurological disorders, such as Parkinson's disease, Alzheimer's disease, stroke, multiple sclerosis, hemochromatosis, and tumor as well as other disease throughout the body. Deoxyheme iron reflects tissue metabolic oxygen extraction from circulation. QSM is able to unravel novel information related to the magnetic susceptibility (or simply referred as susceptibility), a physical property of underlying tissue. Due to the prevalence of iron and calcium in living organisms, their active involvement in vital cellular functions, their important roles in the musculoskeletal system, QSM is in general very useful to study the molecular biology of iron/calcium by tracking iron in the circulation system and the metabolic activities by using iron and calcium as surrogate marks. QSM can also be used to quantify contrast agents. Contrast agent passage in tissue can be captured in time resolved imaging, which can be fitted to physical transport equations for generating quantitative maps of transport parameters. Therefore, accurate mapping of the magnetic susceptibility induced by iron, calcium and contrast agents will provide tremendous benefit to clinical researchers to probe the structure and functions of human body, and to clinicians to better diagnose various diseases and provide relevant treatment.

SUMMARY

Implementations of systems and methods for collecting and processing MRI signals of a subject, reconstructing maps of physical properties intrinsic to the subject (e.g., magnetic susceptibility, transport parameters, and deoxyheme concentration), and reconstructing multiple contrast images are described below. In some implementations, MR signal data corresponding to a subject can be transformed into multiecho or time resolved images that quantitatively depict the structure and/or composition and/or function of the subject. Using this quantitative susceptibility or transport map, one or more susceptibility- or transport-based images of the subject can be generated and displayed to a user. The user can then use these images for diagnostic or therapeutic purposes, for example to investigate the structure and/or composition and/or function of the subject, and/or to diagnose and/or treat various conditions or diseases based, at least in part, on the images. As one or more of the described implementations can result in susceptibility and/or transport-based images having higher quality and/or accuracy compared to other susceptibility and/or transport mapping techniques, at least some of these implementations can be used to improve a user's understanding of a subject's structure and/or composition and/or function, and can be used to improve the accuracy of any resulting medical diagnoses or therapeutic analyses.

Some of the implementations described below can be used to perform the magnetic dipole inversion from multi-echo images while allowing incorporation of preconditioning and artificial neural network to improve susceptibility mapping quality, accuracy and speed. Some of the implementations can be used to accelerate imaging of various tissue contrasts through reconstructing images from undersampled data while allowing incorporation numerical optimization or artificial neural network to impose structural consistency. Some of the implementations can be used to extract physical parameters including velocity, diffusion and pressure gradient from time resolved images. Some of the implementations can be used to map tissue oxygen extraction fraction from echo-time resolved magnitude and phase images.

In general, one aspect of the invention disclosed here improves the accuracy and speed in reconstructing magnetic susceptibility distribution by using an adaptive preconditioner that is estimated from R2*, the magnitude decay rate. This aspect of invention solves the practical problem of automatically determining preconditioner in QSM reconstruction.

In general, another aspect of the invention disclosed here improves the accuracy in deep learning (DL) solutions of image reconstruction from noisy incomplete data, including ill-posed inverse problems of quantitative susceptibility mapping, quantitative tissue mapping, and multiple contrast image reconstruction by updating DL network or DL output with testing data. This aspect of invention improves fidelity of DL network, also referred to as artificial neural network, to the testing data. Substantial errors in DL reconstruction are reduced by updating the trained DL network weights according to the testing data.

In general, another aspect of the invention disclosed here enables extraction of transport parameters including velocity, diffusion and pressure gradient from time resolved image data that capture contrast agent passages in tissue by solving the inverse problem of fitting image data to the transport equations. This aspect of invention enables automated post-processing of time resolved imaging of contrast agent passages in tissue and eliminates both the manual selection and the inherent error of arterial input function used in prior art.

In general, another aspect of the invention disclosed here enables extraction of tissue oxygen extraction fraction from echo-time resolved (multiecho) magnitude and phase images, including complex data acquired in a multiecho gradient echo sequence. This aspect of invention enables robust OEF estimation from multiecho complex image data without using vascular challenges.

Implementations of these aspects may include one or more of the following features.

In some implementations, the cerebrospinal fluid in the ventricles in the brain is segmented based on low R2* values by applying R2* thresholding and connectivity.

In some implementations, the preconditioner is automatically determined from tissue R2* values.

In some implementations, the prior information regarding the magnetic susceptibility distribution is determined based on structural information of the object estimated from acquired images of the object.

In some implementations, the transport parameter is velocity of convection or drift of blood flowing through tissue.

In some implementations, the optimization is realized using quasi-Newton, alternating direction method of multipliers, or deep learning of artificial neural network.

In some implementations, the artificial neural network includes a U-Net structure with each of its convolutional blocks consisting of a 3D convolution layer, a ReLU activation and a Batch Normalization layer.

In some implementations, the object comprises a cortex, a putamen, a globus pallidus, a red nucleus, a substantia nigra, or a subthalamic nucleus of a brain, or a liver in an abdomen, and generating one or more images of the object comprises generating one or more images depicting the cortex, the putamen, the globus pallidus, the red nucleus, the substantia nigra, or the subthalamic nucleus of the brain, or the liver in the abdomen.

In some implementations, the object comprises at least one of a multiple sclerosis lesion, a cancerous lesion, a calcified lesion, an ischemic lesion, or a hemorrhage, and generating one or more images of the object comprises generating one or more images depicting at least one of the multiple sclerosis lesion, the cancerous lesion, the calcified lesion, or the hemorrhage.

In some implementations, the operations further comprise of quantifying, based on the one or more images, a distribution of contrast agents introduced into the object in the course of a contrast enhanced magnetic resonance imaging procedure.

The details of one or more embodiments are set forth in the accompanying drawings and the description below. Other features and advantages will be apparent from the description and drawings, and from the claims.

DESCRIPTION OF DRAWINGS

FIG. 17. a) Fidelity cost and SSIM for various QSM reconstructions in a healthy subject, with COSMOS as the ground truth reference. b) Fidelity cost and SSIM for T2w and T2FLAIR in multi-contrast reconstruction.

Like reference symbols in the various drawings indicate like elements.

DETAILED DESCRIPTION

Figure 1:
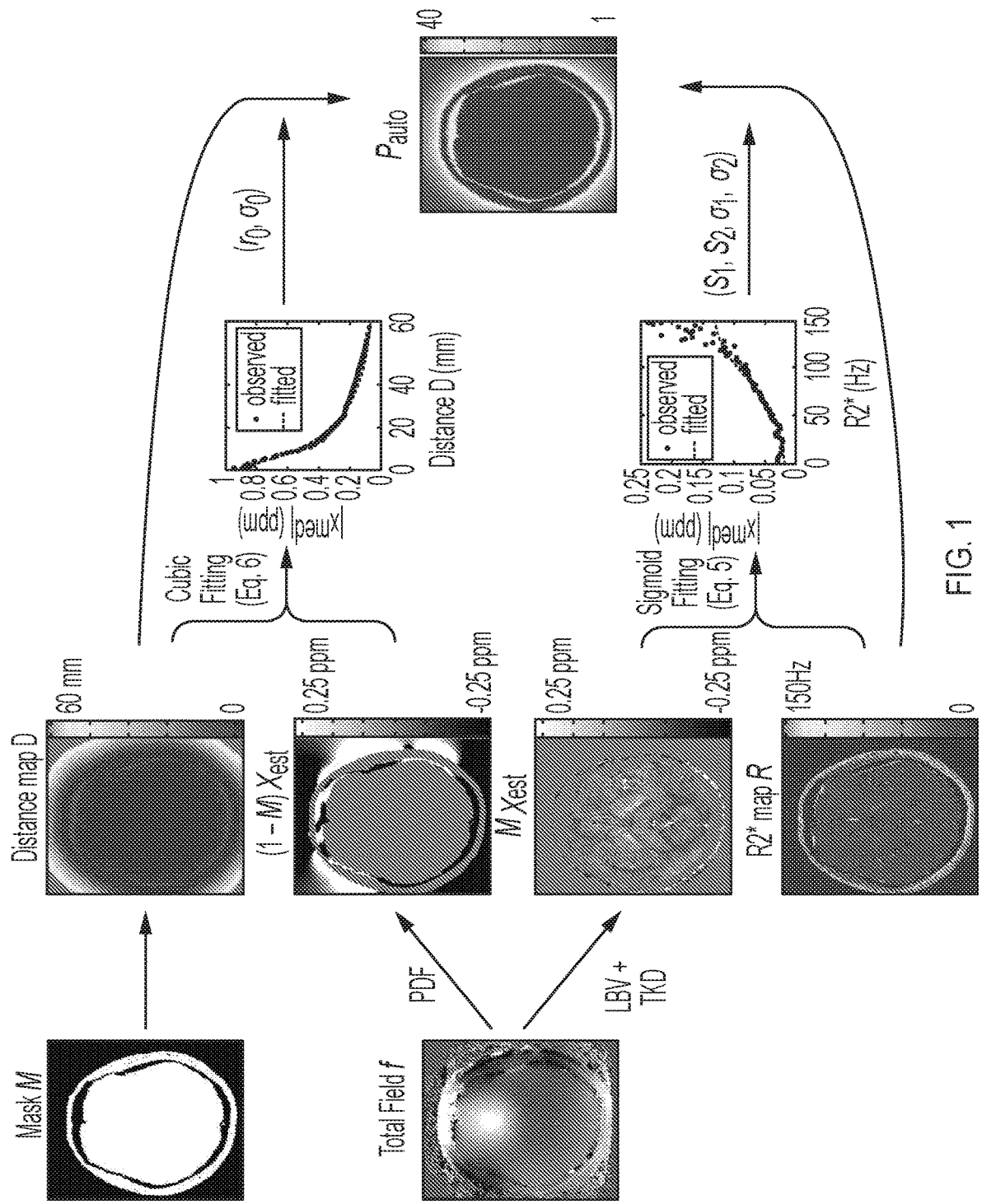
FIG. 1. Flow chart for generating the preconditioner $P_{auto}$ from a total field f and a soft tissue ROI mask M. An approximate susceptibility map $\chi_{est}$ is estimated using PDF and LBV+TKD for sources out- and inside M, respectively. Voxels outside M are grouped by their distance $\mathcal{D}$ towards the boundary of M, and the median absolute susceptibility $X^{med}$ within each group is calculated and then fitted to a cubically decay function with respect to $\mathcal{D}$. Voxels inside M are grouped by their R2* value $\mathcal{R}$ and the median absolute susceptibility $X^{med}$ within each group is calculated and then fitted to a sigmoid function with respect to $\mathcal{R}$. The fitted value for mean absolute susceptibility of each voxel is taken as the weight in the preconditioner $P_{auto}$.

Implementations of systems and methods for collecting and processing MRI signals of a subject, reconstructing maps of physical properties intrinsic to the subject (e.g., magnetic susceptibility, transport parameters, deoxyheme concentration), and reconstructing multiple contrast images are described below. Physical processes in tissue including magnetism, transport, and relaxation affect the time evolution of MRI signals. Phase data acquired at various echo times in a gradient echo sequence allow determination of the magnetic field generated by tissue susceptibility and therefore determination of susceptibility. Image data acquired in a time resolved manner during a contrast agent passage through tissue allow determination of tissue transport properties including convection velocity, diffusion, pressure gradient and permeability. Images of various contrasts including T1, T2, T2* and diffusion weightings have structural consistency. Precision mapping of physical parameters and reconstructing multiple contrast images are achieved through insightful or perceptive uses of image data in formulating and solving inverse problems.

Some of the disclosed implementations overcome limitations in quantitative susceptibility mapping (QSM), where the computation speed and accuracy and the Bayesian prior information affect QSM image quality and practical usage. In some implementations, to reconstruct maps of a subject's magnetic susceptibility, the iterative computation process of finding the susceptibility distribution that optimally fit available field data and tissue structure prior information is accelerated using automated adaptive preconditioning according to signal magnitude decay rate R2*. In some implementations, an artificial neural network is trained to reconstruct maps of a subject's magnetic susceptibility. In some implementations, the tissue structure prior information in a Bayesian method for estimating susceptibility is improved using artificial neural networks.

Implementations of these improvements have made QSM technology fast and accurate, extending QSM usage from the brain to including the skull, bone, heart and liver, and to quantification of deoxyheme associated with aerobic energy metabolism. QSM for determining the susceptibility distribution $\chi(r)$ is based on minimizing a cost function that fits the measured tissue magnetic field b(r) (in unit B0) to the dipole field $$d(r) = \frac{2z^2 - x^2 - y^2}{4\pi|r|^5}, b = d * \chi,$$

assuming gaussian noise in b. The susceptibility solution can be estimated under a regularization associated with a prior information. For mathematical analysis of susceptibility solution, the equivalent partial differential equation can be derived directly from Maxwell's equation with Lorentz sphere correction, which is a wave equation with respect to susceptibility $\chi$ (z-axis is time) and a Laplacian equation with respect to field b. Then, any field data incompatible with the dipole field causes artifacts according to the wave propagation with large values (divergence) at the cones of magic angle. The dipole incompatible part, including noise, discretization error, and anisotropy sources, generates artifacts defined by the wave propagator with the B0 field direction as the time axis. Granular noise causes streaking and contiguous error causes both streaking and shadow artifacts. The invention described here makes use of this mathematical fact to improve QSM speed and accuracy. Streaking artifacts are characterized by edges along the magic angle (54.7°) in k-space or the complimentary magic angle in image space, which are almost completely distinct from tissue edges. Accordingly, they can be minimized during numerical optimization by a regularization term based upon tissue structure information or an artificial neural network to identify solution of minimal artifacts or minimal streaking and shadowing. This is the morphology enable dipole inversion (MEDI) approach that impose structural consistency between the susceptibility map and prior knowledge such as derived from magnitude, phase and other structural images. Tissue structure information is numerically evaluated using edge gradient and L1 norm in some implementations, or using artificial neural network in some other implementations.

Some of the disclosed implementations overcome limitations in quantitative transport mapping (QTM), where the proper physics model for the underlying transport process to fit time-resolved image data affects the performance and accuracy of QTM. Time-resolved imaging of a tracer passing through tissue allows determination of tracer concentration time course. For example, contrast agent concentration in time resolved MRI can be mapped using QSM or other methods. The time-resolved mapping of tracer concentration can be modeled by the transport equations governing mass and momentum conservations. The mass conservation or continuity equation describes the local concentration temporal change according to the local divergence of mass flux consisting of a convection or drift velocity term and a diffusion term. The momentum conservation or Navier-Stokes equation describes flow in tissue according to pressure gradient and other forces. In some implementations, artificial neural network is used to estimate transport parameters (velocity, diffusion and pressure gradient) from time resolved images. In some implementations, flow is modeled in porous media by a velocity distribution. The data fitting for velocity mapping is solved by optimization using quasi Newton, alternating direction method of multipliers, or artificial neural network.

Some of the disclosed implementations overcome limitations in tissue oxygen extraction fraction (OEF) mapping, where the noise in magnitude and phase data, including complex data of a multiecho gradient echo (mGRE) sequence, challenges the separation of deoxyheme in venules and veins and iron diffusely stored in tissue (mostly in ferritin and its pathologic version hemosiderin). The physics modeling of both magnitude and phase data allows this separation of deoxyheme iron and diffusely stored iron, and enables OEF estimation from mGRE data without any vascular challenge. The problem that the inverse solution to this physics model is very prone to noise in data is addressed by grouping voxels of similar tissue together. In some implementations, this grouping is achieved by using an automated clustering analysis of signal evolution over echo time, or by imposing sparsity in modeling the signal time course through optimization of quasi Newton, alternating direction method of multipliers, or artificial neural network.

Some of the disclosed implementations overcome limitations in numerical optimization that is important to the solutions of complex and often ill-posed inverse problems in determining physical parameters from image data and in reconstructing multiple contrast images from undersampled data. The numerical optimization can be performed using quasi-Newton, alternating direction method of multipliers, or artificial neural network. Recently, the large computing power has made artificial neural network or deep learning (DL) very effective in extracting complex image features that can be recognized by human eyes but typically are difficult to be formulated in specific mathematical expressions. The huge number of weights in a DL network can be trained to model the complexity of desired but unformulatable image features. However, these DL network weights may not recognize new image features in testing data. In some implementations, the DL output is updated by imposing data fidelity through numerical optimization or through updating the network weights.

Precision mapping of physical properties improves upon many applications: including brain QSM with reduced shadow and streaking artifacts, with uniform ventricle CSF as an automatic and consistent zero reference, and without skull stripping; mapping oxygen extraction fraction of brain tissue; mapping susceptibility sources in the heart including oxygenation level and intramyocardial hemorrhage, and mapping blood flow velocity in tumor from dynamic imaging of contrast agents.

1. Automated Adaptive Preconditioner for QSM

In this section is described an automated adaptive preconditioner allowing high quality QSM from the total field in imaging various anatomies with dynamic susceptibility ranges.

1.1. Introduction

Quantitative Susceptibility Mapping (QSM) has been an increasingly active field in MRI to study tissue magnetic susceptibility property, as summarized in recent review articles from many leading groups. Susceptibility is changed in many pathological processes, including neurodegeneration, inflammation, hemorrhage, oxygenation, and calcification. QSM has been demonstrated as a powerful tool for lesion characterization, iron deposit quantification), oxygenation measurement and surgical guidance for deep brain stimulation. A fundamental approach in reconstructing the tissue susceptibility distribution from the measured magnetic field is to optimally solve the ill-posed field-to-susceptibility inverse problem with additional structural knowledge using Bayesian inference. Current numerical optimization solvers are iterative, and it is desired to accelerate iteration convergence for a targeted accuracy. These iterative solvers use a universal stopping criterion regardless of the image content, and iteration may be stopped before adequate convergence at lesions with large susceptibility values but occupying small fractions of the image volume, promoting severe streaking artifact.

Preconditioning has been proposed to accelerate iteration convergence in QSM. Preconditioned QSM can reconstruct QSM of the entire image volume (including bone and air cavities) directly from the total field without explicit or implicit background field removal. By incorporating R2* information in the preconditioner, preconditioned QSM can reduce the hypointense artifact associated with intracerebral hemorrhage (ICH) of very high susceptibility values. However, the reported preconditioner consists of a simple binary image with dual values selected manually for a given anatomy or application.

In this work is proposed a general and automated framework for constructing an adaptive preconditioner for the total field and R2* derived from the input gradient echo data, without assumptions on the underlying image content or the need for a manual selection of preconditioning weights. The automated adaptive preconditioner is compared with its empirical counterpart by their reconstruction performance in total field inversion (TFI) across different imaging scenarios including healthy brain, ICH brain and cardiac MRI.

1.2. Theory

Based on the previous work of TFI and QSM with automatic zero-referencing, the present inventors have proposed the following model for QSM:

$$\chi^* = Py^*, \quad [1]$$

$$y^* = \underset{y}{\mathrm{argmin}} \frac{1}{2} \|w(f - d*Py)\|_2^2 + \lambda_1 \|M_G \nabla Py\|_1 + \lambda_2 \|M_2(Py - \overline{(Py)_{M_2}})\|_2^2$$

with $\chi$ the susceptibility map over the entire field of view, * the convolution with the dipole kernel d, w the noise weighting, f the total field, $\nabla$ the gradient operator and $M_G$ the binary edge mask derived from the magnitude image. In the last term, the $L_2$ regularization enforces the homogeneity within a pre-determined region $M_2$, e.g. the ventricular cerebrospinal fluid (CSF) in brain QSM. $\overline{(\bullet)_{M_2}}$ denotes the operator that computes the mean value within $M_2$. P is the preconditioner, which is currently constructed as a binary matrix:

$$P_{emp} = P(r) = \begin{cases} 1, & r \in M \\ P_S, & \text{otherwise} \end{cases} \quad [2]$$

where r denotes the location for each voxel, M is the mask for tissue ROI. The $P_S > 1$ is empirically determined for each anatomy and application. Given the availability of R2* information, P can be constructed as:

$$P_{emp+R2^*} = P(r) = \begin{cases} 1, & r \in M \cap M_{R2^*} \\ P_S, & \text{otherwise} \end{cases} \quad [3]$$

where $M_{R2^*}$ is the region with low R2* value ($M_{R2^*}:=R2^*<30$ Hz). The difference in those weights (1 vs. $P_S$) represents the contrast between weak susceptibility of soft tissues and relatively strong susceptibility sources including air, bone and hemorrhage.

To fully exploit the capacity of preconditioning in accelerating reconstruction of QSM of various image anatomies, P needs to be extended from binary values to a continuous range of weights. The present inventors propose an automated generation of an adaptive preconditioner from the total field f and R2*, as illustrated in FIG. 1. First, an approximate susceptibility map is estimated rapidly from the field input f. The susceptibility of strong sources outside the ROI M is estimated using the projection onto dipole fields method (PDF), while the susceptibility inside M is calculated using the Laplacian boundary values method (LBV) followed by Truncated K-space Division (TKD). These two susceptibility components are combined into a single map $\chi_{est}$.

Then weights of the preconditioner are generated from $\chi_{est}$ by addressing noise and artifacts in $\chi_{est}$ in the following manner of averaging and trending. The present inventors group voxels with similar spatial or R2* properties, depending on where the voxels are relative to the ROI M, and calculate the median $\chi^{med}$ of absolute susceptibility values within each group. Inside M, voxels are grouped by their R2* values $\mathcal{R}$, each group is defined by a bin of 1-Hz width in R2* value, and $\chi^{med}$ is determined by fitting $|\chi^{est}|$ to a sigmoid curve with respect to $\mathcal{R}$:

$$\chi^{med} \sim (\sigma_2 - \sigma_1) \frac{1}{1 + e^{-(\mathcal{R} - s_1)/s_2}} + \sigma_1. \quad [4]$$

Here $[\sigma_1, \sigma_2]$ control the output range and $(s_1, s_2)$ control the shape. The choices of R2* binning and sigmoid curve are motivated by connections between R2* and susceptibility and by soft thresholding.

Outside M, due to the absence of reliable R2* measurement, voxels are grouped by their distance $\mathcal{D}$ towards the boundary of the mask M. Each group is denoted by a bin of 1-mm width in $\mathcal{D}$ value, and $\chi^{med}$ is calculated by fitting $|\chi_{est}|$ to a cubic decay function with respect to $\mathcal{D}$:

$$\chi^{med} \sim \sigma_0 \left(1 + \frac{\mathcal{D}}{r_0}\right)^{-3} \quad [5]$$

where $\sigma_0$ and $r_0$ control its scale and decay rate, respectively. The cubic decay is motivated by the similar spatial decay of the dipole kernel.

The final preconditioner P is then constructed as:

$$P_{auto} = P(r) = \begin{cases} \frac{\sigma_0}{\sigma_1}\left(1 + \frac{\mathcal{D}}{r_0}\right)^{-3}, & r \notin M \\ \left(\frac{\sigma_2}{\sigma_1} - 1\right)\frac{1}{1 + e^{-(\mathcal{R} - s_1)/s_2}} + 1, & r \in M \end{cases} \quad [6]$$

Note that, consistent with previous work, P is scaled by $\sigma_1$ such that the weight for soft tissues (low R2*) is close to 1. The generated preconditioner P is provided to TFI (Eq. 1), which is solved using the quasi Newton method combined with the conjugate gradient (CG) solver, or using the alternating direction method of multiplier (ADMM).

1.3. Materials and Methods

The present inventors designed a numerical simulation to analyze the accuracy of the proposed automated preconditioner $P_{auto}$ (Eq. 6) for healthy brain (non-ICH) and brain with intracerebral hemorrhage (ICH), compared with its empirical counterparts $P_{emp}$ (Eq. 2) and $P_{emp+R2^*}$ (Eq. 3). They then compared their performance for in vivo brain QSM of both healthy subject and ICH patient. Finally, they were tested on cardiac QSM of healthy subject.

Implementation details. For $P_{emp}$ (Eq. 2) and $P_{emp+R2^*}$ (Eq. 3), the weight $P_S$ was chosen as 30 for brain/head QSM and 20 for cardiac QSM. In estimating the approximate solution $\chi_{est}$, PDF was performed with 5 CG iterations for sources outside M. For sources inside M, LBV was performed with a 3-voxel erosion of the ROI mask M to exclude noisy field measurements at the boundary, followed by TKD with a threshold of 0.2. At the weight generation stage, the nonlinear least squares fitting for parameters ($\sigma_0$, $\sigma_1$, $\sigma_2$, $r_0$, $s_1$, $s_2$) was performed using Matlab's fmincon routine. The distance map $\mathcal{D}$ was calculated using the Euclidean Distance Transform for Variable Data Aspect Ratio. For brain/head QSM, $\lambda_1 = 0.001$ and $\lambda_2 = 0.1$ were used in (Eq. 1), with M$_2$ chosen as ventricular CSF which can be automatically generated from multi-echo magnitude images. Susceptibility values were then referenced to the mean susceptibility within M$_2$. For cardiac QSM, $\lambda_1=0.001$ and $\lambda_2=0$ were used. The quasi Newton Conjugate Gradient (GNCG) solver was implemented. For the choice of numerical conditioning parameter E for calculating the weak derivative of L$_1$-norm in Eq. 1, M$_G\nabla$Py was replaced with $$\sqrt{|M_G \nabla Py|^2 + \epsilon} \quad [7]$$

to avoid division by zero, and $\epsilon = P^2 \times 10^{-6}$ was chosen such that the numerical conditioning weight would remain approximately $10^{-6}$ for weak susceptibility tissue (P≈1) but increase for strong susceptibility sources (P>1). The goal of this increased conditioning weight is to accelerate GNCG convergence.

Simulation. A numerical head phantom of size 180×220×128 was constructed from Zubal phantom with known susceptibilities simulating different brain tissues: white matter (WM) −0.046 ppm, gray matter (GM) 0.053 ppm, thalamus (TH) 0.073 ppm, caudate nucleus (CN) 0.093 ppm, putamen (PU) 0.093 ppm, globus pallidus (GP) 0.193 ppm, superior sagittal sinus (SSS) 0.27 ppm and cerebrospinal fluid (CSF) 0 ppm. Air (9 ppm), muscle (0 ppm) and skull (−2 ppm) were distributed outside brain (FIG. 2a). This phantom was then used to simulate two different scenarios: (A) non-ICH subject and (B) patient with intracerebral hemorrhage (ICH), which was represented by a spherical susceptibility source of 2 ppm located inside the brain mask (FIG. 3a). In both cases, the total field was computed from the true susceptibility map using the forward relation: f=d*$\chi$. Gaussian white noise (SNR=100) was added to this field. R2* was also simulated for each tissue type: WM 20 Hz, GM 20 Hz, TH 20 Hz, CN 30 Hz, PU 30 Hz, GP 45 Hz, SSS 45 Hz, CSF 4 Hz and ICH 100 Hz. For each iteration i, the root mean square error $$(RMSE)\sqrt{\frac{1}{N}\sum_i (M\chi_i - M\chi_{T,i})^2}$$

between the estimated brain susceptibility M$_{\chi i}$ and the ground truth M$_{\chi T}$, and the average susceptibilities of CN and GP were calculated as metrics of reconstruction accuracy.

In vivo experiment: healthy head. Five healthy subjects were scanned at 3 T (GE, Waukesha, WI) using multi-echo GRE with monopolar readout. The imaging parameters were: FA=15, FOV=25.6 cm, TE$_1$=5.0 ms, TR=39 ms, #TE=6, $\Delta$TE=4.6 ms, acquisition matrix=512×512×144, voxel size=0.5×0.5×1 mm$^3$, BW=±62.5 kHz and a total scan time of 7 min. The scan was repeated at 5 different orientations for COSMOS reconstruction of brain QSM, with the brain mask generated by BET. At one orientation, the total field was estimated from multi-echo GRE images followed by graph-cut based phase unwrapping SPURS. ROI mask M for the entire head was determined by thresholding the magnitude image I: M:=I>0.15×I$_{max}$, where I$_{max}$ is the largest voxel value in I. The R2* map was estimated using ARLO. TFI with different preconditioner choices P$_{emp}$ (Eq. 2), P$_{emp+R2*}$ (Eq. 3) and P$_{auto}$ (Eq. 6) was used to reconstruct the whole head QSM. Upon QSM reconstruction, the susceptibility of CN and GP were measured within manually drawn ROIs. The same measurement was also applied to COSMOS. Linear regression on susceptibility measurements between TFI and COSMOS was performed over all voxels inside the brain for each preconditioner choice, respectively.

In vivo experiment: ICH brain. Five patients with Intracerebral hemorrhage (ICH) were scanned at 3T (GE, Waukesha, WI) using multi-echo GRE with monopolar readout. The imaging parameters were: FA=15, FOV=24 cm, TE$_1$=4.5 ms, TR=49 ms, #TE=8, $\Delta$TE=5 ms, acquisition matrix=512×512×64, voxel size=0.47×0.47×2 mm$^3$, BW=±62.5 kHz and a total scan time of 4 min. The total field was estimated from multi-echo GRE images followed by graph-cut based phase unwrapping. The R2* map was calculated using ARLO. TFI with different preconditioner choices P$_{emp}$ (Eq. 2), P$_{emp+R2*}$ (Eq. 3) and P$_{auto}$ (Eq. 6) was used to reconstruct the QSM of the brain, with the brain ROI determined by BET. Upon QSM reconstruction, the susceptibility of CN and GP were measured using manually drawn ROIs. The mean susceptibility within a 5 mm-wide layer surrounding the ICH site (segmented by an experienced radiologist) was computed for each QSM, respectively, to quantify the hypo-intense artifact around ICH.

In vivo experiment: Cardiac MRI of 3 healthy subjects were performed on 1.5 T (GE, Waukesha, WI) using a breath-hold electrocardiographic-triggered 2D multi-echo GRE in the short-axis view. The imaging parameters were: TE$_1$=3.6 ms, TR=23 ms, #TE=8, $\Delta$TE=2.2 ms, in-plane voxel size=1.25×1.25 mm$^3$, slice thickness=5 mm, #slices=20. Flow compensation was applied in the readout and slice direction. Acceleration factor R=1.5, with one slice scanned at each breath-hold of approximately 15 s each. The average scan time was ~12 min. The total field was estimated from multi-echo GRE images using SPURS for graph-cut based unwrapping and IDEAL for water/fat separation. R2* map was calculated using ARLO. TFI with different preconditioner choices P$_{emp}$ (Eq. 2), P$_{emp+R2*}$ (Eq. 3) and P$_{auto}$ (Eq. 7) was used to reconstruct QSM. The susceptibility difference between right ventricle (RV) and left ventricle (LV) was measured on the QSM of each method, using manually drawn ROIs. Then the blood oxygenation difference $\Delta$SaO$_2$ between arterial blood (LV) and venous blood (RV) was calculated from the susceptibility difference $\Delta\chi$ (unit: ppm) using the relation:

$$\Delta SaO_2 = \frac{\Delta\chi}{9.49 \times 0.151}. \quad [8]$$

1.4. Results

Figure 2:
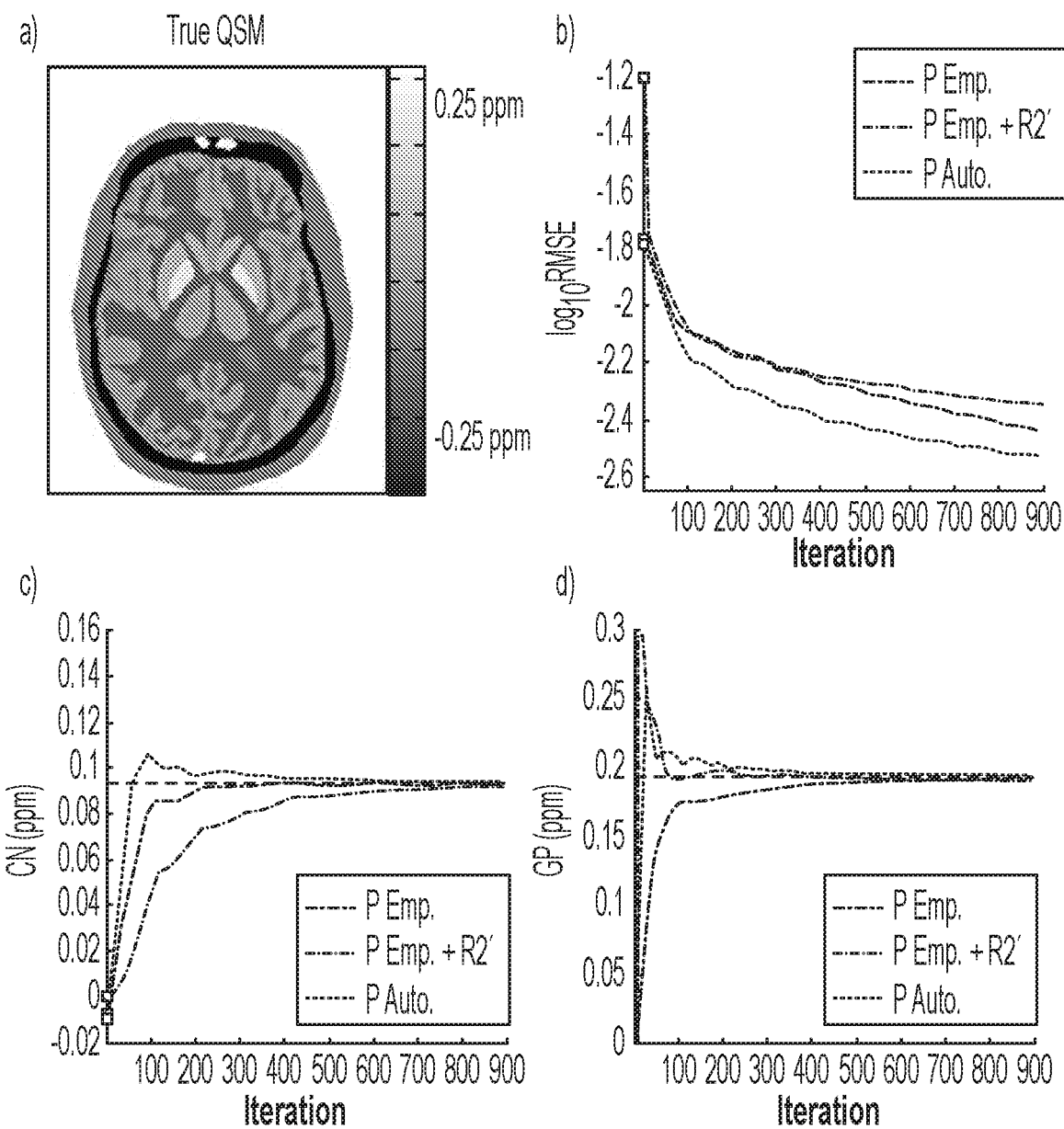
FIG. 2. Simulation results for non-ICH scenario. True susceptibility map $\chi_T$ (a), root-mean-square-error (RMSE) between the reconstructed and true QSM (b), ROI measurement for CN (c) and GP (d) at different CG iteration. $P_{auto}$ achieved the lowest RMSE among the three methods. Under-estimation of CN was consistently observed for $P_{emp+R2*}$ compared to $P_{emp}$ and $P_{auto}$.

Simulation Results from the non-ICH scenario are shown in FIG. 2. All three preconditioner choices reached RMSE<0.005 ppm at 1000 CG iterations, while P$_{auto}$ achieved the lowest RMSE (FIG. 2b). The CG iteration number needed by each preconditioner in order to converge to ±5% range around the true value of each ROI was 170 (P$_{emp}$), 550 (P$_{emp+R2*}$) and 180 (P$_{auto}$) for CN (FIG. 2c); 260 (P$_{emp}$), 70 (P$_{emp+R2*}$) and 170 (P$_{auto}$) for GP (FIG. 2d).

Figure 3:
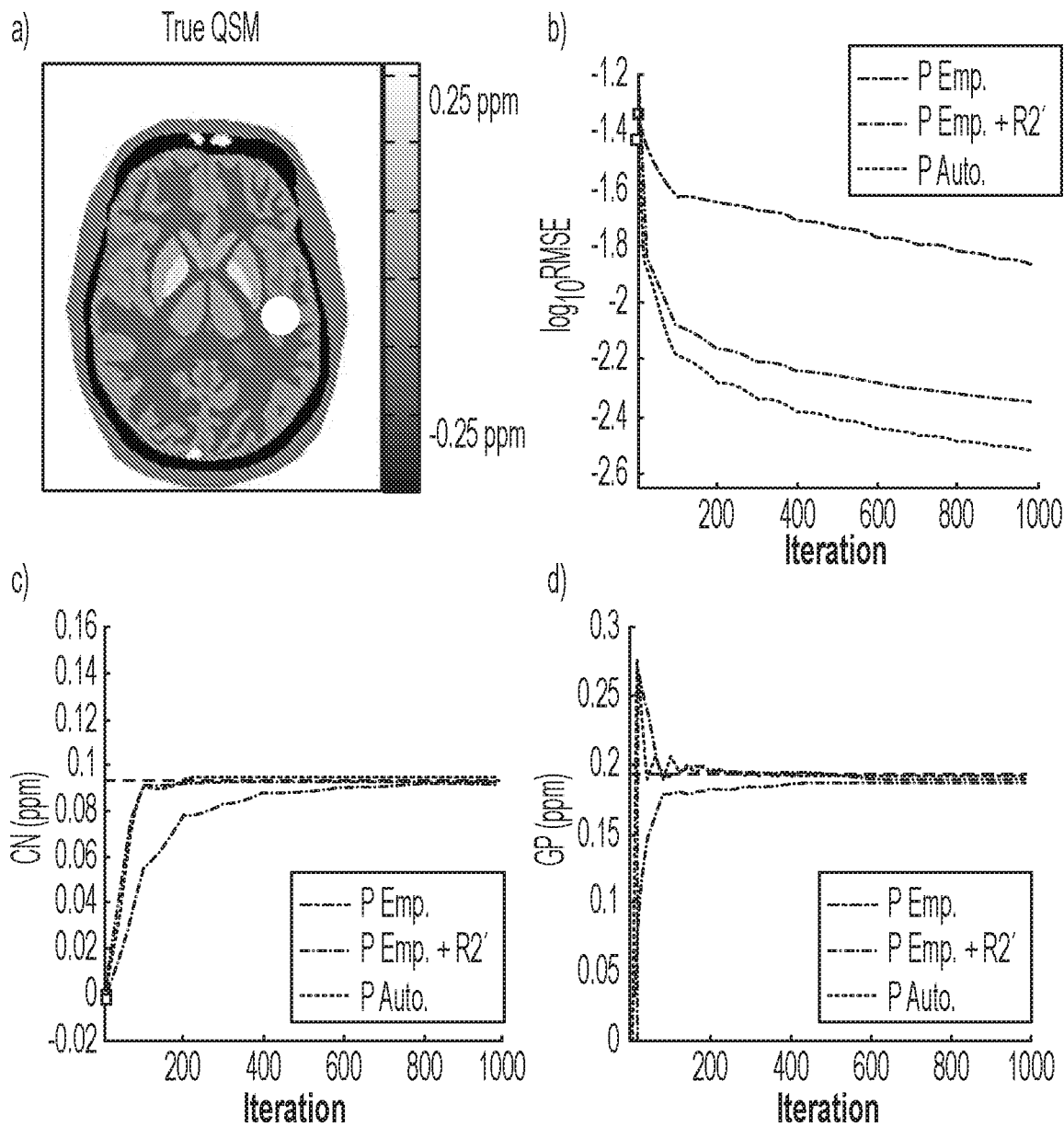
FIG. 3. Simulation results for ICH scenario. True susceptibility map $\chi_T$ (a), root-mean-square-error (RMSE) between the reconstructed and true QSM (b), ROI measurement for CN (c) and GP (d) at different CG iteration. $P_{auto}$ achieved the lowest RMSE among three methods. At $1000^{th}$ CG, $P_{emp}$ has a much larger RMSE than those of $P_{emp+R2*}$ and $P_{auto}$. Under-estimation of CN was consistently observed for $P_{emp+R2*}$ compared to $P_{emp}$ and $P_{auto}$. For GP measurement, $P_{emp}$ showed a bias of −3% at $1000^{th}$ CG, while the bias of $P_{emp+R2*}$ or $P_{auto}$ was negligible.
Figure 4:
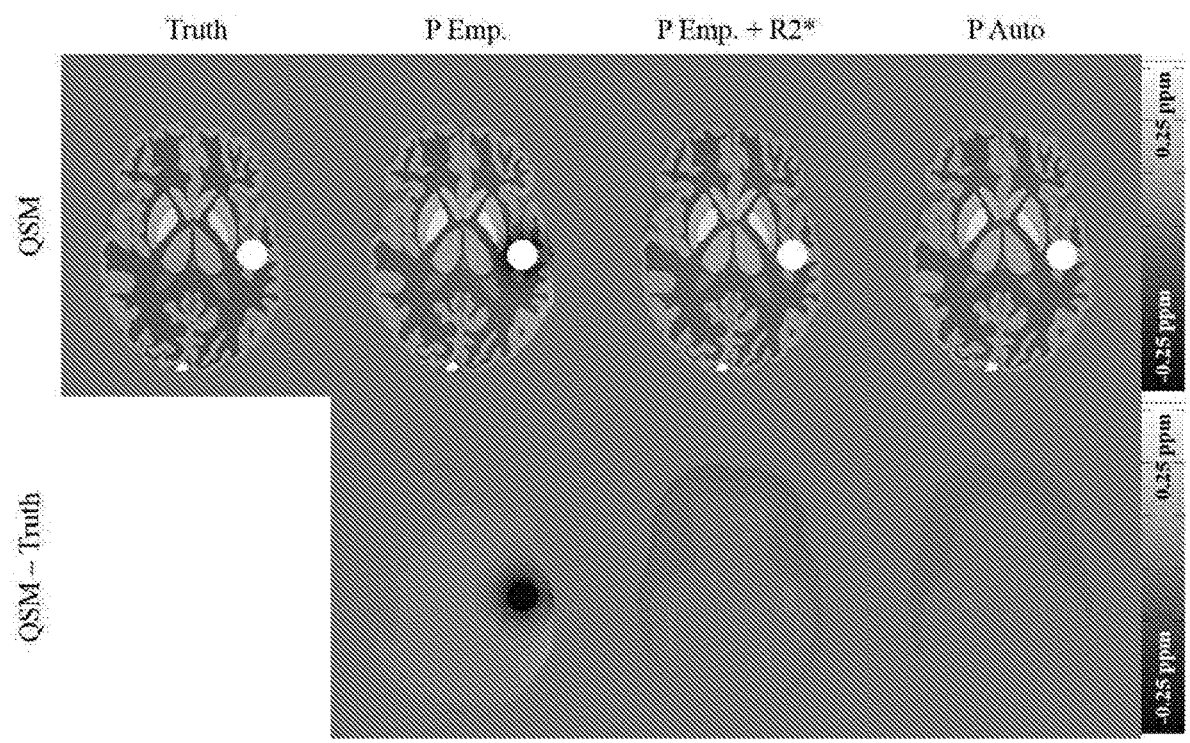
FIG. 4. Simulation result for ICH scenario: true brain QSM and brain QSM reconstructed by TFI using $P_{emp}$, $P_{emp+R2*}$ and $P_{auto}$ at the $1000^{th}$ CG iteration (top row). Difference with respect to the true QSM was also shown (bottom row). Strong hypo-intense artifact around the ICH was present in $P_{emp}$ result, leading to larger RMSE with respect to true brain susceptibilities shown in FIG. 3b. This artifact over-shadowed part of the nearby GP.

Results from the ICH scenario are shown in FIG. 3. For ICH TFI, both P$_{emp+R2*}$ and P$_{auto}$ reached RMSE<0.005 ppm at 1000 CG iterations with lower RMSE for P$_{auto}$, while the RMSE using P$_{emp}$ failed to go below 0.010 ppm (FIG. 3b). This can be appreciated from the hypo-intense artifact around ICH in P$_{emp}$ result at 1000 CG iterations (FIG. 4). The CG iteration number needed by each preconditioner in order to converge to ±5% range around the true value of each ROI was 90 ($P_{emp}$), 400 ($P_{emp+R2*}$) and 90 ($P_{auto}$) for CN (FIG. 3c); 260 ($P_{emp}$), 100 ($P_{emp+R2*}$) and 110 ($P_{auto}$) for GP (FIG. 3d).

In Vivo Brain Imaging

Figure 5:
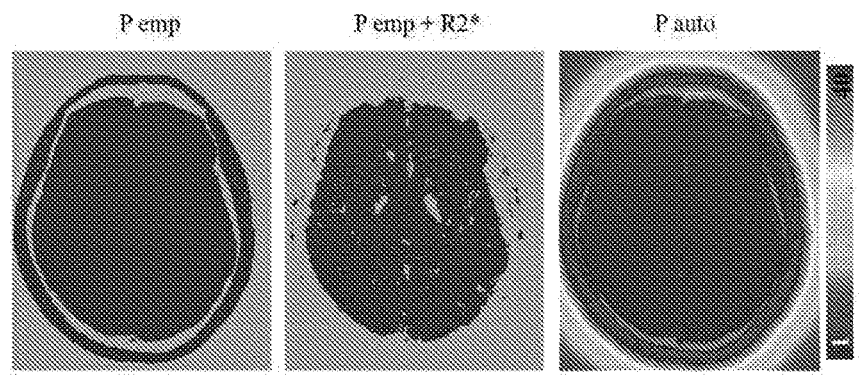
FIG. 5. Example of preconditioning one healthy subject using COSMOS as reference. Top row: preconditioner maps of $P_{emp}$, $P_{emp+R2*}$ and $P_{auto}$. Bottom row: QSM for COSMOS, $P_{emp}$, $P_{emp+R2*}$ and $P_{auto}$. $P_{emp}$ and $P_{auto}$ obtain similar results for the entire head and comparable results with COSMOS for the brain. The contrast between CN and surrounding whiter matter is less distinct in $P_{emp+R2*}$ compared to other maps.
Figure 5:
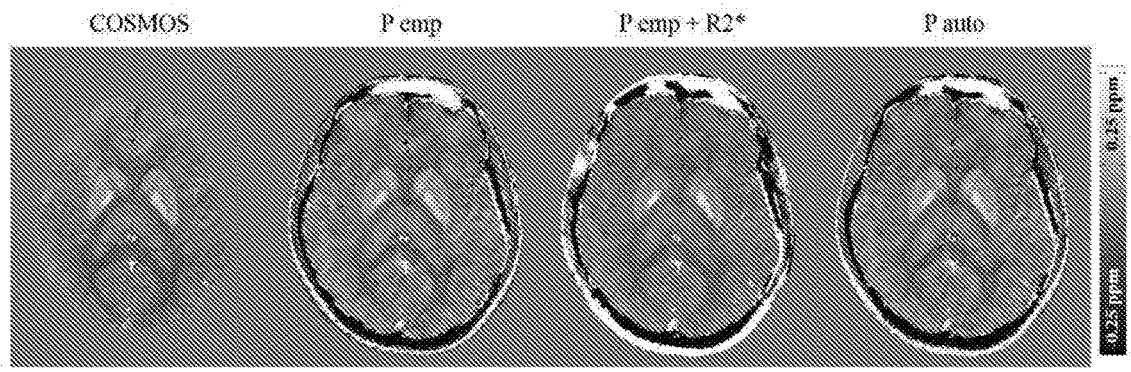

An example of whole head TFI reconstruction of one healthy subject is shown in FIG. 5. It was noted that with the R2* threshold (30 Hz) used in $P_{emp+R2*}$, regions with higher R2* such as GP were assigned the same weight ($P_S$=30) as the background. In contrast, $P_{auto}$ adaptively assigned weights to different regions according to their R2* values (Eq. 7). FIG. 5 also showed the QSM reconstructed by COSMOS, TFI with $P_{emp}$, $P_{emp+R2*}$ and $P_{auto}$. The whole head QSM obtained used $P_{auto}$ was visually similar to $P_{emp}$ as well as COSMOS. Meanwhile, the gray/white matter contrast was less distinct in the $P_{emp+R2*}$ outcome, especially at the boundary of CN. This was confirmed by the CN susceptibility measurement for this subject: 0.058 ppm for COSMOS, 0.054 ppm for $P_{emp}$, 0.023 ppm for $P_{emp+R2*}$ and 0.050 ppm for $P_{auto}$. ROI measurement for CN and GP across all five healthy subjects are summarized in FIG. 7a. The average difference relative to COSMOS was −5% ($P_{emp}$), −45% ($P_{emp+R2*}$) and −6% ($P_{auto}$) for CN and −9% ($P_{emp}$), −3% ($P_{emp+R2*}$) and −4% ($P_{auto}$) for GP. The linear regression of brain tissue susceptibilities between TFI and COSMOS showed a slope of 0.77 for $P_{emp}$, 0.67 for $P_{emp+R2*}$ and 0.76 for $P_{auto}$ across the five subjects.

Figure 6:
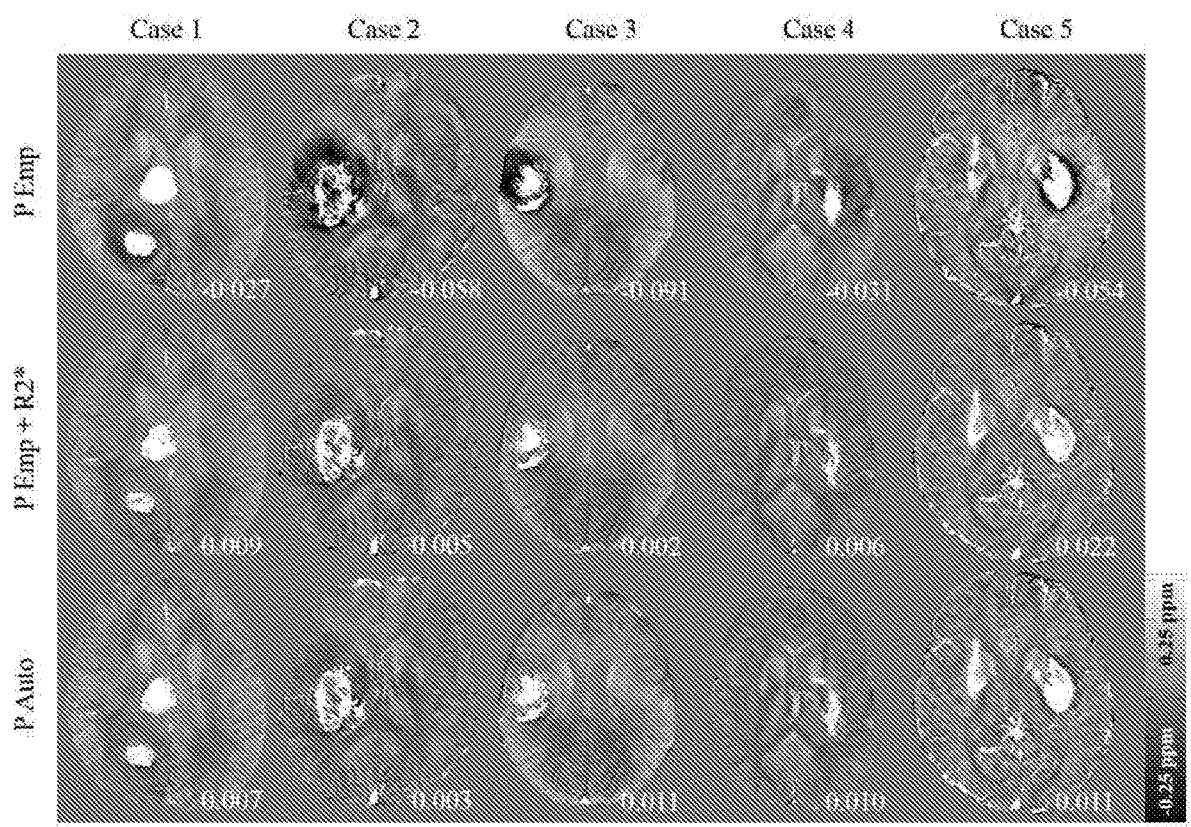
FIG. 6. QSM for 5 patients with ICH. Hypo-intense artifacts are observed around the ICH site in the output of $P_{emp}$, while they are suppressed on both $P_{emp+R_2*}$ and $P_{auto}$. The mean susceptibility value within a 5 mm-wide layer outside the ICH is noted at the right-bottom corner of each map. The increase in this susceptibility measurement, as observed in $P_{emp+R_2*}$ and $P_{auto}$ compared to $P_{emp}$, reflects the reduced hypo-intense artifact.

A QSM for each of the 5 ICH patients is shown in FIG. 6. A hypo-intense artifact around the ICH site present for $P_{emp}$ was reduced for $P_{emp+R2*}$ and $P_{auto}$. The mean susceptibility within a 5 mm-wide layer surrounding the ICH site is shown in the lower right hand corner of each QSM, indicating an average increase of 0.061 ppm for $P_{emp+R2*}$ and 0.060 ppm for $P_{auto}$, compared to $P_{emp}$. However, $P_{emp+R2*}$ significantly under-estimated CN susceptibility compared to $P_{emp}$ and $P_{auto}$, as shown by the ROI measurement (FIG. 7b): across 5 patients, the average CN measurement was 0.068 ppm for $P_{emp}$, 0.040 for $P_{emp+R2*}$ and 0.067 ppm for $P_{auto}$–Average GP measurement was 0.168 ppm for $P_{emp}$, 0.219 for $P_{emp+R2*}$ and 0.211 ppm for $P_{auto}$.

In Vivo Heart Imaging

Figure 8:
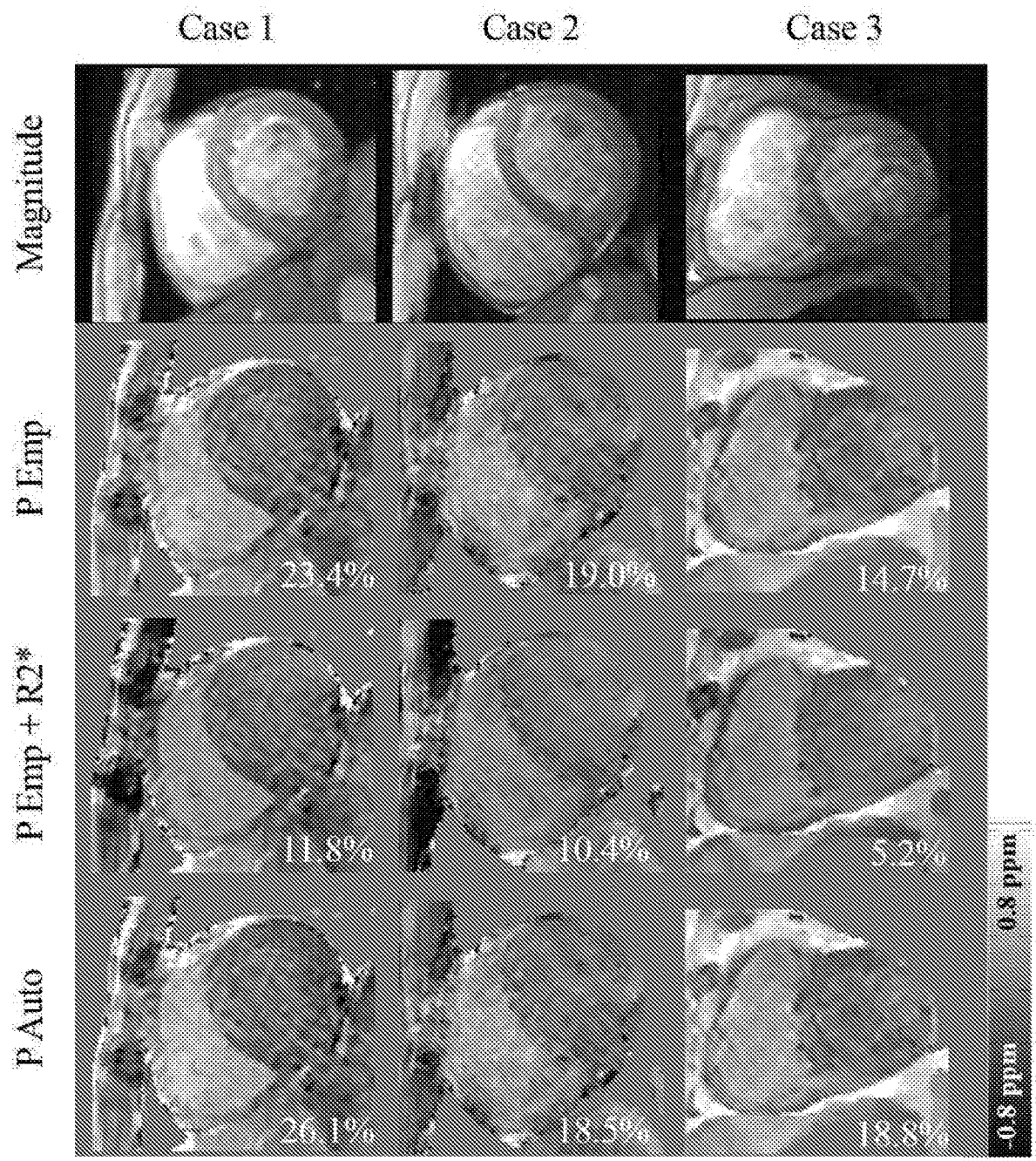
FIG. 8. Cardiac QSM results for 3 healthy subjects. From top to bottom: magnitude image at short-axis view, QSM reconstructed using $P_{emp}$, $P_{emp+R_2*}$ and $P_{auto}$. Oxygenation level difference between LV and RV calculated from the susceptibility difference between LV and RV is noted at the bottom right-hand corner of each map, indicating under-estimation by $P_{emp+R_2*}$ compared to $P_{emp}$ and $P_{auto}$.

FIG. 8 shows the cardiac QSM in the 3 healthy subjects reconstructed by TFI using $P_{emp}$, $P_{emp+R2*}$ and $P_{auto}$. Under-estimation was observed in $P_{emp+R2*}$ result for RV-LV susceptibility measurement compared to $P_{emp}$ and $P_{auto}$, as well as in the converted blood oxygenation difference $\Delta SaO_2$: 14.7%~23.4% for $P_{emp}$, 5.2%~11.8% for $P_{emp+R2*}$ and 18.5%~26.1% for $P_{auto}$. A reference value for the blood oxygenation difference in healthy subject is 18.8%.

1.5. Conclusion

A novel algorithm to automatically construct a general adaptive preconditioner for QSM is described using the total field and R2* derived from the input gradient echo data. This automated adaptive preconditioner overcomes the limitations of binary values and manual selection in the previous implementation of preconditioned QSM. The data shows that the automated adaptive preconditioner achieves the lowest error metrics in numerical simulation compared to the previous R2* based preconditioners. The automated adaptive preconditioner suppresses hemorrhage-related artifacts and preserves the surrounding brain tissue contrast at the same time.

An important benefit of preconditioned QSM is to eliminate errors in traditional QSM reconstruction that involves two separate steps: background field removal and local field inversion. The background field removal is intended to address the drastic contrast between background susceptibility sources such as air and bone, and the local sources including parenchymal tissues. The fitting processes are intrinsically separated and hence suffer from error propagation from unresolved background field into inverted local susceptibility. To address this error propagation, Laplacian based methods are proposed that facilitate implicit background field removal. They avoid the sequential fitting of background and local field by applying Laplacian operation to the forward signal model, which intrinsically removes the harmonic background field component. Nevertheless, the Laplacian implementation requires erosion of the region of interest (ROI) due to unreliable phase measurements beyond the ROI boundary, therefore preventing a complete depiction of the brain parenchyma.

The development of preconditioning for accelerating conjugate gradient (CG) solver has been discussed in-depth throughout the literature of numerical optimization. While traditional methods involve spectrum analysis of eigenvalues of the system matrix, direct application of such an approach to TFI reconstruction problem is challenging due to the huge problem size and the intrinsic convolution operation. Although recent work has shown that a preconditioner can be constructed in k-space to approximate the inverse of dipole kernel and gradient operator, its implementation for TFI is not straightforward due to the presence of the SNR weighting w and morphology constraint $M_G$ in Eq. 1. Meanwhile, research has also been focused on developing a preconditioner by leveraging prior information of the unknown solution, leading to a branch called prior-enhanced preconditioning. In its regard, the behavior of preconditioned CG is related to generalized Tikhonov regularization:

$$\operatorname*{argmin}_{\chi} \|A\chi - b\|_2^2 + \lambda_{Tik}\|\Gamma\chi\|_2^2. \qquad [9]$$

The principle idea is that, one can construct a whitening operator $\Gamma$ simulating the inverse covariance matrix $\Sigma^{-1}$ by $\gamma^H \gamma \approx \Sigma^{-1}$, if the prior distribution of $\chi$ is known as a Gaussian distribution $\chi \sim \mathcal{N}(0, \Sigma)$. It has been shown that, if a preconditioner P is chosen such that $P^{-1} \approx \Gamma$, improved convergence is obtained within limited iterations by solving the following problem instead:

$$\chi = Py, \operatorname*{argmin}_{y}\|APy - b\|_2^2. \qquad [10]$$

This provides a guideline for choosing preconditioner P: the transformed variable $P^{-1}\chi$ should have unit variance: $P^{-1}\chi \sim \mathcal{N}(0, I)$. In other words, P should be proportional to the presumed susceptibility magnitude of each voxel. By this guideline, a binary preconditioner was employed in the previous TFI work, in which an empirical weight, 30, was assigned to strong susceptibility sources such as air, bone and hemorrhage, whereas weight 1 was assigned to weak soft tissues. The current work enriches the preconditioner with more flexibilities in depicting the spatial distribution and dynamic contrast of the susceptibility map. It efficiently generates an approximated solution $\chi_{est}$ from the field input using PDF and LBV+TKD, and the absolute susceptibility value in $\chi_{est}$ was used in constructing the preconditioning weights. It is noted that, instead of directly using $|\chi_{est}|$ at each voxel, voxels are grouped by their spatial (distance towards object's boundary) or relaxational property (R2*), and the median value of the observed absolute susceptibility value calculated within each group. This approach aims to mitigate the influence of the noise and artifact in a single voxel, while median is chosen due to its robustness against outliers.

Figure 9:
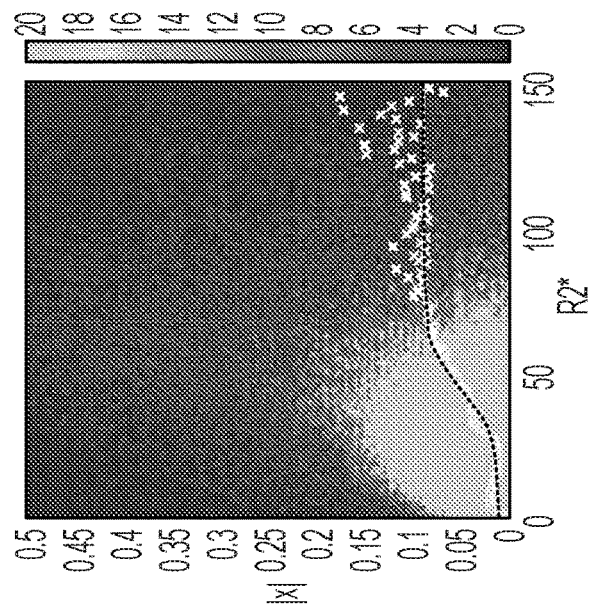
FIG. 9. Comparison of non-ICH subject (top row) and patients with ICH (bottom row). QSM ($1^{st}$ column) and R2* map ($2^{nd}$ column) are displayed with the corresponding R2*−|χ| scatterplot shown on the right. Notice the difference in vertical range. Pink cross denotes the median absolute susceptibility $\lambda^{med}$ over all voxels contained in each 1-Hz bin of R2*. A sigmoid function (red curve) is then fitted to the relation between R2* and $\chi^{med}$.
Figure 9:
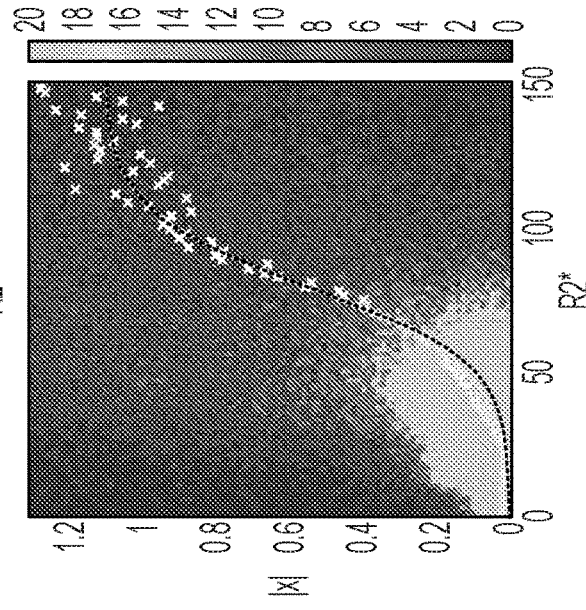
Figure 9:
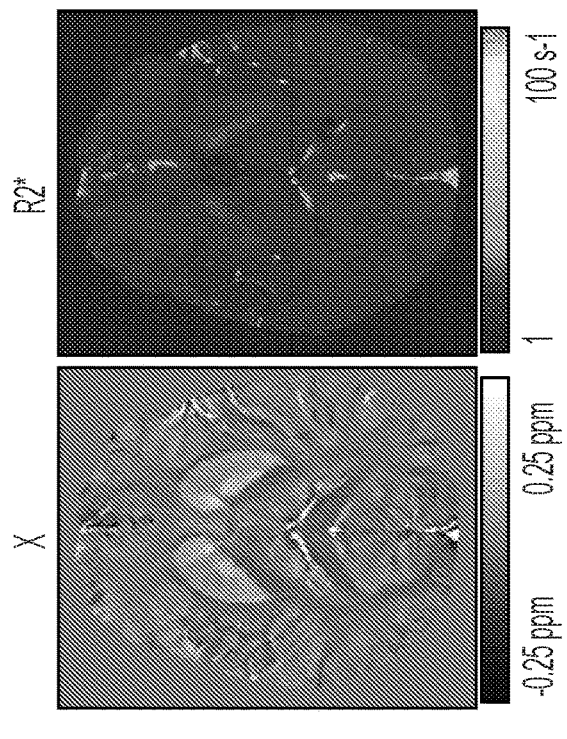
Figure 9:
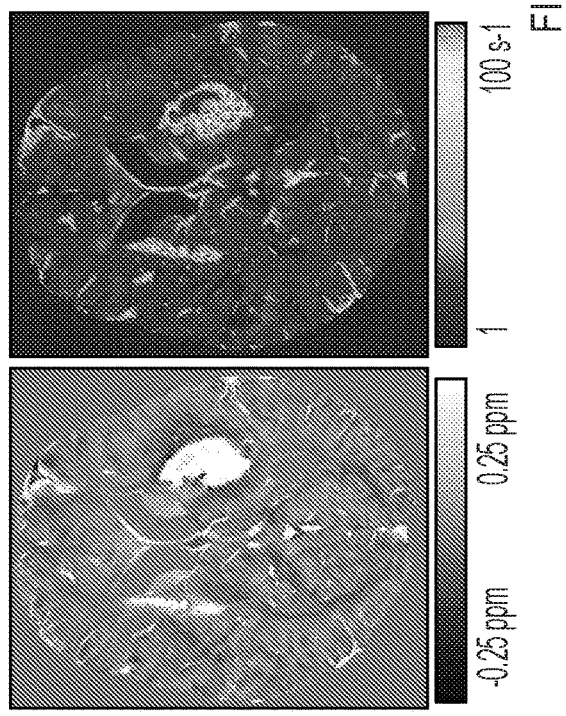

R2* information is essential in the disclosed preconditioning technique, since it depicts the location of strong susceptibility tissues within the subject, such as ICH. As seen in simulation (FIG. 4) and in vivo experiment (FIG. 6), incorporation of R2* in the preconditioner ($P_{emp+R2*}$ and $P_{auto}$) markedly suppressed the hypo-intense artifact surrounding the ICH site. Otherwise the QSM may suffer from qualitative and quantitative degradation, especially for structures close to ICH, as observed in the under-estimation of GP in FIG. 3d. Previous work employed a simple binary threshold framework to differentiate weak/strong sources by their R2* and assigned the same weight to high-R2* regions as it did to the background. The proposed method incorporates R2* contrast into the construction of preconditioner in a more adaptive manner. After obtaining a rough estimate of tissue susceptibilities, a sigmoid function a (Eq. 5) is employed to simulate the monotonic relation between R2* and observed absolute susceptibility value $\chi^{med}$ This monotone relation incorporates the prior knowledge that higher R2* value typically implies larger absolute susceptibility value, as in the case of hemorrhage (strongly positive value) or calcification (strongly negative value). An alternative perspective is to treat susceptibility $\chi_i$ at each voxel as a random variable dependent on the value of R2* value $\mathcal{R}$, with the conditional probability distribution $\mathcal{N}(0,\sigma^2(\mathcal{R}))$. Using $\sigma(\mathcal{R})$ as the preconditioning weight, $P^{-1}\chi$ presumably has unit variance. It is noted that if $\sigma_1=1$, $\sigma_2=30$, $s_1=30$, $s_2\ll1$, the sigmoid function (Eq. 5) reduces to the hard threshold used in $P_{emp+R2*}$. Therefore, the proposed preconditioner can be thought as a generalized version of its empirical counterpart. FIG. 9 shows how the fitted sigmoid function accounts for different dynamic contrasts in non-ICH and ICH subjects: compared to non-ICH brain, the ICH data produces a sigmoid curve with much higher $\sigma_2$, which corresponds to the increased population of ICH voxels at the high-R2*-high-susceptibility area. This built-in scalability preserved the capability to suppress ICH-related artifacts (FIG. 4 and FIG. 6) and meanwhile addressed the under-estimation issue in the previous empirical choice $P_{emp+R2*}$ for structures like CN.

Figure 10:
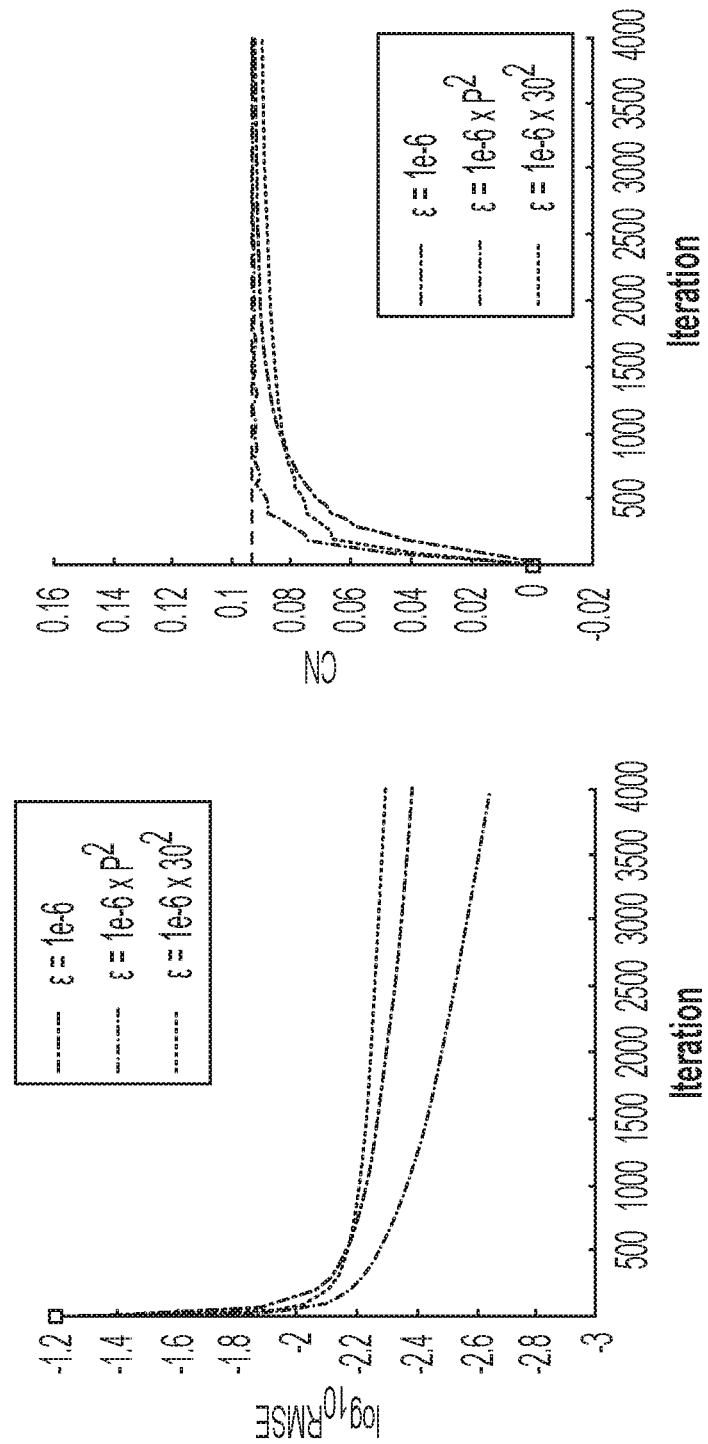
FIG. 10. Simulation result of non-ICH TFI using $P_{emp+R2*}$. Using a globally increased $\in=10^{-6} \times 30^2$ for numerical conditioning improves the RMSE for the first 600 CG iterations, at the cost of eventually increasing the RMSE and enlarging the bias in CN measurement (true value as the red dashed line). In contrast, using preconditioner as a spatially adaptive scaling for $\in=10^{-6} \times P^2$, achieves both lower RMSE and less deviations for ROI measurement compared to the default $\in=10^{-6}$, without introducing bias to the CN measurement.

In this work, the numerical conditioning parameter ∈ was scaled with the preconditioner which assigned higher weights for strong susceptibility sources. To assess its effect on the reconstruction performance, TFI with $P_{emp+R2*}$ was repeated with three ∈ choices: $\epsilon=10^{-6}$, $\epsilon=P^2\times10^{-6}$ (proposed) and $\epsilon=30^2\times10^{-6}$. FIG. 10 showed that: $\epsilon=10^{-6}\times30^2$ achieved lower RMSE than $\epsilon=10^{-6}$ for the first 600 CG iterations, but ended up with higher RMSE and larger bias in CN measurement at $4000^{th}$ CG. There is a tradeoff of converging speed and accuracy was observed for a globally uniform ∈. Meanwhile, $\epsilon=10^{-6}\times P^2$ consistently improved convergence of TFI in terms of lower RMSE and less deviation in CN measurement until $4000^{th}$ CG, in comparison to those of $\epsilon=10^{-6}$. To understand this, the inventors looked at different stages of GNCG in the presence of a non-uniform ∈. At early iterations where solution $\chi$ is close to 0, the inventors have $\sqrt{|M_G\nabla\chi|^2+\epsilon}\approx\epsilon^{0.5}$, then the notion of numerical conditioning ∈ is closely related to an $L_2$ regularization $$\frac{1}{\epsilon^{0.5}}|M_G\nabla\chi|_2^2.$$

This suggests that scaling ∈ with the preconditioner is essentially applying different regularization level for voxels with different susceptibility magnitude at early stage of GNCG. On the other hand, since this scaling is mostly significant at strong susceptibility sources (P≫1) which consists only a small portion of the object, it didn't introduce noticeable bias to the eventual susceptibility estimation (CN: 92.34 ppb for $\epsilon=10^{-6}$, 92.53 ppb for $\epsilon=P^2\times10^{-6}$ and 89.94 ppb for $\epsilon=30^2\times10^{-6}$ at $4000^{th}$ CG), as shown in FIG. 10.

Figure 7:
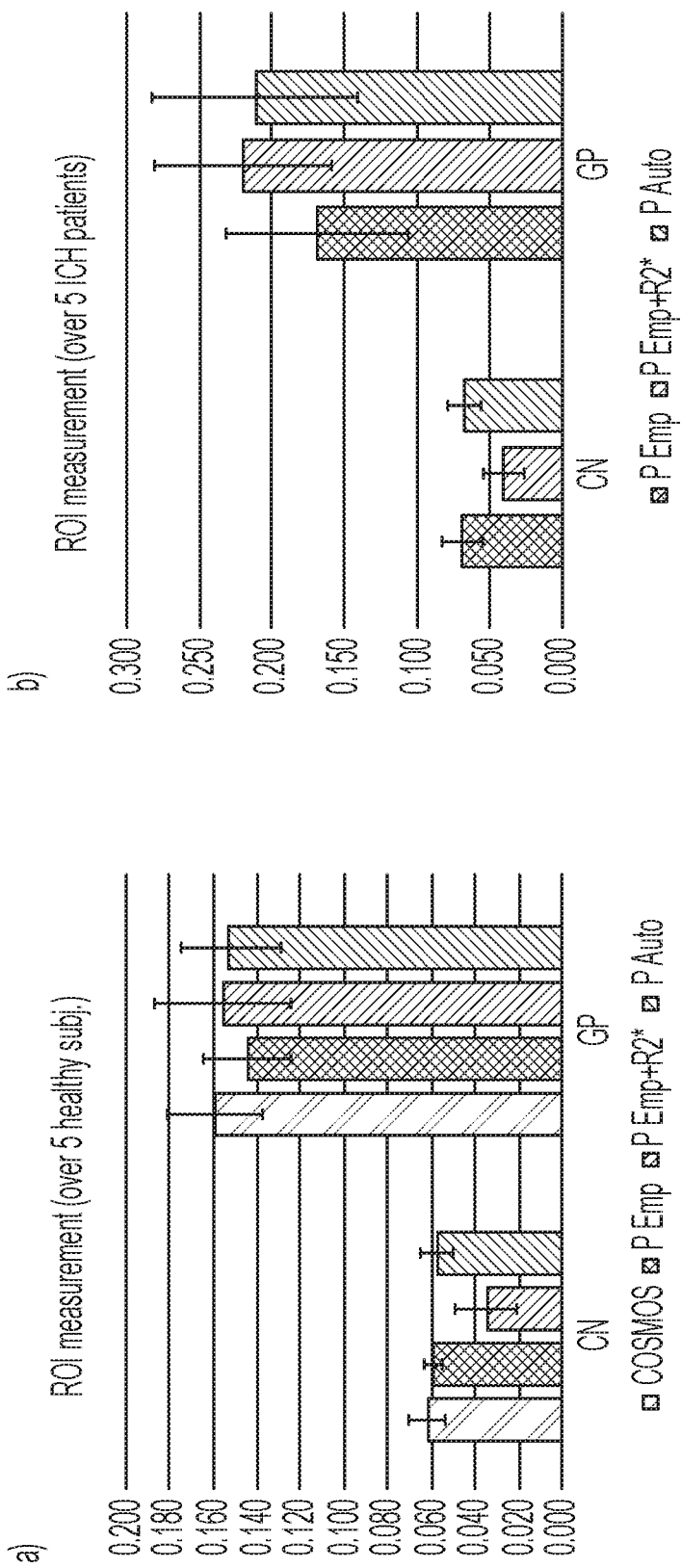
FIG. 7. ROI measurements averaged over 5 healthy subjects (left) and 5 ICH patients (right), respectively, for CN and GP. Underestimation was found in $P_{emp+R2*}$ in measuring CN, compared to $P_{emp}$ and $P_{auto}$. For GP, $P_{emp}$ gave significant under-estimation for GP in ICH patients compared to $P_{auto}$ and $P_{emp+R2*}$.

The proposed automatic preconditioner construction method is readily applicable to QSM problem outside the head. The previous empirical choice requires a new search for preconditioning weights for each anatomy and application. This is avoided in the proposed method, which achieves lower reconstruction RMSE (FIGS. 3a and 3b) and reliable ROI measurement (FIG. 7a). When applied to cardiac QSM, the proposed $P_{auto}$ produces reasonable estimation for LV-RV oxygenation level difference (18.5%~26.1%), which is more comparable to the reported level 18.8% than the measurement by empirical preconditioner $P_{emp+R2*}$ (5.2%~11.8%).

The current work is still limited in the following aspects, and possible solutions are proposed accordingly for further study: 1) Construction of the preconditioner in Eq. 6 requires R2* information, which is unavailable in single-echo acquisitions. One workaround is to replace the sigmoid function in Eq.7 with a simple uniform value which can be the median or mean over all absolute susceptibilities inside M, although an inferior ability to suppress ICH-related artifact is expected. An alternative solution to the absence of R2* might be utilizing other image contrast such as T1w or T2w as the variant in Eq. 5 in place of R2*. 2) The preconditioner construction relies on an approximate map $\chi_{est}$ for the expected susceptibility map. The inventors used PDF and LBV+TKD to estimate sources out- and in-side M, respectively. This rough estimate of susceptibility still contain substantial noise or artifact (e.g. due to low SNR in ICH). One might improve the preconditioner by providing a better estimation $\chi_{est}$ more robust against noise and artifact. For example, the final reconstructed QSM by TFI can be used as $\chi_{est}$ and initiate a new round of TFI reconstruction with the updated preconditioner, at the cost of doubled overall reconstruction time. 3) The skull mask used in this work was determined using a fixed threshold in each case. Automated skull stripping is routinely performed in neuroimaging and could be incorporated here. 4) The performance of the proposed preconditioned method will be assessed on more image content, such as in carotid, musculoskeletal and animal QSM.

In summary, an automated adaptive preconditioner is described for QSM reconstruction, which allows total field inversion without background field removal. The automated adaptive preconditioner adapts to the actual susceptibility content using the total field and R2* derived from the input gradient echo data. The automated preconditioner improves convergence speed and accuracy in reconstruction iteration and produces reliable susceptibility measurement in various diseases, particularly suppressing hemorrhage-associated artifacts while preserving surrounding normal tissue contrast.

2. Quantitative Susceptibility Mapping Using a Deep Learning Prior in Morphology Enabled Dipole Inversion In this section, deep learning based regularization in Bayesian QSM that can provide excellent anatomical details while maintaining accuracy of susceptibility quantification are presented. Artificial neural networks in deep learning, including the convolutional neural networks, can be trained to impose structural consistency between the targeted susceptibility map and known gradient echo image data and to identify the targeted susceptibility map.

2.1. Introduction

Quantitative Susceptibility Mapping (QSM) has been an active research area for its ability to depict magnetic susceptibility, an intrinsic tissue property which is closely related to various pathologies including demyelination, hemorrhage and calcification. At its core, the QSM reconstruction is a Bayesian optimization problem to solve for a susceptibility distribution that is consistent with the tissue inhomogeneity field measurement via dipole convolution, while, due to the ill condition of dipole inversion, promoting a tissue structure prior to suppress streaking and other artifacts. However, explicit regularization is limiting in defining image features in prior knowledge, for example, fine structures like veins may be suppressed due to the intrinsic property of the smoothness or blockiness in common L2 or L1 regularizations.

Recently, convoluted neural network (CNN) in deep learning, which is advantageous in characterizing image features, has been proposed for QSM reconstruction. CNN directly maps the local field to the susceptibility map, hence bypassing the traditional iterative optimization and reducing the computational cost down to a single forward evaluation of the network. The network can be trained on labeled dataset such as healthy subject with COSMOS or numerical phantom, both demonstrating the feasibility of a neural network QSM solution. However, this approach fails to enforce the fidelity between a measured field and its corresponding CNN susceptibility output, and this failure may be substantial when applied on a different population from those used for training.

In this work, the inventors imposed data fidelity in CNN based QSM reconstruction by combining traditional optimization reconstruction with the CNN reconstruction: the output of CNN trained to map from field to QSM is incorporated into the cost function as a Bayesian prior in the QSM optimization problem. Preliminary results show QSM improvements by this fidelity and CNN combined approach.

2.2. Theory

The fundamental inverse problem in QSM reconstruction is to obtain a susceptibility distribution $\chi$ from the measured tissue field f. Given a sample dataset where susceptibility is known, a neural network $\phi(\bullet)$ can be trained to simulate the inversion process, or namely, to learn the mapping from field to susceptibility:

$$\chi_\phi = \phi(f) \quad [11]$$

However, this network does not consider the fidelity between a new measured field f and the network output. In this work, the inventors employed a Bayesian reconstruction framework (9,10) incorporating the neural network outcome into the optimization problem:

$$\chi^* = \operatorname*{argmin}_\chi \frac{1}{2} \|w(d*\chi - f)\|_2^2 + \lambda_2 \|E(\chi - \chi_\phi)\|_2^2 \quad [12]$$

The first term is the data fidelity penalty as in the traditional QSM reconstruction, with w the noise weighting and d the dipole kernel. The second term is an L2-regularization to impose a desired structural similarity or to penalize the discrepancy between $\chi$ and the estimated map $\chi_\phi$ given by the network $\phi$. Here, E is a linear transformation, which can be identity or a filter that enhance specific spectrums in the solution. The design of E will be explained in the Method section.

The Bayesian rational of this L2-regularization is a prior that $E_\chi$ belongs to an i.i.d. Gaussian $\mathcal{N}(E\chi_\phi, \lambda_2^{-1})$ at each voxel. A similar Bayesian framework can be found in Morphology Enabled Dipole Inversion (MEDI):

$$\chi^* = \operatorname*{argmin}_\chi \frac{1}{2} \|w(d*\chi - f)\|_2^2 + \lambda_1 \|M_G \nabla \chi\|_1 \quad [13]$$

where an L1-norm of the image gradients weighted by a binary edge mask $M_G$ is used for regularization. This consists a prior that $M_G \nabla \chi$ should be sparse. Considering the necessity of zero-referencing for susceptibility quantification, an extra L2 regularization can enforce a consistent CSF as used in MEDI+0:

$$\chi^* = \operatorname*{argmin}_\chi \frac{1}{2}\|w(d*\chi - f)\|_2^2 + \lambda_1\|M_G\nabla\chi\|_1 + \lambda_{CSF}\|M_{CSF}(\chi - \overline{\chi_{CSF}})\|_2^2 \quad [14]$$

where $M_{CSF}$ is a binary mask for ventricular CSF and $\overline{\chi_{CSF}}$ is the mean susceptibility within it. Similarly, this CSF specific regularization can be added to Eq. 12, leading to the final proposed objective:

$$\chi^* = \operatorname*{argmin}_\chi \frac{1}{2}\|w(d*\chi - f)\|_2^2 + \lambda_2\|E(\chi - \chi_\phi)\|_2^2 + +\lambda_{CSF}\|M_{CSF}(\chi - \overline{\chi_{CSF}})\|_2^2 \quad [15]$$

In this work, the proposed method (Eq. 15) is referred to as MEDI+DL. It will be compared with $\chi_\phi$, the raw outcome of the deep learning network which is referred to as DL, and with MEDI+0 (Eq. 14), which is referred to as MEDI throughout this work for brevity.

2.3. Materials and Methods

All data in this work were acquired using the 3D multi-echo GRE sequence on a 3 T GE scanner (voxel size 0.5×0.5×3 mm³, field of view 24 cm, dTE 0.48 ms, no. of slice 50~60). The matrix size is 512×512×50~60. 20 healthy subjects and 8 patients with multiple sclerosis were scanned, according to an institutional review board approved protocol. Local tissue field was estimated through multi-echo phase fitting, phase unwrapping and background field removal. 4 of the 20 healthy subjects were scanned using the same sequence at voxel size of 1×1×1 mm³ with 5 different orientations to perform a COSMOS reconstruction for quantitative comparison.

Figure 11:
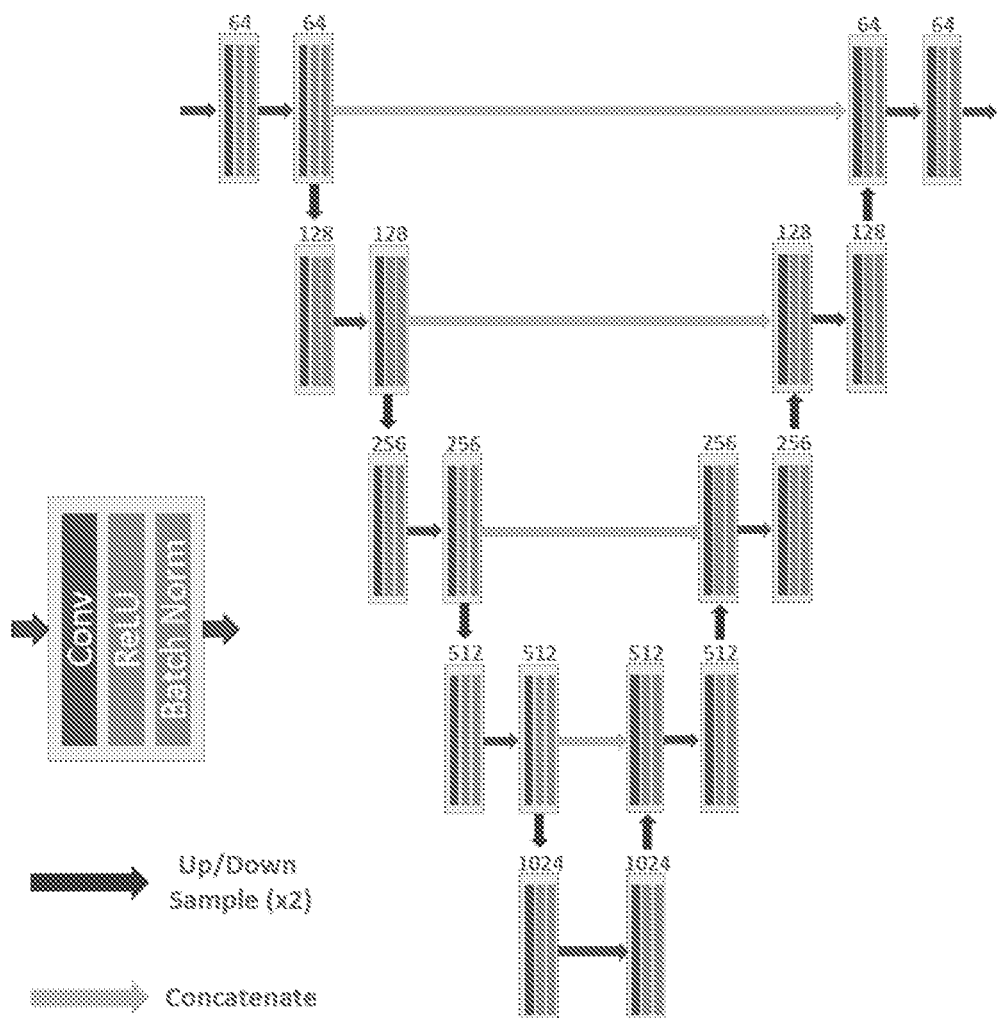
FIG. 11. U-Net structure used in this work. Each convolutional block consists of a 3D convolution layer (kernel 3×3×3), a ReLU activation and a Batch Normalization layer. The number of output feature is denoted above each block. Max pooling is used for down-sampling.

Neural network setup. U-Net, a fully convolutional neural network, was chosen as the example network structure. An example 3×3×3 kernel, 1 voxel stride and reflective padding were used at each convolution layer. The detailed structure regarding layer number, up/down-sampling factor and feature dimension are shown in FIG. 11. The network was designed an input/output patch at size 128×128×24, while the original 3D volume field map was segmented into patches using a scheme of 66% overlapping between adjacent patches. The output patches were compiled to recover the full volume.

The network was trained on 20 healthy subjects with local field as the input and QSM as the output. 4199 patches were extracted from all 20 cases. The target QSM was reconstructed using MEDI. The training/validation/test split was 0.7/0.1/0.2. L1-norm of the difference map between estimated QSM and ground truth MEDI was chosen as the training loss. Adam optimizer (learning rate 0.001, max epoch 80) was employed for optimizing the loss during training. This work was implemented on a platform with Core i7 CPU, 128 GB memory and 4 GTX TITAN XP GPUs (12 GB each).

Iterative reconstruction: MEDI+DL. The DL outcome, $\chi_\phi$, estimated by the network, was plugged into Eq. 15 in the format of an L2 regularization. A high-pass-filter was proposed as the linear transform E prior to the penalization, as implemented by convolution with a spherical kernel S: $E(\chi)=\chi-S*\chi$. The penalization would be emphasized upon high frequency components in the difference $\chi-\chi_\phi$. The rationale was that since the example neural network was patched-based, spatial variations beyond the extent of a single patch could not be captured by the network. Therefore, by high-pass-filtering the difference map, the regularization allowed the existence of smooth variation across the scope. The radius of S was chosen as 10 mm.

Figure 12:
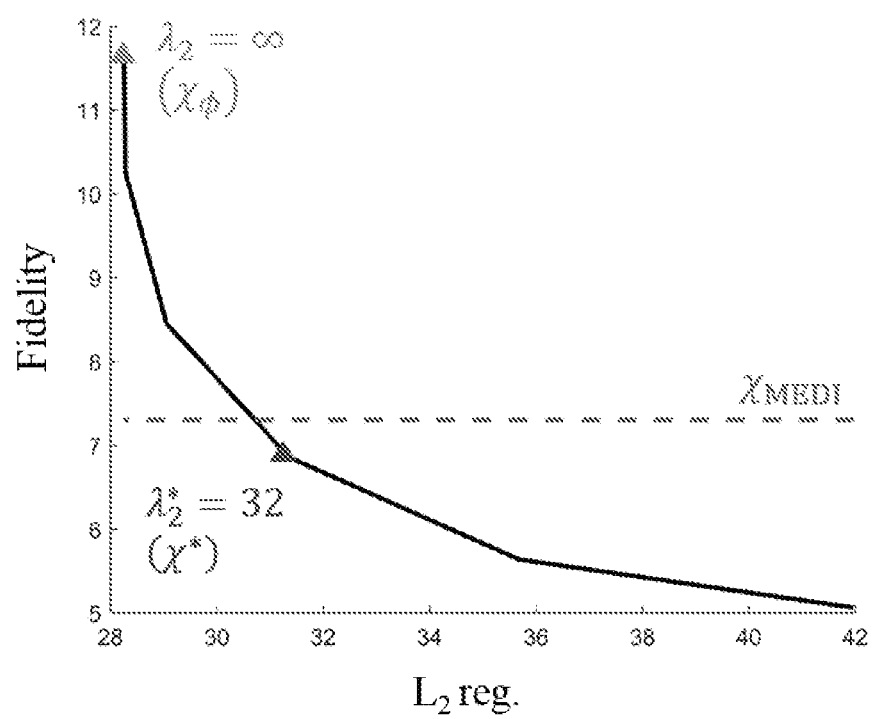
FIG. 12. L-curve for choosing $\lambda_2$. $\lambda_2=32$ is picked (blue triangle) as the maximum value which gives a lower fidelity cost than that of MEDI (red dotted line). Note that $\lambda_2=\infty$ corresponds to a solution same as the raw outcome from the network, $\lambda_\phi$.

MEDI+DL (Eq. 15) was minimized using quasi Newton method with conjugate gradient. An L-curve (see FIG. 12) was used to determine the regularization strength $\lambda_2=32$, which is the maximum value achieving a lower fidelity cost compared to MEDI. MEDI+DL was performed on 4 healthy subjects, which were separated from the training, and on 8 MS patients. For comparison, MEDI (Eq. 14) was performed with $\lambda_1=0.001$ and $\lambda_{CSF}=0.1$.

Quantitative analysis. For both healthy and patient subjects, regions of three major subcortical gray matters (SGM): globus pallidus (GP), putamen (PU) and caudate nucleus (CN), were manually segmented, and the mean susceptibilities were measured within each segmented region. Besides, susceptibilities of multiple sclerosis lesion were measured within manually drawn ROI on each MS patient, in reference to the normal appearing white matter on the mirror side of the brain. The agreement of measurements between different methods were quantified using linear regression and Bland-Altman analysis.

2.4. Results

Figure 13:
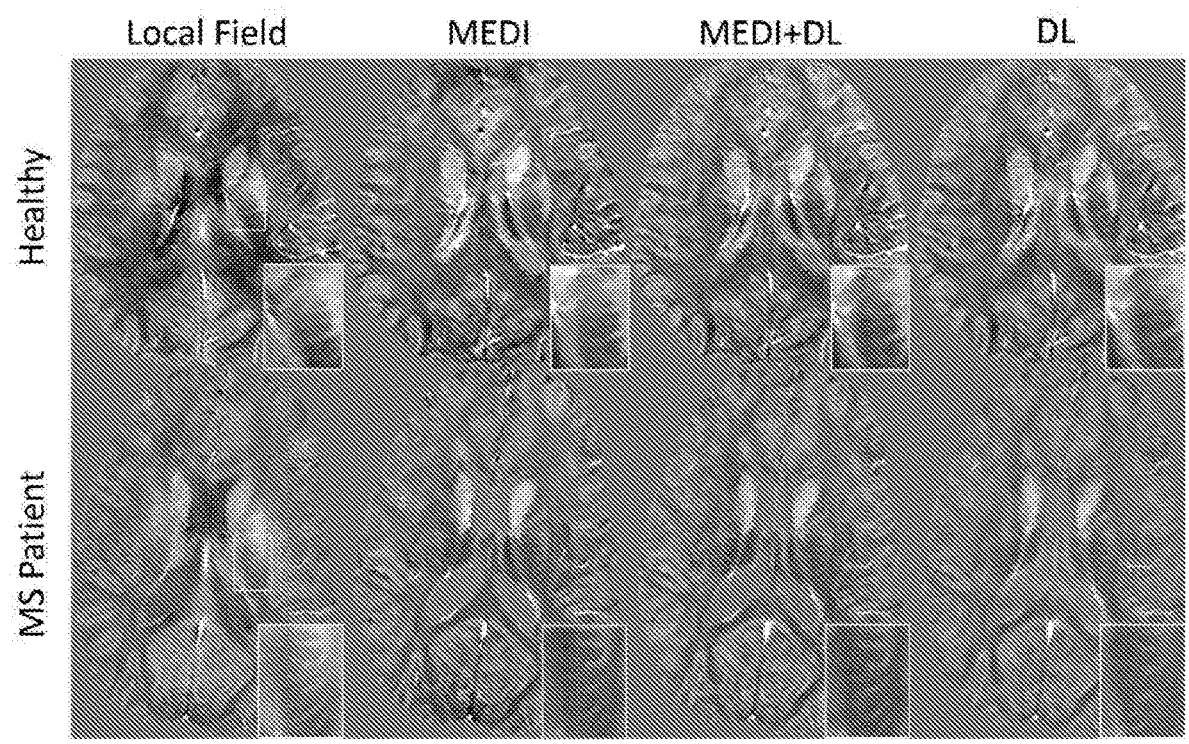
FIG. 13. One example axial slice from a healthy subject (top) and an MS patient (bottom). From left to right: local field, QSM reconstructed by MEDI, MEDI+DL and DL, respectively. MEDI+DL shows superior contrast of vein structures compared to MEDI or DL, such as in the zoomed regions. The structures are also present on the local field.

Healthy subjects. QSM reconstruction for one example healthy subject was shown in FIG. 13 (top row). Compared to MEDI or DL, MEDI+DL demonstrated the veins more distinctly, as highlighted by the yellow boxes in FIG. 13. The same structures were also discernable in the local field (FIG. 13, left column).

Figure 14:
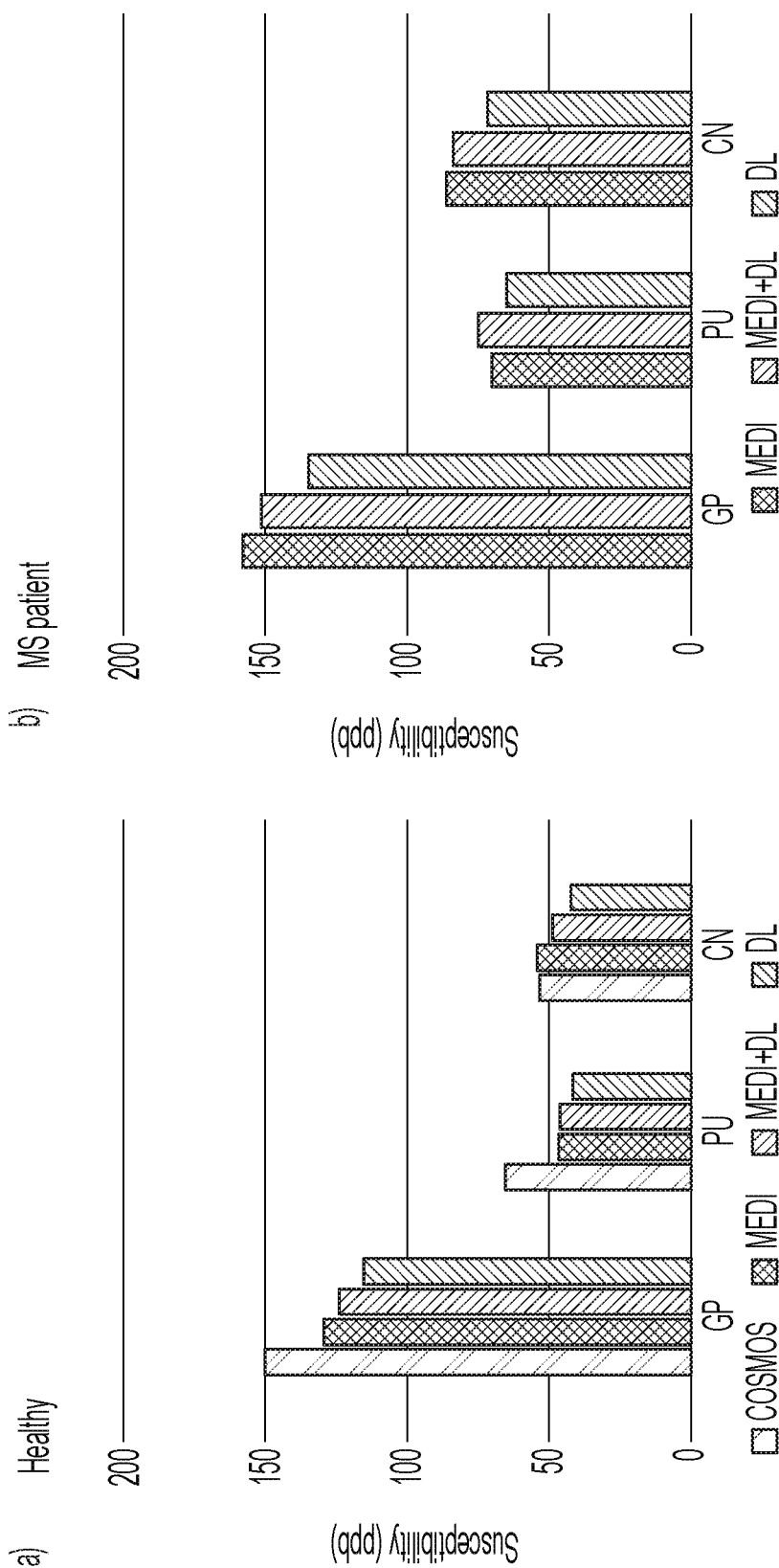
FIG. 14. ROI measurement of GP, PU and CN on QSMs produced by MEDI, DL and MEDI+DL for healthy subject (a) and MS patient (b), respectively. For healthy subject, COSMOS measurements are also provided. Values shown here are averaged over all subjects within each group. MEDI and MEDI+DL produce similar results, while DL has underestimation compared to MEDI and MEDI+DL.

The ROI measurements for SGM can be found in FIG. 14a. Compared to MEDI, the averaged susceptibility measurement suggested a difference of −5 ppb (GP), 1 ppb (PU), −5 ppb (CN) for MEDI+DL, and −13 ppb (GP), −4 ppb (PU), −12 ppb (GP) for DL. Compared to COSMOS, the relative susceptibility difference is −14% (GP), −30% (PU), 3% (CN) for MEDI, −23% (GP), −36% (PU), −20% (CN) for DL, and −17% (GP), −29% (PU), −7% (CN) for MEDI+DL.

Averaged reconstruction time was 95 seconds for MEDI, 2 seconds for DL and 30 seconds for MEDI+DL (excluding network inference time).

Averaged fidelity cost (normalized) was 0.52% for MEDI, 0.86% for DL and 0.50% for MEDI+DL.

MS patients. QSM from one MS patient was shown in FIG. 13 (bottom row). Veins close to corpus callosum were better depicted using MEDI+DL, compared to those using MEDI or DL.

ROI measurement of SGM can be found in FIG. 14b. It showed the averaged susceptibility measurement over 8 patients, indicating a difference of 23 ppb (GP), −7 ppb (PU), −15 ppb (CN) for DL and −6 ppb (GP), 3 ppb (PU), −2 ppb (CN) for MEDI+DL, compared to MEDI.

Figure 15:
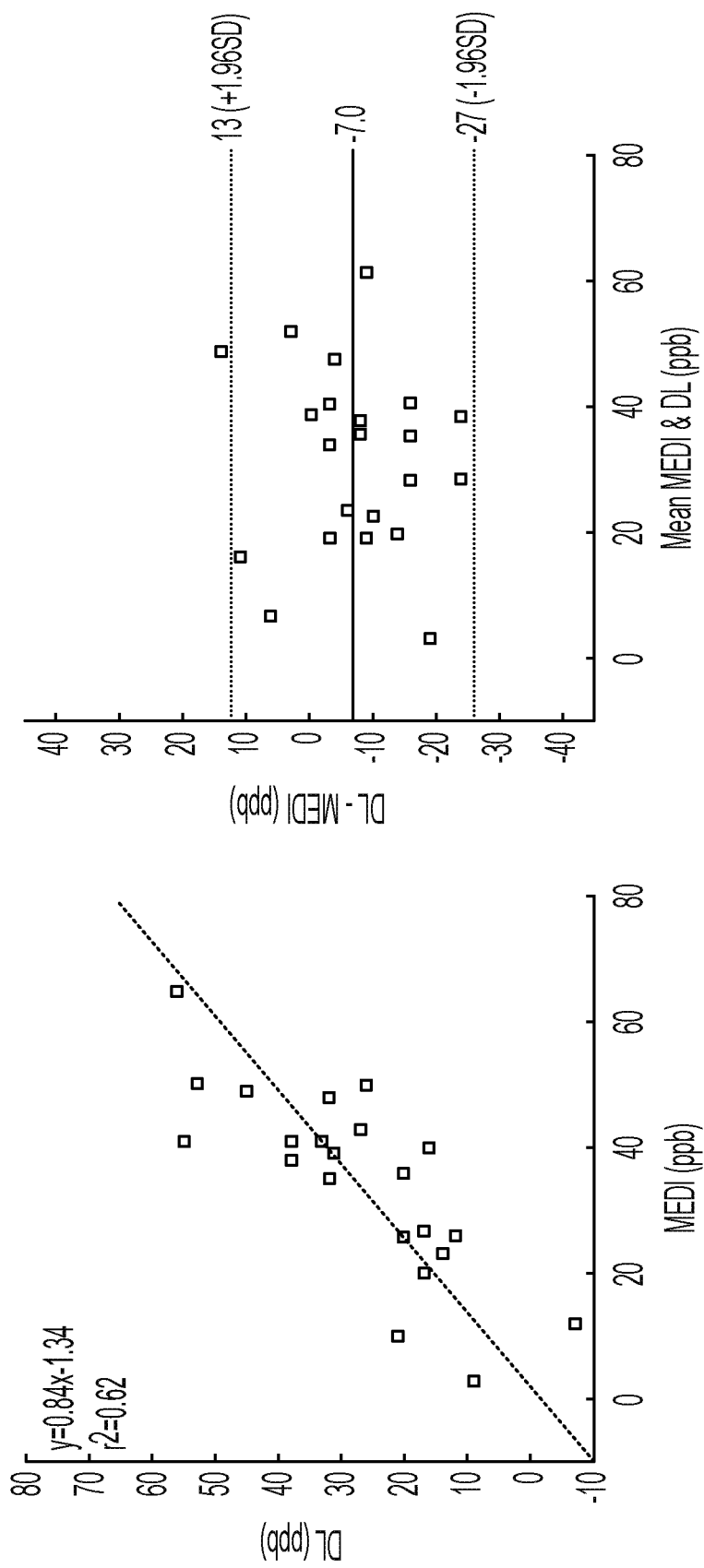
FIG. 15. Linear regression and Bland-Altman plot for MS lesion measurement between MEDI and DL (a) and between MEDI and MEDI+DL (b). MEDI and MEDI+DL have a higher correlation, a smaller bias and narrower limits of agreement.
Figure 15:
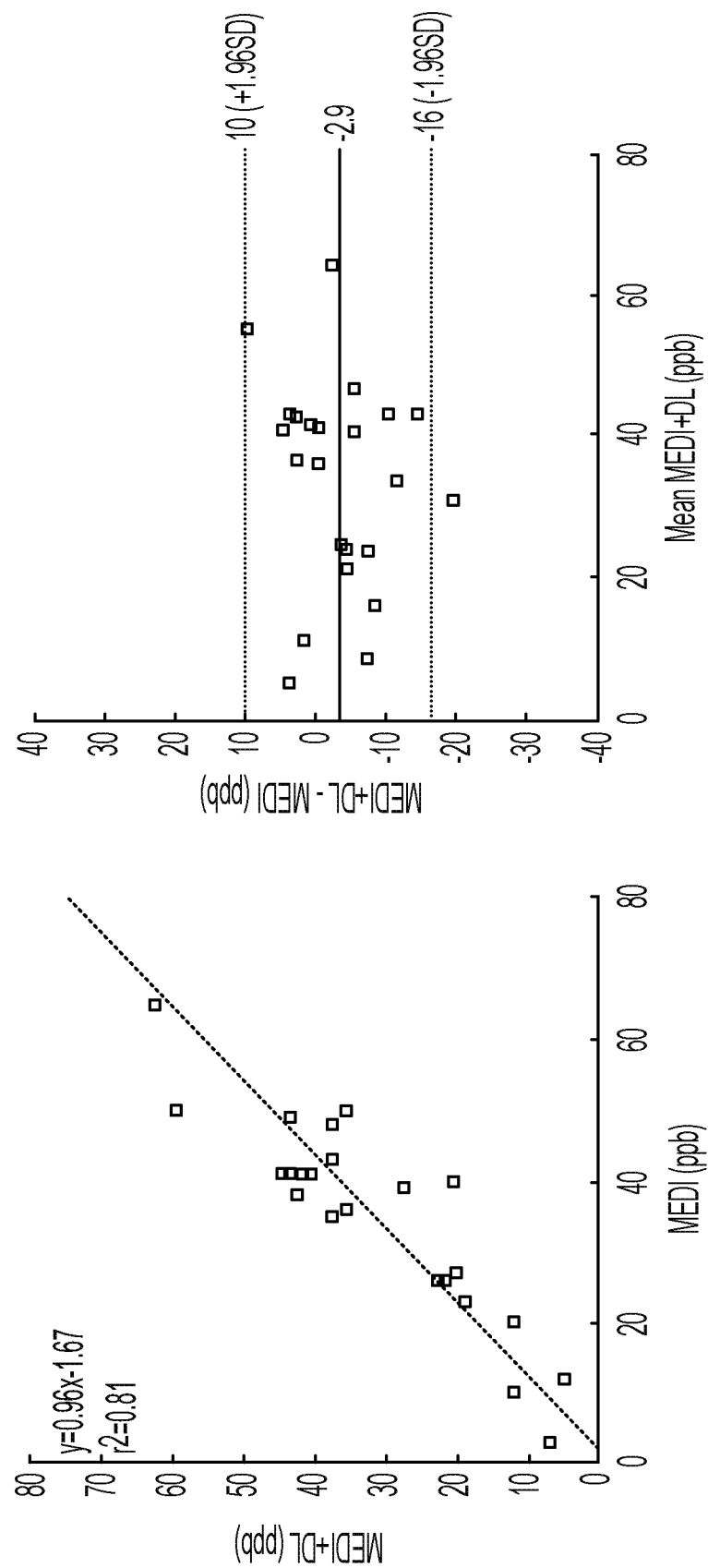

Linear regression and Bland-Altman plot for MS lesion measurement were shown in FIG. 15. The measurements between MEDI and MEDI+DL showed better correlation ($R^2=0.81$) than those between MEDI and DL ($R^2=0.62$). Besides, Bland-Altman analysis indicated narrower limits of agreement [−16, 10] ppb between MEDI and MEDI+DL, compared to [−27, 13] ppb between MEDI and DL.

Averaged reconstruction time was 112 seconds for MEDI, 3 seconds for DL and 41 seconds for MEDI+DL (excluding network inference time).

Fidelity cost (normalized) was 1.56% for MEDI, 1.84% for DL and 1.55% for MEDI+DL.

2.5. Conclusions

The data demonstrated that QSM reconstruction based on incorporating deep learning (DL) neural network output into the Bayesian optimization reconstruction can provide superior contrasts and reduce fidelity cost compared to DL alone and traditional Bayesian optimization. DL alone suffers substantial fidelity cost, which can be reduced by imposing data fidelity through Bayesian optimization.

Traditional Bayesian QSM reconstruction consists of a fidelity term with the measured data, and one or more regularization terms penalizing any deviation from a prior knowledge of susceptibility distribution. Typically, the regularization is expressed in terms of L1 and L2 terms, which are known to have limitations. An L2-regularization on gradient promotes a smooth solution, and an L1-regularization on gradient, also known as the total variation, promotes a piece-wise constant solution or blockiness. Consequently, the total variation term, as used in MEDI (Eq. 14), can suppress subtle structure like small veins close to corpus callosum (FIG. 13). These limitations of traditional regularizations Bayesian MRI reconstruction may be addressed with a deep convolution neural network based regularization, as deep learning outperforms traditional methods in defining subtle image features. We employ this framework of deep learning plus Bayesian optimization in the QSM inverse problem, utilizing the neural network to produce an estimate of susceptibility map and guides the optimization by penalizing the L2 difference between the solution and this network-estimated map. The MEDI+DL proposed by the inventors was shown to produce better visualization of the small veins compared to MEDI. Meanwhile, MEDI+DL takes only ~30% of the time cost of MEDI, because the computationally expensive total variation in Eq. 14 is replaced with the L2 regularization in Eq. 15.

DL neural network for image processing is fast and can resolve complex non-linear mapping across domains, as demonstrated in denoising, super-resolution, segmentation and reconstruction problems. The example network employed a network architecture where feed-forward 3D convolutional neural networks are used to perform the direct transform from tissue field to susceptibility map. However, in previous work, the fidelity to the measured data was not considered. In this work, the inventors evaluated the necessity of the fidelity by pairing the neural network with a fidelity cost in a numerical optimization framework. As demonstrated here, DL's fidelity cost is much higher than MEDI, meanwhile MEDI+DL achieves a lower fidelity cost than MEDI.

Compared to COSMOS, which may be reasonable reference standard without regularization, DL substantially underestimates susceptibility, and MEDI+DL reduces this underestimation as demonstrated in the inventor's deep gray ROI measurements. MEDI+DL and MEDI provide similar susceptibility measurements in deep gray matter and in multiple sclerosis lesions. However, the following subtle puzzle remains to be investigated: while MEDI+DL had less underestimation than MEDI at Putamen as expected from fidelity cost, MEDI+DL had more underestimation than MEDI at globus pallidus and caudate nucleus.

Instead of training a cascaded network to simulate a dedicated iterative projection process, a pre-trained network was used to provide $\chi_\phi$ and use an iterative quasi Newton algorithm to solve the target problem (Eq. 15). The Gaussian uncertainty assumption (Eqs. 12&15) can be replaced with a statistical probability distribution estimation. However, fundamentally, this framework still involves explicit formulation of regularization, which forfeits the benefit of deep learning. Future work should include more effective means to incorporate deep learning neural network with traditional Bayesian optimization.

In summary, the inventors proposed a Bayesian method using neural network to regularize the QSM inverse problem. It showed quantitative consistency with a total variation regularized method, and meanwhile, provided superior contrast of anatomical detail at less than half the computation cost.

3. Fidelity Imposed Network Edit (FINE) for Solving Ill-Posed Image Reconstruction In this section is described an example fidelity imposed network edit (FINE) where the network is an artificial neural network in deep learning, including convolutional neural network. A pre-trained prior network's weights in FINE are modified according to the physical model of a test case. The experiments demonstrated that FINE can achieve superior performance in two important inverse problems in neuroimaging: quantitative susceptibility mapping (QSM) and undersampled multi-contrast reconstruction in MRI.

3.1. Introduction

Image reconstruction from noisy and/or incomplete data is often solved with regularization of various forms, which can be formulated in Bayesian inference as a maximum a posteriori (MAP) estimation. Traditionally, these regularizations promote desired properties of explicitly extracted image features, such as image gradients or wavelet coefficients. Deep learning (DL) using a convolution neural network of many layers has demonstrated superior capability in capturing all desired image features than an explicit feature extraction and achieved tremendous success in a wide range of compute vision applications. Recently, DL has been applied to image reconstruction.

The most popular approach is to formulate the problem as supervised learning, where a DL model is first trained on pairs of data and its ground truth image and is then used to directly reconstruct an image from a test data. However, the performance of this supervised DL strongly depends on the similarity between test data and training data. Any, even a small deviation, can often lead to significant errors in reconstruction. For example, if the test case has a certain pathology that was not present in the training data, a DL model may not be able to capture the pathology. This is in part because DL based techniques are agnostic about the underlying physics and do not incorporate the known physical model of the imaging system.

A common approach to combine DL and the physical model of the imaging system is to use the DL model for defining an explicit regularization in the classical Bayesian MAP framework, typically via an L1 or L2 penalization. However, traditional explicit regularization terms are known to offer imperfect feature description and limit image quality in Bayesian reconstruction.

The advantage of DL over explicit feature extractions may come from that an explicit feature expression used during training is buried deep in the many convolution layers through backpropagation. Accordingly, the inventors proposed to incorporate into the DL layers the physical model of test data or data fidelity defined by the discrepancy between the data measurement and the forward model of the targeted image. One method to achieve this approach is to edit the DL network weights via backpropagation according to the data fidelity of a given test data, and the inventors refer to this method as fidelity imposed network edit (FINE). Preliminary FINE results are reported on neuroimaging problems of quantitative susceptibility mapping (QSM) and MRI reconstruction of multiple contrasts from undersampled k-space data.

3.2. Theory

Consider a Linear Forward Problem:

$$y=Ax+n, \qquad [16]$$

where x is the desired image, y the measured data, A the imaging system matrix defined by the known physical model and n noise in the measured data. The Bayesian reconstruction under Gaussian noise is $$\hat{x} = \operatorname*{argmin}_{x} \frac{1}{2}\|W(Ax-y)\|_2^2 + R(x), \qquad [17]$$

where W is the square root of the inverse of the noise covariance matrix, R (x) is a regularization term that characterizes prior knowledge. The L2 term in Eq. 17 is referred to as data fidelity. Eq. 17 can be solved using numerical optimization procedures, such as the quasi-Newton method that iteratively linearizes the problem with each linear problem solved by conjugate gradient method, or the alternating direction method of multipliers. Common choices for R(x) include sparsity enforcement expressed as Total Variation (TV) or the L1 norm in an appropriate wavelet domain. These types of priors are critical for solving the ill-posed inverse problem, but can also limit image quality of the reconstruction, such as exhibiting artificial blockiness.

Fundamentally, regularization promotes desired image features, which may be advantageously performed with deep learning (DL) than with conventional explicit feature extraction. A general data-to-image convolutional neural network $\phi(; \Theta_0)$ with network's weights denoted as $\Theta_0$ can be trained in a supervised fashion based on $\{\alpha_i, \beta_i\}$ pairs, with $\alpha_i$ the ground-truth image for training data $\beta_i$. The weights at each convolutional layer, along with non-linear activation functions, may be regarded as a collection of feature extractors for the desired image reconstruction. The huge number of weights in DL may explain DL's advantage of explicit feature extraction that uses a single or few weights. Though the training data β in general may be different from the test data y in type (sizes, contrasts, etc), one may treat a test data y as the same type as the training data β to generate a DL reconstruction:

$$\hat{x} = \phi(y; \Theta_0) \qquad [18]$$

An example of such an approach applied to solve ill-posed inverse problems is QSMnet, which aims to solve the field-to-susceptibility dipole inversion in QSM.

This supervised DL strategy can perform poorly if there is a mismatch between the test and training data, because it is agnostic about the forward physical model of data generation well defined for the imaging system (Eq.16). Particularly, this lack of data fidelity can result in substantial error in the network output when the measured data deviate markedly in contrasts from the training data. To address this fidelity-lacking problem, it has been proposed to treat the network output in Eq.18 as a regularization in Eq.17 using an L2 form cost to penalize difference between the network output and the final optimized solution:

$$\hat{x} = \underset{x}{\operatorname{argmin}} \frac{1}{2} \|w(Ax - y)\|_2^2 + \lambda \|x - \phi(y; \Theta_0)\|_2^2. \qquad [19]$$

This reconstruction is referred to as DL with L2 regularization (DLL2). The main drawback of this DLL2 approach is the use of the explicit L2 norm, which is known to be limiting and may not be effective in reducing bias in the final solution towards the fixed network outcome $\phi(y; \Theta_0)$ that contains fidelity errors.

To take advantage of DL over explicit feature extraction, it is proposed to embed the data fidelity term deeply in all layers through backpropagation in DL networks. One method to implement this approach for reconstructing a desired image x is to edit the weights in a pre-trained DL network under the guidance of data fidelity for a given test data y. The network $\phi(\bullet; \Theta)$'s weights are initialized with $\Theta_0$ and are edited according to the test data's physical fidelity of the imaging system:

$$\hat{\Theta} = \underset{\Theta}{\operatorname{argmin}} L(y; \Theta) = \|w(A\phi(y; \Theta) - y)\|_2^2. \qquad [20]$$

Then the output of the updated network is the reconstruction of x with both data fidelity and deep learning regularization:

$$\hat{x} = \phi(y; \hat{\Theta}) \qquad [21]$$

This approach is referred to as "fidelity imposed network edit (FINE)" for solving ill-posed inverse problem using deep learning and imaging physics.

3.3. Materials and Methods

Here, FINE was applied to two inverse problems in MRI: QSM and multi-contrast reconstruction. The human subject studies followed an IRB approved protocol.

QSM

First, FINE was applied to QSM, which is ill-posed because of zeroes at the magic angle in the forward dipole kernel. Consequently, streaking artifacts appear in the image domain after un-regularized dipole inversion. Bayesian approach has been widely used to address this issue. One example is the Morphology Enabled Dipole Inversion (MEDI) method, which employs the following cost function:

$$\hat{x} = \underset{x}{\operatorname{argmin}} \frac{1}{2} \|w(d * \chi - f)\|_2^2 + \lambda \|M_G \nabla \chi\|_1 \qquad [22]$$

with χ the susceptibility distribution to solve, f the field measurement, d the dipole kernel. The regularization is a weighted total variation, with ∇ the gradient operator, $M_G$ a binary edge mask determined from magnitude image, which enforces morphological consistency between magnitude and susceptibility.

Data acquisition and pre-processing. MRI was performed on 6 healthy subjects using a 3 T system (GE, Waukesha, WI) with a multi-echo 3D gradient echo (GRE) sequence. Detailed imaging parameters included FA=15, FOV=25.6 cm, TE1=5.0 ms, TR=39 ms, #TE=6, ΔTE=4.6 ms, acquisition matrix=256×256×48, voxel size=1×1×3 mm3, BW=±62.5 kHz. The local tissue field was estimated using non-linear fitting across multi-echo phase data followed by graph-cut based phase unwrapping and background field removal. GRE imaging was repeated at 5 different orientations per subject for COSMOS reconstruction, which was used as the gold standard for brain QSM. Additionally, GRE MRI was performed on 8 patients with multiple sclerosis (MS) and 8 patients with intracerebral hemorrhage (ICH) patients using the same 3 T system with the same sequence at only the standard supine orientation.

Dipole Inversion Network. An example 3D U-Net, a fully convolutional neural network architecture, was implemented for mapping from local tissue field f to COSMOS QSM. Convolutional kernel size was 3×3×3. Detailed network structure was shown in FIG. 11. Five of the 6 healthy subjects were used for training, with augmentation by in-plane rotation of +15°. Each 3D volume data was divided into patches of size 64×64×16 due to memory constraints, giving a total number of 12025 patches. 20% of these patches were randomly chosen as a validation set. The same combination of loss function was employed as in in training the network with Adam optimizer (learning rate $10^{-3}$, epoch 40), resulting a 3D U-Net $\phi(; \Theta_0)$.

Fidelity Imposed Network Edit (FINE). For a given test data, the network weights $\Theta_0$ from the training was used to initialize the weights Θ in the following minimization:

$$\hat{\Theta} = \underset{\Theta}{\operatorname{argmin}} \|W(d * \phi(f; \Theta) - f)\|_2^2 \qquad [23]$$

This minimization essentially fine-tuned the pre-trained dipole inversion network $\phi(f; \Theta)$ to produce an output for a given test field data f that would be consistent with the forward dipole model. Eq. 23 was minimized using Adam (learning rate $10^{-3}$, iterations stop when relative decrease of the loss function between two consecutive epochs reached 0.01). The final reconstruction of the fine-tuned network was $\hat{\chi} = \phi(f; \hat{\Theta})$.

FINE was applied to one healthy test subject (excluded from training), 8 MS patients and 8 ICH patients, respectively. MEDI was performed with λ=0.001 for comparison. As a benchmark, the inventors implemented the following based on Eq. 19:

$$\hat{\chi} = \underset{\chi}{\operatorname{argmin}} \frac{1}{2} \|W(d * \chi - f)\|_2^2 + \lambda_2 \|\chi - \phi(f; \Theta_0)\|_2^2, \qquad [24]$$

where $\lambda_2$ was chosen such that the fidelity cost $\|W(f-d*\chi)\|_2$ was similar to that in MEDI (Eq.22).

Quantitative analysis. Fidelity cost $\|w(f-d*\chi)\|_2$ was calculated for DL, MEDI, DLL2 and FINE, respectively. For the healthy subject, the reconstructed QSM was compared with COSMOS, a widely used QSM reference standard (yet expensive to acquire), in terms of fidelity cost and structural similarity index (SSIM), which is a metric that quantifies image intensity similarity, structural similarity, and contrast similarity between pairs of image patches.

Multi-Contrast Reconstruction

Second, FINE was applied to multi-contrast MRI reconstruction with under-sampled data. In order to accelerate the time-consuming acquisition of certain contrasts, such as T2 weighted (T2w) or T2 Fluid Attenuated Inversion Recovery (T2FLAIR) images, k-space was under-sampled, thus requiring a regularized algorithm to recover images with minimal artifact. To help with this ill-posed problem, a fully sampled image of another contrast, such as T1 weighted (T1W) images, was incorporated to exploit the shared structural information across contrasts. Bayesian inference with the Directional Total Variation (DTV) regularization was for image reconstruction:

$$\hat{u} = \underset{u}{\mathrm{argmin}} \|U\mathcal{F}u - b\|_2^2 + \lambda dTV(u, \gamma) \quad [25]$$

with b the measured under-sampled k-space data, U the binary k-space under-sampling mask, $\mathcal{F}$ the Fourier Transform operator, u the image to be solved (T2w/T2FLAIR), and $\gamma$ the measured reference image (T1w). b and $\gamma$ formed a test data. An anisotropic regularization was penalty to encourage parallel image gradients on T2w/T2FLAIR and T1w image at each voxel.

Data acquisition and pre-processing. T1w, T2w, and T2FLAIR axial images of 237 patients with multiple sclerosis diseases, with 256×176 matrix size and 1 mm³ isotropic resolution, were obtained and co-registered. For each contrast, 50 axial 2D image slices from each volume were extracted, giving a total number of 11850 slices. Each slice was normalized to range [0, 1].

Contrast Transfer Network. An example 2D U-Net was employed as the network architecture for mapping from a fully sampled T1w image to a fully sampled T2w image, assuming that T1w and T2w images share common tissue structures but differ in contrast. The network was trained using a 3×3 convolutional kernel (FIG. 11). The $L_1$ difference between the network output and target image was used as the loss function in training the network with Adam optimizer (learning rate initialized as $10^{-3}$, epoch 40). There were 8800/2200/850 samples in the training/validation/test dataset. This training established a U-net $\phi(; \Theta_0)$. Similarly, another 2D U-Net was established for mapping from a fully sampled T1w image to a fully sampled T2FLAIR image.

Fidelity Imposed Network Edit. A test data b for a test subject was obtained by undersampling axial T2w images of the subject by a factor of 4.74 using a sampling pattern of Poisson disk in k-space. Similar to Eq.23, the inventors initialized the network weights $\Theta$ using $\Theta_0$ and update them using the following minimization:

$$\hat{\Theta} = \underset{\Theta}{\mathrm{argmin}} \|U\mathcal{F}\phi(\gamma; \Theta) - b\|_2^2 \quad [26]$$

which was solved using Adam (learning rate $10^{-3}$, iterations stopped when the relative decrease of the loss function between two consecutive epochs reached 0.01). Then FINE reconstruction for the T2w image is the final outcome of the edited network was $$\hat{u} = \phi(\gamma; \hat{\Theta}). \quad [27]$$

Similarly, T2FLAIR images were reconstructed.

FINE reconstruction was compared with DTV using $\lambda=0.001$, and DLL2 where Eq. 19 took the following form $$\hat{u} = \underset{u}{\mathrm{argmin}} \frac{1}{2}\|U\mathcal{F}u - b\|_2^2 + \lambda_2\|u - \phi(\gamma; \Theta_0)\|_2^2, \quad [28]$$

Here, $\lambda_2$ was chosen such that the fidelity cost was similar to that of DTV.

Quantitative analysis. Fidelity cost $$\|U\mathcal{F}u-b\|_2 \quad [29]$$

was also calculated for DTV, DL, DLL2. SSIM was also calculated to quantify the similarity between the reconstructed image and the ground truth.

3.4. Results

The results are organized according Edits of network weights, QSM and multi contrast reconstruction.

Edits of Network Weights

Figure 16:
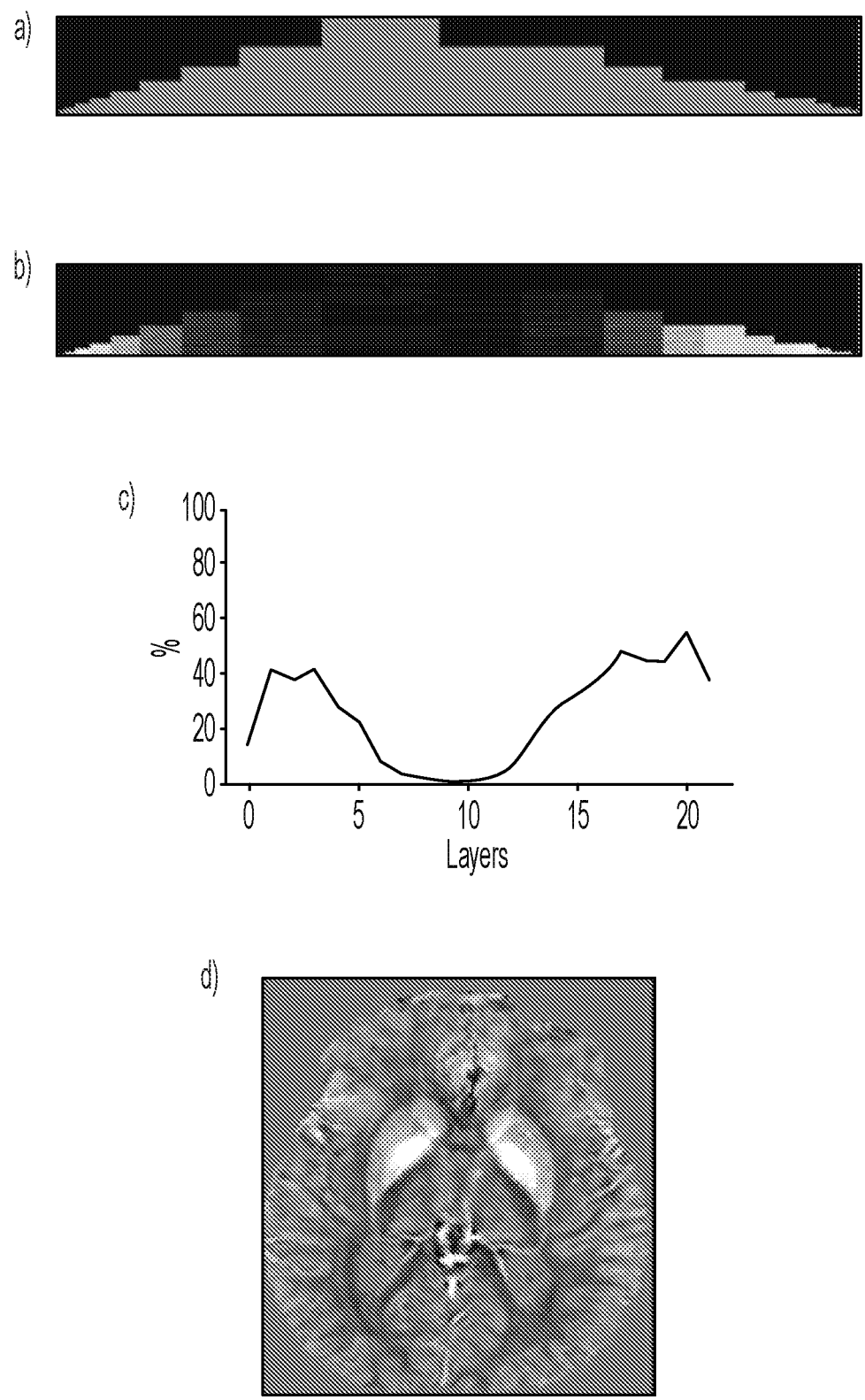
FIG. 16. a): 3D U-Net's weights for each layer before FINE. From left to right: U-Net layers from down-sampling to up-sampling with each square representing weights from a layer in FIG. 11. Weight seems to be fairly uniform over all kernels and layers from pre-training. b): Weight change in absolute value after FINE. The encoder and decoder parts of U-Net experienced substantial weight change by FINE. c): Portion of weights that experienced relative change above 10% in each layer after FINE. d): Reconstructed QSM after FINE. e): randomize initialization as in deep image prior, and f) corresponding weight change, showing all layers of the U-Net experienced substantial weight change. g) portion of weights that experienced relative change above 10% in each layer after deep prior update. h) reconstructed QSM with deep image prior failed to invert the field to susceptibility source map.
Figure 16:
Figure 16:
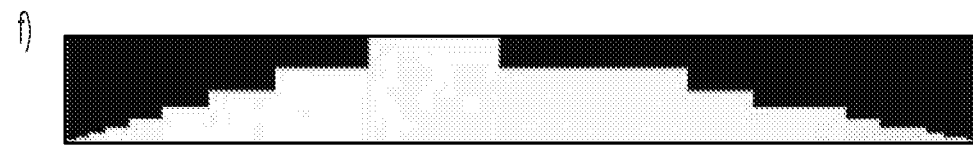
Figure 16:
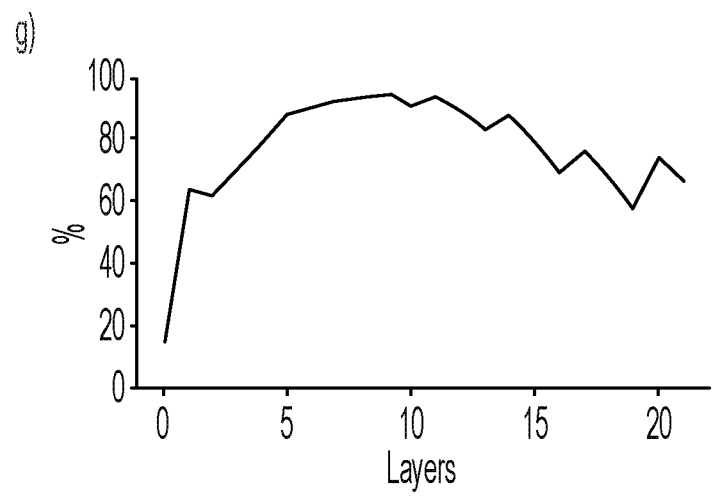
Figure 16:
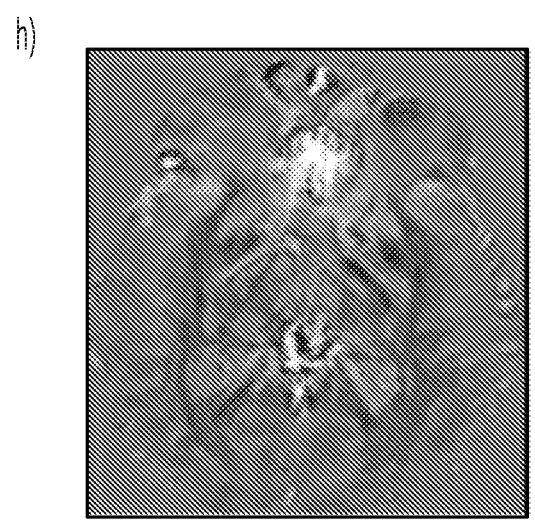

The differences between $\Theta_0$ and $\Theta$ is shown in FIG. 16 for an example case of applying FINE in reconstructing QSM of an MS patient. At pre-training, 3D U-Net's weights $\Theta_0$ were almost uniformly valued along all layers (FIG. 16a). FINE changed substantially the weights in the encoder and decoder parts of the network, but changed $\leq 5\%$ the weights in the middle encoding vector layers (FIG. 16b&c). Compared to FINE, a randomized $\Theta$ initialization in Eq. 20, using a truncated normal distribution (FIG. 16e) centered on 0 with a standard deviation=

$$\sqrt{2/n} \quad [30]$$

with n the number of input units in the weight tensor (deep image prior), caused substantial changes of weights in all layers (FIG. 16f&g) and resulted in markedly inferior QSM (FIG. 16d&h).

QSM

Figure 18:
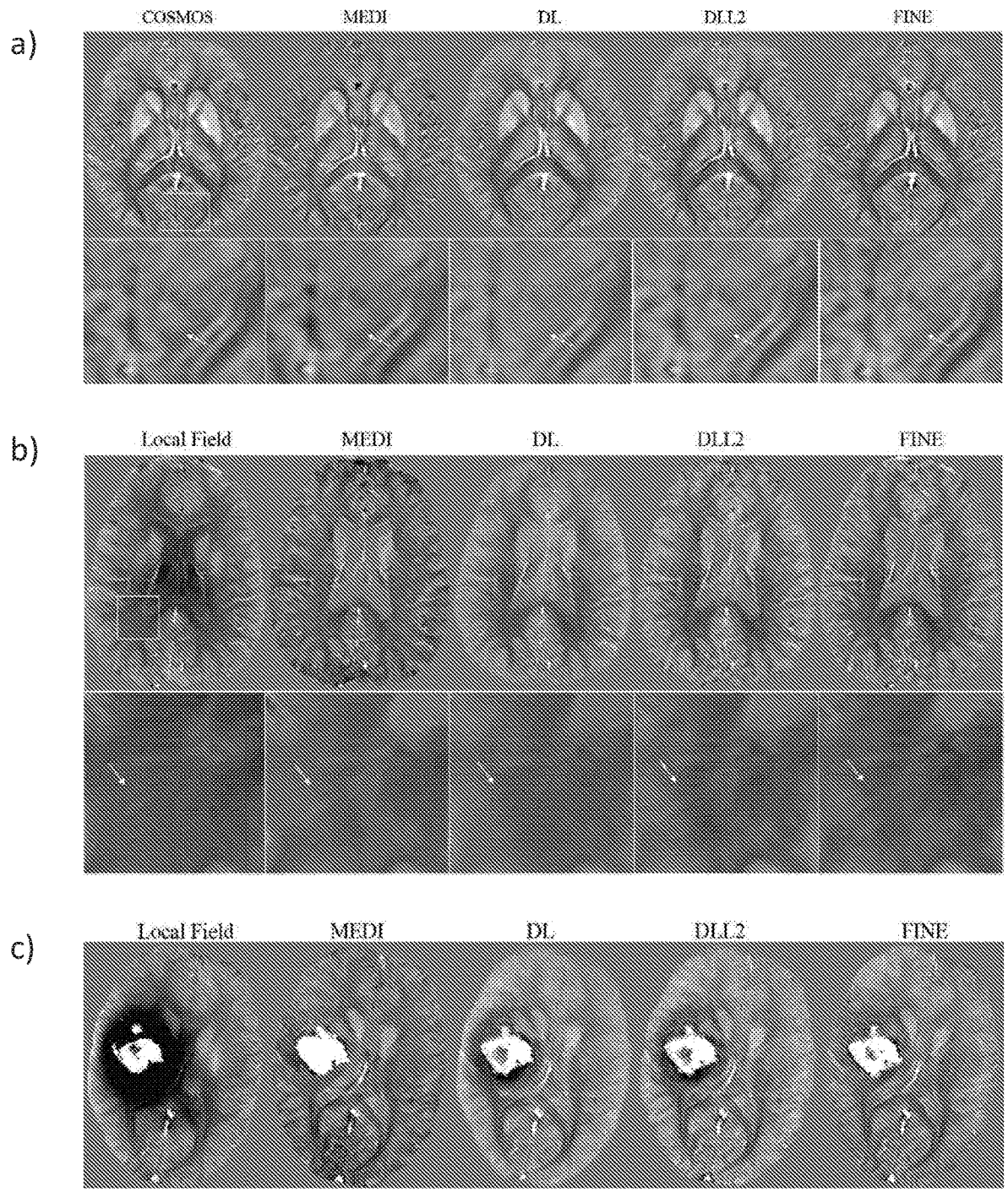
FIG. 18. a) Comparison of QSM of one healthy subject reconstructed by (from left to right) COSMOS, MEDI, DL, DLL2 and FINE. More detailed structures are recovered after fidelity enforcement. Structures in occipital lobe were more clearly depicted in FINE and DLL2 than in MEDI and DL. b) Axial images from a representative MS patient. From left to right: local field, QSM reconstruction by MEDI, DL, DLL2 and FINE, respectively. Central veins near the ventricle were better depicted in FINE and DLL2 than in MEDI or DL. Same structures were discernible on local field as well. c) Axial images from a representative ICH patients. From left to right: Local field, QSM reconstructed by MEDI, DL, DLL2 and FINE, respectively. Hypo-intense artifact was observed close to ICH in DL and DLL2 but suppressed in MEDI and FINE.

Healthy subject. QSMs reconstructed by COSMOS, MEDI, DL, DLL2 and FINE are displayed in FIGS. 17&18. Structures in occipital lobe (zoomed region in FIG. 18a) were clearly depicted in FINE and DLL2 reconstructions, but more blurred in MEDI and DL. Fidelity cost and SSIM in this case are shown in FIG. 17a, with FINE demonstrating the best performance (smallest fidelity cost and largest SSIM).

MS patients. QSMs reconstructed by MEDI, DL, DLL2 and FINE for two representative MS patients are displayed in FIG. 18b. The fine structure of central veins near the ventricle (zoomed region in FIG. 18b) was shown more clearly on FINE and DLL2, compared to MEDI or DL.

ICH patients. QSMs reconstructed by MEDI, DL, DLL2 and FINE are displayed in FIG. 18c. Severe shadow artifact were observed in DL and DLL2. These artifacts were markedly suppressed in MEDI and FINE.

Multi Contrast Reconstruction

Figure 19:
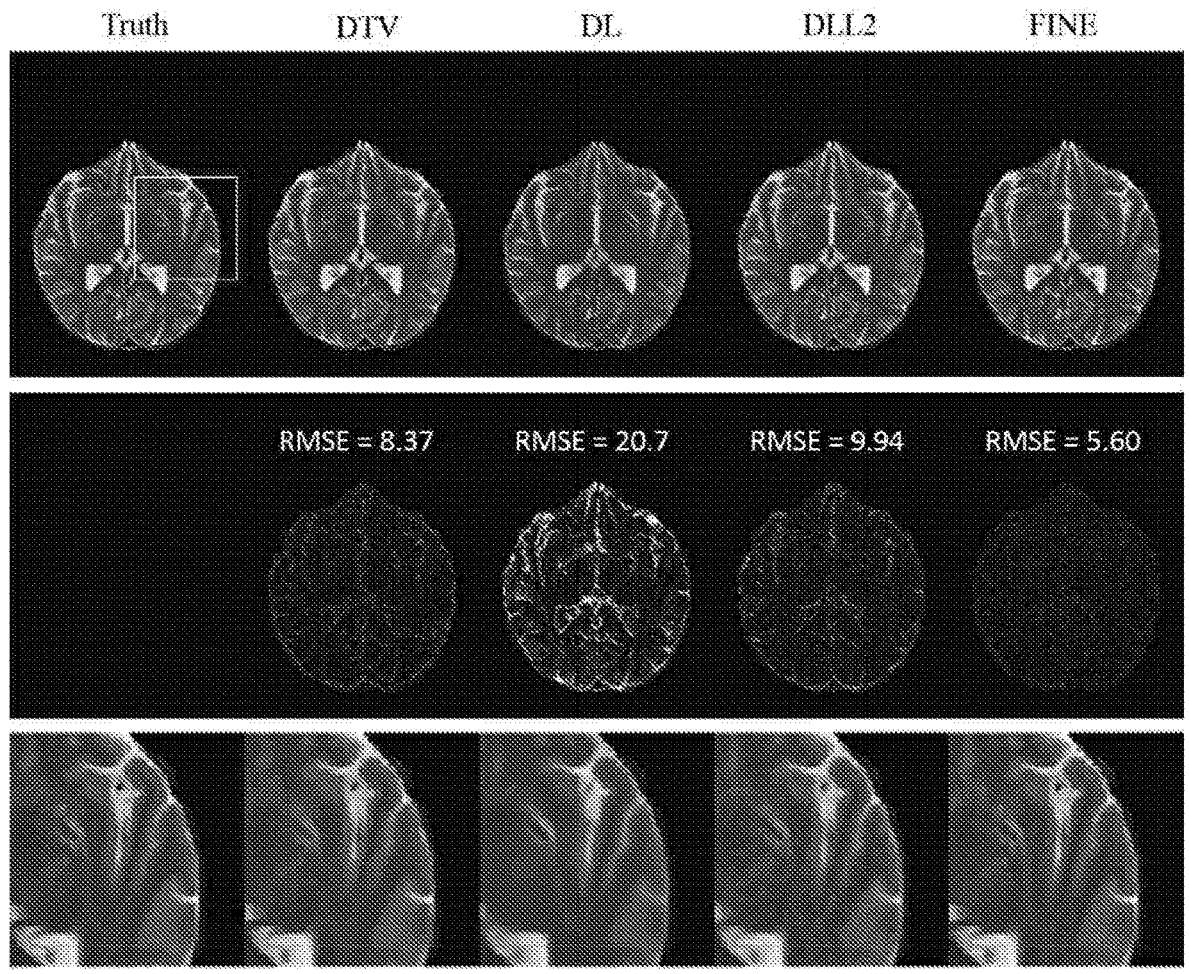
FIG. 19. Comparison of T2w reconstructions. From left to right: fully sampled ground truth, under-sampled k-space reconstruction by DTV, DL, DLL2 and FINE, respectively. First row: reconstructed image. Second row: magnitude of reconstruction error with respect to truth. Third row: zoom-in images. FINE provided a clear recovery at white/grey border, while DTV and DL suffered from over-smoothing and DLL2 suffered from noise.
Figure 20:
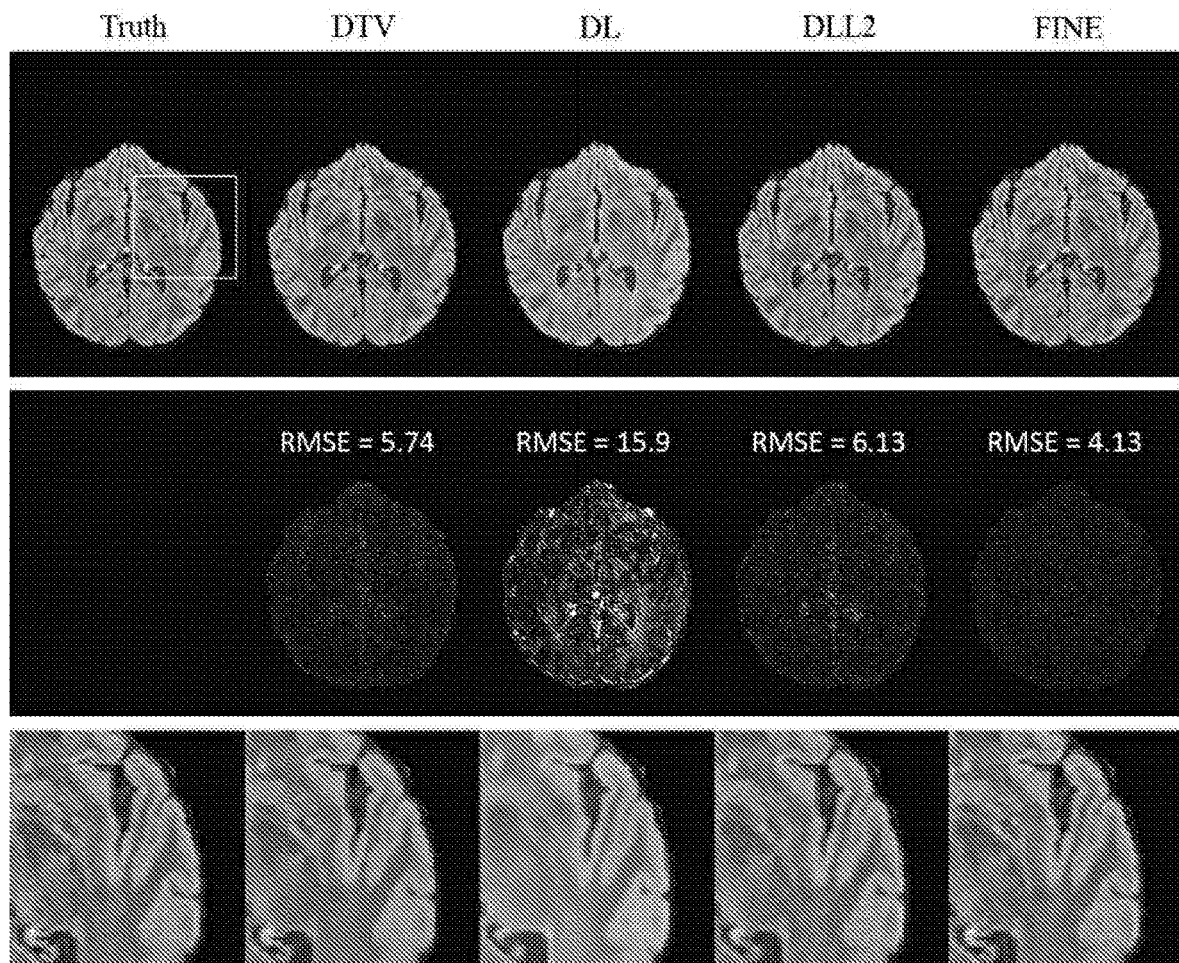
FIG. 20. Comparison of T2FLAIR reconstructions. From left to right: fully sampled ground truth, under-sampled k-space reconstruction by DTV, DL, DLL2 and FINE, respectively. First row: reconstructed image. Second row: magnitude of reconstruction error with respect to truth. Third row: zoom-in images. FINE provided a clear recovery at white/grey border, while DTV and DL suffered from over-smoothing and DLL2 suffered from noise.

T2w and T2 FLAIR images reconstructed by DTV, DL, DLL2 and FINE are displayed in FIG. 19 and FIG. 20, respectively. Structural details such as white/grey boundary were blurry in DTV and DL. They were clearly depicted in FINE and DLL2, with DLL2 visually noisier.

Fidelity and SSIM measures were shown in FIG. 17*b*, with FINE demonstrating the best performance.

3.5. Conclusion

The results indicate that the proposed approach of fidelity imposed network edit (FINE) can be very effective for solving ill-posed inverse problems in medical image reconstruction. FINE embeds the desired physical model of a test data in the many layers of a deep learning (DL) network optimized through backpropagation. Therefore, FINE realizes a faithful use of DL as an implicit regularization in constraining the output manifold of the DL network and offers benefits over the traditional explicit regularization in Bayesian reconstruction of ill-posed inverse problems. Compared with traditional total variation (TV) regularization, DL and a DL based L2 regularization, FINE demonstrates advantages in recovering subtle anatomy missed in TV and in resolving pathology unencountered in the DL training data.

DL has recently been used to solve inverse problems in medical image reconstruction. A deep neural network (DNN) is often trained to directly map from the data domain to the image domain. For example, DL can be used to map tissue field into QSM. This approach bypasses the typical time-consuming iterative reconstruction in traditional numerical optimization and significantly reduces the reconstruction time (down to a forward pass through the network). However, the fidelity between the reconstructed image and the actual measured data is not considered in this approach. This problem of lacking data fidelity has been recently recognized in DNN image reconstruction. Data fidelity may be approximately encouraged through iterative projections using many convolutional nets. A more precise enforcement of data fidelity is to use the Bayesian framework with an explicit regularization, typically the L2 norm of the difference between the desired image and the network output (DLL2). However, an explicit regularization using the L2 norm or other forms can introduce artifacts in the final reconstructed image and is regarded to be inferior to DL for image feature characterization. In the case of measured data containing a pathological feature markedly deviating from the training data, the bias in the network output might not be effectively compensated. This is exemplified in FIG. 18*c*, where the hemorrhage feature not encountered in training datasets of healthy subjects cannot be properly captured by DL and DLL2. This problem is addressed in the proposed FINE method, where the pre-trained network bias is effectively reduced by updating the network weights guided by the measured data. Compared to DLL2 where only image voxel intensity values are optimized, many more network weights are updated in FINE, which may afford the proposed method more flexibility and greater effectiveness than DLL2.

As QSM needs prior information to execute the ill-posed dipole inversion, seeking a better image feature for regularizing reconstruction has continuously been a major research effort in QSM development. Mathematically, regularization should project out or suppress the streaking artifacts associated with granular noise and shadow artifacts associated with smooth model errors. Streaking artifacts have been effectively reduced using L1-type regularizations, but these techniques suffer from staircasing artifacts or blockiness. Shadow artifacts are yet to be effectively suppressed. These QSM recon challenges may be addressed more effectively using sophisticated and complex image features. DL promises to provide the desired but indescribable complex image features. The FINE implementation of DL reported here may realize the potential of DL for QSM recon.

A related prior work is deep image prior that trains a DL network from scratch on a single dataset for inverse problems of denoising, super-resolution, and inpainting. The work in FIG. 16 showed for QSM recon with the network architecture in FIG. 11 that, deep image prior fails to produce satisfying results and the use of pre-trained weights or FINE is necessary. In FINE, the network is initialized to a pre-trained network, rather than trained from scratch. The empirical analysis indicates that FINE changes predominately the weights of the encoder and decoder parts of the U-Net for the case of QSM reconstruction in an MS patient (FIG. 16), which reflect high spatial frequency contents or details specific to the patient. In view at least of the above, the inventors expect that FINE would provide an effective improvement in other ill-posed inverse problems, such as in image reconstruction, with various DL networks where noisy and/or incomplete data is available and the physical model of data generation is known.

FINE is used to generate desired images from vastly undersampled data of T2 weighted and T2 FLAIR contrasts and structural prior knowledge in terms of network weights trained by corresponding T1 weighted fully sampled data. Similarly, FINE can be extended to generate images from vastly undersampled data of other tissue contrasts including perfusion/diffusion/susceptibility weighting.

In other aspects of the present concepts, FINE may be advantageously applied to a wide range of applications such as, but not limited to, super-resolution and de-noising. The computational cost of FINE is much higher than a single pass through a DL network, due to the additional network updating based on the iterative optimization. The computational cost may be reduced by updating a subset of layers instead of the entire network in the optimization, as in transfer learning.

In summary, data fidelity can be used to update a deep learning network on a single test data in order to produce high quality image reconstructions. This fidelity imposed network edit (FINE) strategy promises to be useful for solving ill-posed inverse problems in medical imaging.

4. Quantitative Transport Mapping

Contrast enhanced MRI is routinely performed in clinical practice. Contrast agents in MRI are highly paramagnetic and can be quantified using QSM. In fact, the QSM invention originated from solving contrast agent quantification in time-resolved contrast enhanced MR angiography. The time resolved map of contrast agent concentration quantified by QSM can be used to study contrast agent or tracer transport in tissue.

In this section is described the inversion from time-resolved imaging of tracers to transport field quantities, which is formulated as an optimization problem and referred to as quantitative transport mapping (QTM). QTM solution for porous vessels is clinically feasible and its velocity map from dynamic contrast enhanced (DCE) MRI data can be used for characterizing transport in tumors.

4.1. Introduction

Currently, quantitative interpretations of time-resolved imaging data of a tracer transport through tissue are based on Kety's equation that requires a global arterial input function (AIF) to all local tissues. Kety's equation was originally formulated for tracer mass conservation of an organ with the AIF defined at the main artery supplying the organ. The difficulty that AIF is not measurable at voxel level was recognized in the very first attempt of applying the Kety's equation to time-resolved tomography. The arterial supplies to tissue in a voxel are multiplicate and their characteristics deviate from the global AIF in terms of delays and dispersions. Consequently, flow quantification based on Kety's equation contains errors. Furthermore, identifying an AIF can be difficult and dependent on the operator and the patient.

When considering mass conservation on a voxel level in tomographic imaging, including computed tomography (CT), magnetic resonance imaging (MRI) and positron emission tomography (PET), the 3D distribution of the arterial transport to the voxel of interest should be considered. The transport of a tracer in tissue should naturally be described by the transport equation derived from the first principles of physics. The transport equation uses field quantities of scalars, vectors and tensors to reflect local mass conservation, eliminating the unphysical assumption of a global arterial input when Kety's equation is used. Recently, this transport field equation has been introduced to describe mass conservation observed in tomographic imaging.

A quantitative interpretation of time-resolved imaging of tracers based on the physical transport equation is under development. As discussed below, the inventors report a weak microstructure approximation result on drift velocity mapping. In this approach, the complex intravoxel structure affecting transport processes is approximated as a uniform porous medium to allow setting up a simple forward problem based on the continuity equation. The inverse problem of estimating transport quantities from imaging data can then be solved using alternating direction method of multipliers. Reported below are results from MRI, where the tracer particle concentration is directly estimated from time-resolved contrast-enhanced (DCE) MRI.

4.2. Theory

The transport of molecular particles is governed by the Fokker-Planck transport equation that describes the time evolution of the probability density function of the particles under hydraulic, drag and random forces. In the continuous space of infinite resolution, the Fokker-Planck transport equation can be expressed as $$\partial_t c(r,t) = -\nabla \cdot c(r,t) u(r) + \nabla \cdot D(r) \nabla c(r,t), \quad [31]$$

where c(r, t) is the probability density function that can be interpreted as particle concentration, $\partial_t$ the time derivative, $\nabla$ the three-dimensional spatial derivative, $u(r)=[u^x, u^y, u^z]$ the drift velocity vector field reflecting a particle flux part proportional to concentration, and D (r) the matrix field of diffusion coefficients reflecting a particle flux part proportional to concentration gradient. Both u(r) and D(r) are treated as being constant during the experimental observation. The partial differential equation (PDF) of Eq.31 reflects the local mass conservation and therefore is referred to as the continuity equation. For tomographic imaging experiments, Eq.31 may be modified to account for decay of particles or tracers; for example, arterial spin label in MRI decays at 1/T1 rate and a radioligand in PET decays at ln2/half-life.

The time-resolved tomographic imaging data of tracer concentration can be fitted to Eq.31 for estimating u(r) and D(r) at each voxel, but their computations and interpretations may require microstructure information. Tissue in a voxel may be partitioned into a vascular compartment (v, microvasculature $\Omega_v$, with partial volume v, and concentration $c_v$) defined by microvasculature and an extravascular compartment (e, extravascular space microvasculature $\Omega_e$, with partial volume $v_e$ and concentration $c_e$), with the concentration averaged in a voxel expressed as:

$$\langle c \rangle = v_v c_v + v_e c_e \quad [32]$$

The tracer movement is assumed to be the same as its carrier water. In the v-compartment (water density $\rho_0$), blood flow approximately dominated by drift velocity can be determined by forces including viscosity $\mu = v\rho_0$ and hydraulic pressure p according to the Navier-Stokes equation $$\partial_t u + (u \cdot \nabla) u = -\frac{\nabla p}{\rho_0} + v \nabla^2 u, \forall r \in \Omega_v, \quad [33]$$

assuming incompressible blood flow ($\nabla \cdot u = 0$). While tracers stay in the v-compartment in healthy tissue, they can permeate through the vessel wall into the e-compartment in diseased tissue. The tracer movement in the e-compartment may be approximated as diffusion:

$$\partial_t c_e = \nabla \cdot D \nabla c_e, \forall r \in \Omega_e. \quad [34]$$

The tracer concentration in the two compartments can be connected through the vessel wall permeability ($\psi$) at the boundary ($\partial \Omega_v$, with a surface norm $\hat{n}$) of the v and e compartments, which is the flux through the vessel wall:

$$\psi(c_v - c_e) = (-D_e \nabla c_e) \cdot \hat{n}, \forall r \in \partial \Omega_v. \quad [35]$$

For an image volume with known microvasculature $\Omega_v$, Eqs.32, 34 and 35 can be solved to express compartment concentrations $c_v$, $c_e$ in term of the voxel average concentration $\langle c \rangle$, and Eq.33 can be solved for $u(p, D, \psi; r) \forall r \in \Omega_v$. These solutions can be input into Eq.31 for integration over the volume of a voxel to generate a discrete difference equation. Then, tissue transport parameters p, D, $\psi$ can then be determined by fitting time-resolved imaging data to this difference equation using numerical optimization. This process is referred to herein as the voxelization of the transport equations.

In general, the transport voxelization is quite complex and depends on detailed prior information of tissue composition and vascular structure within the voxel. Eqs.31-35 can be used to generate data pairs between maps of transport parameters p, D, $\psi$ and time resolved images. These data pairs can be used to train artificial neural network, which can then be used to estimate maps of transport parameters p, D, $\psi$ from measured time resolved images.

For this first attempt of transport voxelization to derive a manageable yet reasonable solution, tissue is assumed to be homogeneously porous or to have weak microstructure with little compartmentalization effects. As a zeroth order approximation, this porous tissue model may roughly describe tumor where the vascular wall is porous, blood flow is large, and tracers are freely diffusible. The kinetics of this transport in a porous medium can be approximately described by an average drift velocity over the voxel without any detailed microstructure information. The estimation of kinetic parameter of an average drift velocity only needs fitting data to the continuity equation. This is vastly simplified from the full determination of tissue transport parameters p, D, $\psi$ that requires detailed microstructural information. The inventors define the following discretized derivatives at a voxel $\xi$ for $$c^i(\xi) = c(\xi, t_i): c^i_x(\xi) = \frac{c^i(\xi) - c^i(\xi_x - 1, \xi_y, \xi_z)}{\Delta x},$$

$$c^i_y(\xi) = \frac{c^i(\xi) - c^i(\xi_x, \xi_y - 1, \xi_z)}{\Delta y}, c^i_z(\xi) = \frac{c^i(\xi) - c^i(\xi_x, \xi_y, \xi_z - 1)}{\Delta z},$$

$$c^i_t(\xi) = \frac{c^i(\xi) - c^{i-1}(\xi)}{\Delta t},$$

where $\Delta x$, $\Delta y$, and $\Delta z$ are the voxel dimensions. Then the determination of the average drift velocity can be expressed by fitting data to a simplified continuity equation Eq.31, with a regularization term R (u):

$$u = \arg\min_{u} \sum_{i=2}^{N_t} \frac{1}{2}\|c_t^i + \nabla c^i \cdot u\|_2^2 + \lambda R(u). \quad [36]$$

Here, $\nabla c^i = (c_x^i, c_y^i, c_z^i)$, the discretized spatial derivatives or the gradient of $c^i(x, y, z)$, and $u=[u^x, u^y, u^z]$. For an L1 regularization, $R(u) = \Sigma_{m=x,y,z}\|\nabla u^m\|_1 = \Sigma_{m=x,y,z} \Sigma_{n=x,y,z}\|u_n^m\|_1$, Eq.36 is a LASSO (least absolute shrinkage and selection operation) regression that can be solved efficiently by alternating direction method of multipliers (ADMM). Let $\vec{\varphi} \equiv \{\varphi^m\}_{m=x,y,z}$, $\varphi^m = [\varphi_x^m, \varphi_y^m, \varphi_z^m]$, $\vec{\phi} \equiv \{\phi^m\}_{m=x,y,z}$, $\phi^m = [\phi_x^m, \phi_y^m, \phi_z^m\phi]$, $\vec{u} \equiv \{\nabla u^m\}_{m=x,y,z}$, $\nabla u^m = [u_x^m, u_y^m, u_z^m]$, m=x, y, z, then the augmented Lagrangian for Eq.36 is $$L(u, \varphi, \phi) = \sum_{i=2}^{N_t} \frac{1}{2}\|c_t^i + \nabla c^i \cdot u\|_2^2 + \lambda R_1(\vec{\varphi}) + \frac{\varrho}{2}\|\vec{u} - \vec{\varphi}\|_2^2 + \varrho\langle\vec{\phi}, \vec{u} - \vec{\varphi}\rangle \quad [37]$$

Here $R_1(\vec{\varphi}) = \Sigma_{m=x,y,z} \Sigma_{n=x,y,z}\|\varphi_n^m\|_1$, $\|\vec{u} - \vec{\varphi}\|_2^2 = \Sigma_{m=x,y,z} \Sigma_{n=x,y,z}\|u_n^m - \varphi_n^m\|_2^2$, and $\langle,\vec{\phi}\vec{u} -\rangle = \Sigma_{m=x,y,z} \Sigma_{n=x,y,z} \phi_n^m (u_n^m - \varphi_n^m)$. The ADMM iteration consists of updating u, $\vec{\varphi}$, $\vec{\phi}$ in the following manner:

$$u(k+1) = \arg\min_u L(u, \vec{\varphi}(k), \vec{\phi}(k)): \varrho\Delta u^m - \sum_{n=x,y,z} \mathbb{C}_{m,n} u^n(k+1) = \quad [38]$$
$$c_{t,m} - \varrho\nabla\cdot(\varphi^m(k) - \phi^m(k)),$$
$$m = x, y, z$$

where $\mathbb{C}_{p,q}$ is defined as $\mathbb{C}_{p,q} \equiv \Sigma_{i=2}^{N_t} c_p^i c_q^i$ for p, q=0, x, y, z, t and $c_0^i \equiv c^i$. All multiplications in Eq.38 are pointwise, $\Delta$ is the Laplacian operator, and $\nabla\cdot$ is the divergence operator.

$$\vec{\varphi}(k+1) = \arg\min_{\varphi} L(u(k+1), \vec{\varphi}, \vec{\phi}(k)): \quad [39]$$
$$\varphi^m(k+1) = \mathcal{S}(\nabla u^m(k+1) + \phi^m(k), \lambda/\varrho), m = x, y, z$$

where $\mathcal{S}(a, \kappa) = a - \kappa\cdot\text{sign}(a/\kappa)$ if $|a| > |\kappa|$, 0 otherwise represents soft thresholding. And $\mathcal{S}$ the dual update rule is $$\phi^m(k+1) = \phi^m(k) + \nabla u^m(k+1) - \varphi^m(k+1), m=x,y,z. \quad [40]$$

4.3. Methods and Materials

The proposed QTM was applied to 4D (time resolved 3D) imaging data of dynamic contrast enhanced (DCE) MRI of gadolinium agents passing through tissue. This study was conducted under a HIPAA-compliant IRB-approved protocol for retrospective analysis of MRI data. DCE MRI data of patients with tumors in various organs were identified and processed.

Data Acquisition

The DCE of brain tumor patients (n=10; 2 Meningioma, 7 high-grade and 1 low-grade glioma): T1-weighted 3D DCE data before and after the injection of contrast agent (0.1 mmol gadobutrol per kg body weight) was acquired on a 1.5 T (6 patients) and a 3 T MRI scanner (GE Healthcare, Milwaukee, USA). Acquisition parameters include: 0.94× 0.94×5 mm3 voxel size, 256×256×16-34 matrix, 13-25° flip angle, 1.21-1.35 ms TE, 4.37-5.82 ms TR, 6.2-10.2 s temporal resolution and 30-40 time points.

DCE of liver tumor patients (n=7, 1 metastasis, 1 hemangioma, 2 focal nodular hyperplasia, and 3 hepatocellular carcinoma). T1-weighted images using 3D stack of spiral sequence were acquired at 1.5 Tesla (GE Healthcare, Milwaukee, USA) before and after the injection of contrast agent (10 ml gadoxetate at 1 ml/s). Whole liver 4D images were reconstructed using sliding window. Imaging parameters included: scan time 54 s, frame rate 2.6 s, 15° flip angle, 1.76×1.76×5 mm3 voxel size, TR/TE 6/0.6 ms. Slices with the most prominent tumors were selected along aorta and portal vein ROIs as the inputs.

DCE of breast tumor patients (n=12, 6 benign tumors, and 6 malignant tumors). All patients underwent MRI examinations on a 3 T GE MRI system. Ultrafast DCE-MRI using Differential Subsampling with Cartesian Ordering (DISCO) was acquired continuously for 15 phases (16-channel breast coil) or 10 phases (8-channel breast coil) during the first 60 seconds, starting simultaneously with the start of contrast injection (0.1 mmol gadobutrol per kg body weight) at a rate of 2 ml/second. Additional acquisition parameters included TR/TE=3.8/1.7 msec, flip angle=10°, in-plane spatial resolution=1.6×1.6 mm, thickness=1.6 mm, temporal resolution=3.0-7.6 seconds, axial orientation.

Image Analysis

QTM processing by Eq.38, which was automated without any manual input, was performed uniformly on all data. The resulting real 4D image data $c^i(x, y, z)$, where x, y, z were discrete spatial indices and i=1, ..., $N_t$ temporal indices with $N_t$ the number of time frames, was taken to be the time-resolved DCE images of all tumor cases assuming linear relation between signal intensity change and contrast agent concentration. The system in Eq.38 was solved using the conjugate gradient algorithm with a relative tolerance of $10^{-3}$ and a maximum of 500 iterations. The regularization parameter $\lambda$ was chosen by performing an L-curve analysis.

Drift velocity amplitude of each voxel is calculated as follows:

$$|u(r)| = \sqrt{(u^x(r))^2 + (u^y(r))^2 + (u^z(r))^2} \quad [41]$$

Traditional Kety's method of regional blood flow ($f_{Kety}$) maps (ml/100 g/min) was also performed to obtain a comparison reference for the QTM drift velocity map $|u|$:

$$\partial_t c(r,t) = f_{Kety}(r)[c_A(t) - c(r,t)/v(r)], \quad [42]$$

where $c_A(t)$ is the global arterial input function (AIF) and v(r) the regional blood volume. For DCE data of the brain tumor, an AIF was selected in an enhancing artery close to the tumor volume. For DCE data of the liver, an AIF was selected as a combination of aorta and portal vein at the same axial slice of the tumor center. For DCE data of the breast, an AIF was selected at the ipsilateral internal mammary artery. The dependence of Kety's method on the AIF choice was assessed on brain tumor cases by comparing with another AIF at the internal carotid artery, and on liver tumor cases by selecting another AIF from an axial slice away from the tumor center.

Regions-of-interest (ROIs) were drawn inside the tumor volume and other tissue of interests for linear regression analysis between QTM and Kety's method among all subjects.

4.4. Results

Brain Tumors

Figure 21:
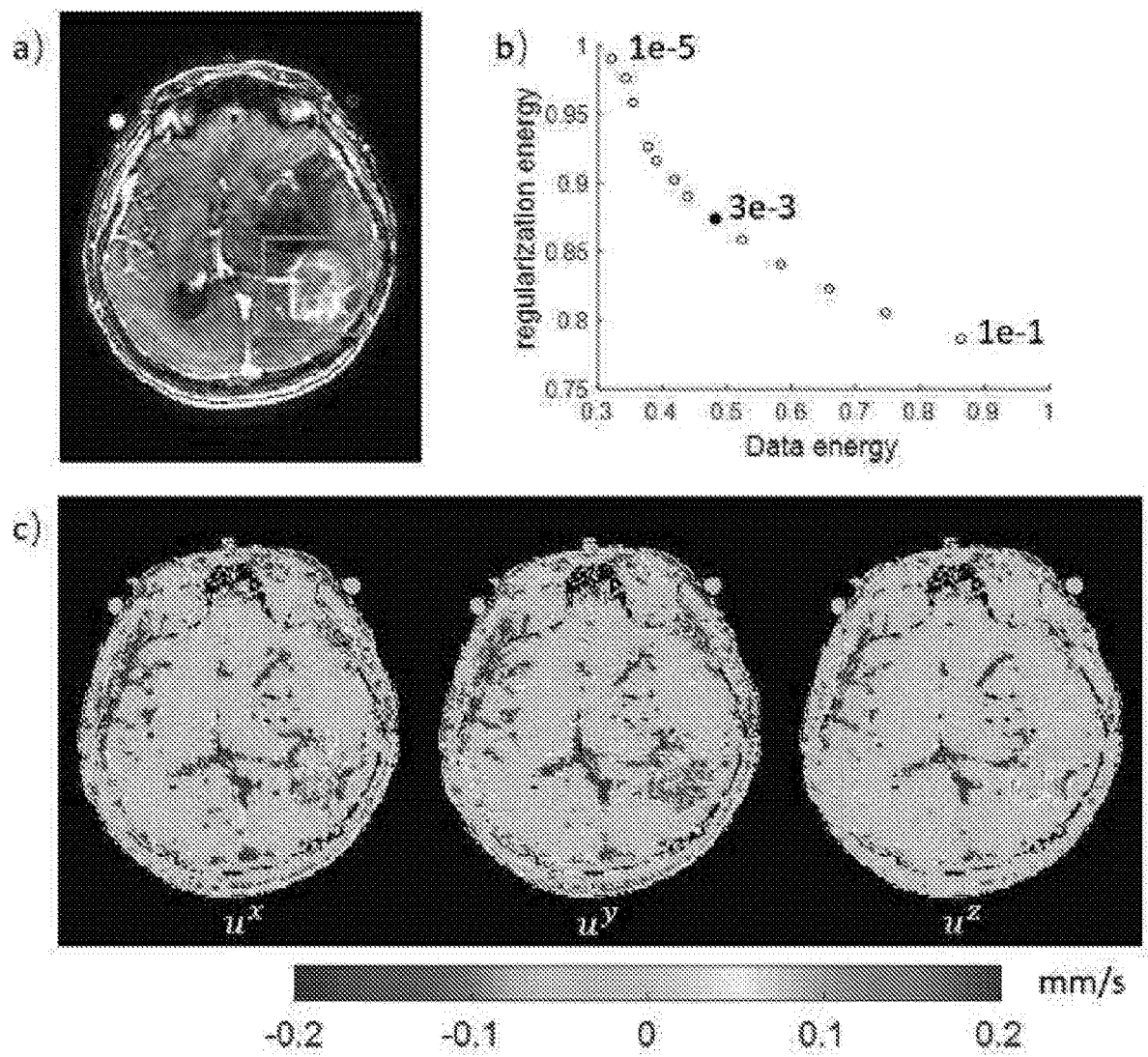
FIG. 21. a) post-Gd T1 weighted imaging showing a meningioma. Vector map of region in the red box is shown in FIG. 22. b) L-curve plot for Eq.37. The curve is annotated with the corresponding regularization parameter values. $\lambda=0.003$ was chosen for this and the remaining subjects. c) velocity map in three spatial directions x (anterior to posterior), y (right to left) and z (inferior to posterior)
Figure 22:
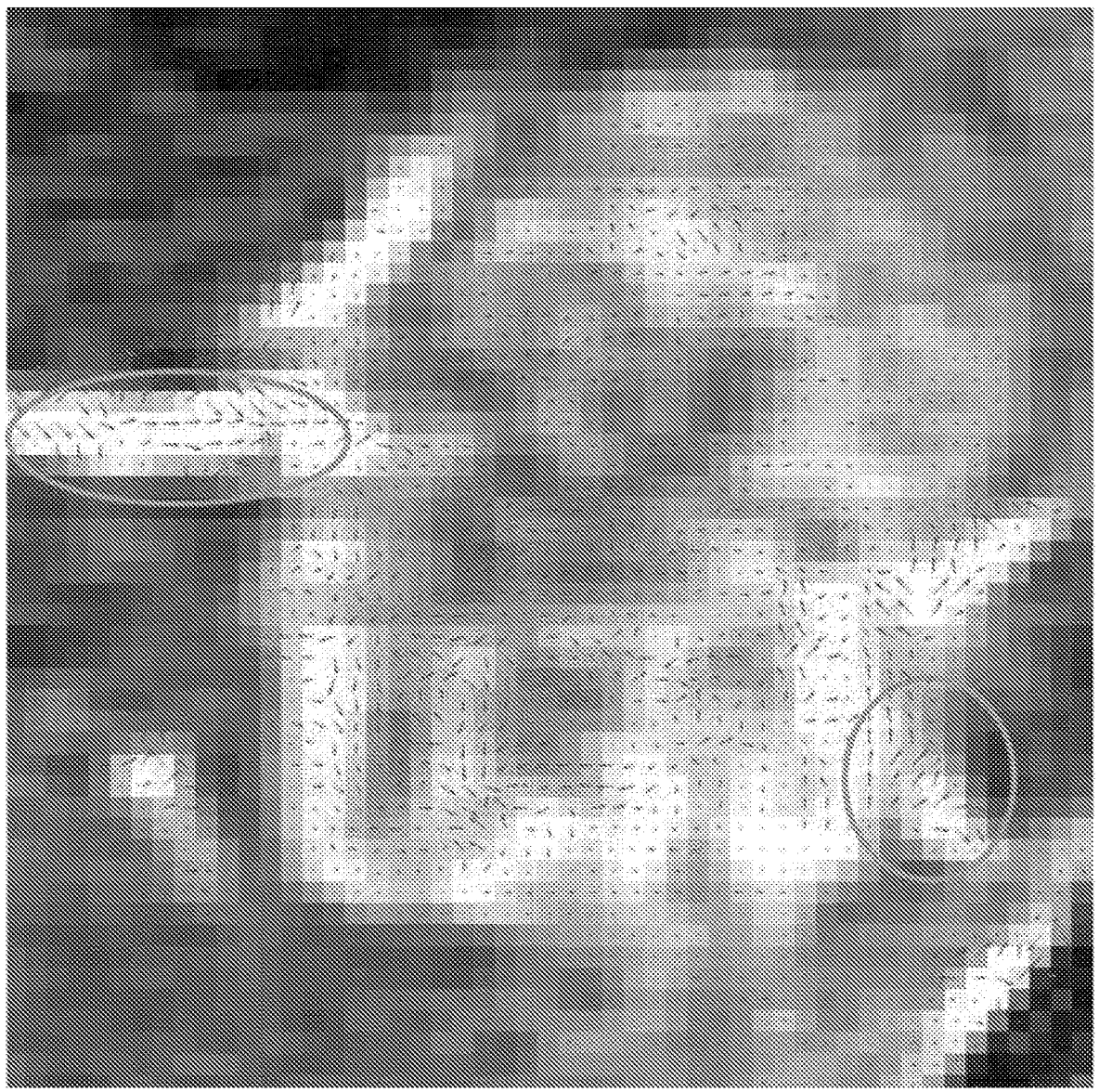
FIG. 22. Vector map of the x and y velocity components of the ROI in FIG. 21a. QTM method captured flow entering the tumor (circle on the left side of the image) and exiting the tumor (circle on the right of the image).

FIG. 21 illustrates a meningioma (WHO Grade II). The Gd-enhanced T1-weighted axial slice (FIG. 21a) depicts its anatomy. QTM velocity component map (FIG. 21c) and velocity vector u map (FIG. 22) depict flow in the vessel supporting tumor and flow inside tumor.

Figure 23:
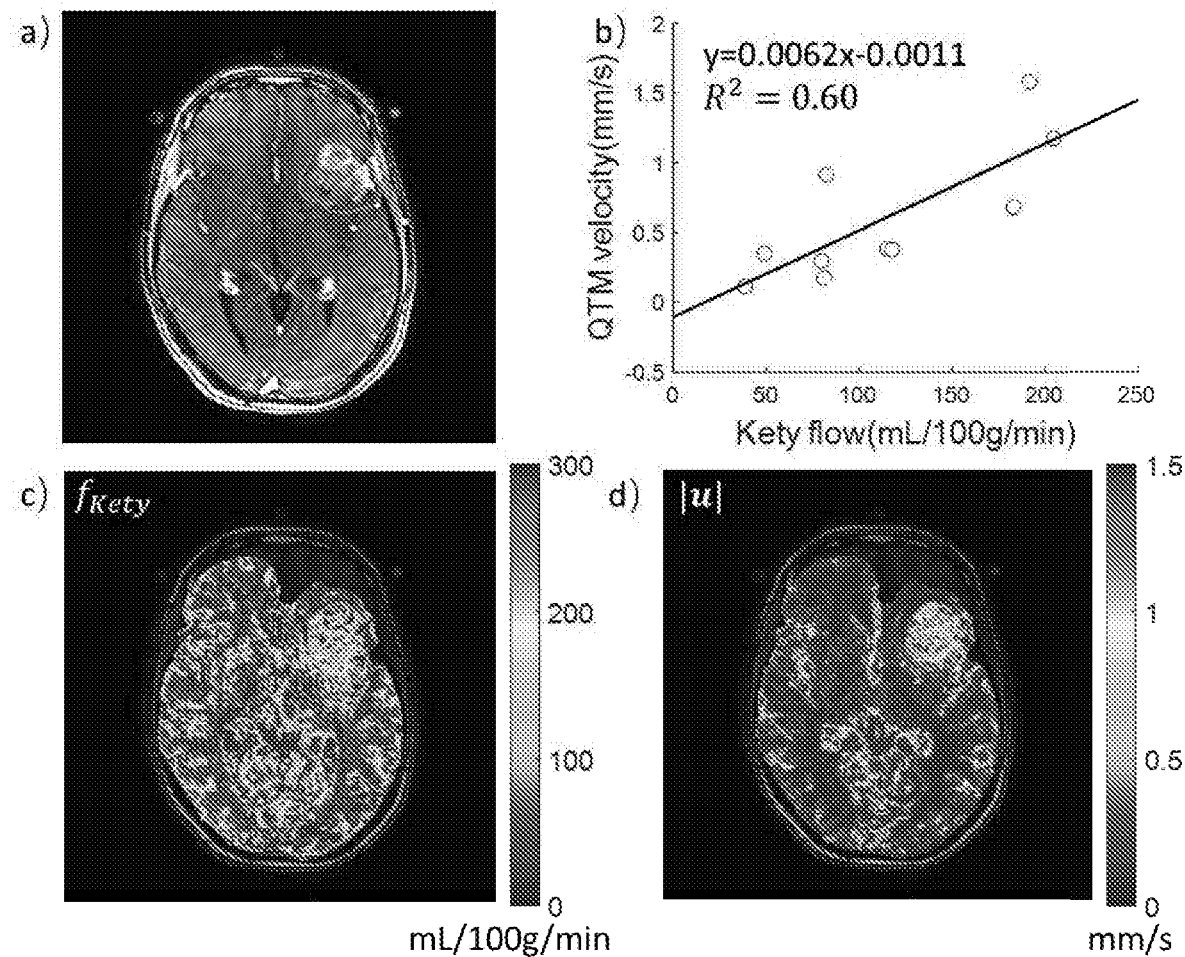
FIG. 23: Brain tumor with DCE imaging. Comparison between Kety's flow and QTM velocity |u| in an axial slice of a brain with high-grade glioma: a) post-Gd T1 weighted imaging showing tumor (red ROI), b) regression between $f_{Kety}$ and velocity |u| across tumors in all patients, c) Kety's blood flow $f_{Kety}$ with the AIF placed close to the tumor, and d) the QTM velocity |u|. Linear regression (b) showed good agreement with coefficient of determination 0.60.

FIG. 23 illustrates a glioblastoma (WHO Grade IV). The Gd-enhanced T1-weighted slice (FIG. 23a) depicts its anatomy with a tumor ROI indicated. Kety's flow $f_{Kety}$ (FIG. 23c) derived with the AIF placed close to the tumor and QTM velocity |u| (FIG. 23d) depict similar blood flow in the tumor, vessels and other tissue. FIG. 23b depicts the correlation between $f_{Kety}$ and |u| for all 10 brain tumor patients averaged within tumor ROIs, with linear regression showing good agreement with coefficient of determination 0.60.

The $f_{Kety}$ within a tumor ROI was higher on average when the AIF was placed close to the tumor compared to the internal carotid artery: Averaged over all patients, the relative difference was +16.0% within tumor ROIs.

Liver Tumors

Figure 24:
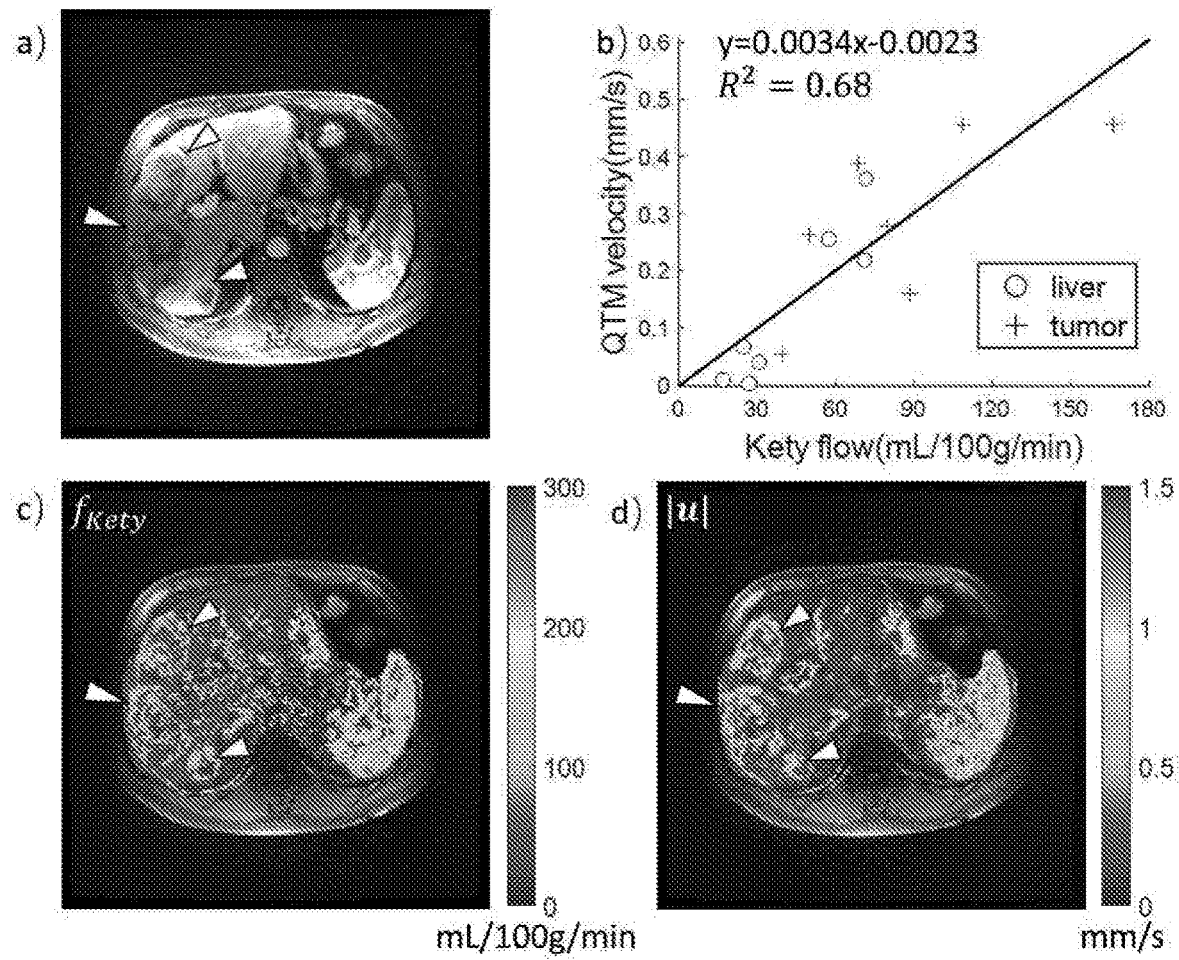
FIG. 24: Liver tumor (colon cancer metastasis) with DCE imaging. Comparison between Kety's flow and QTM velocity |u| in an axial slice of a liver with metastasis: a) post-Gd T1 weighted imaging showing tumor with enhanced rims (white arrow heads), b) regression between $f_{Kety}$ and velocity |u| across tumors in all patients, c) Kety's blood flow $f_{Kety}$ and d) the QTM velocity |u| corresponding to a). Linear regression (b) showed good agreement with coefficient of determination 0.68.

FIG. 24 illustrates a metastasis. Maps of Kety's flow $f_{Kety}$ (FIG. 24c) and QTM velocity |u| (FIG. 24d) show similar contrasts. Kety's flow $f_{Kety}$ and velocity |u| were higher (~4 times) in the tumor regions (white arrow heads) compared to normal-appearing liver, which corresponded to the tumor enhancement pattern on the post-Gd T1-weighted image (arrow heads in FIG. 24a). Linear regression analysis among all patients showed good agreement ($R^2$=0.68) between flow $f_{Kety}$ and velocity |u|.

Kety's method was sensitive to the AIF choice: among all cases an average relative difference of 11.9% in tumor $f_{Kety}$ and 6.6% in normal-appearing liver tissue $f_{Kety}$ was observed.

Breast Tumors

Figure 25:
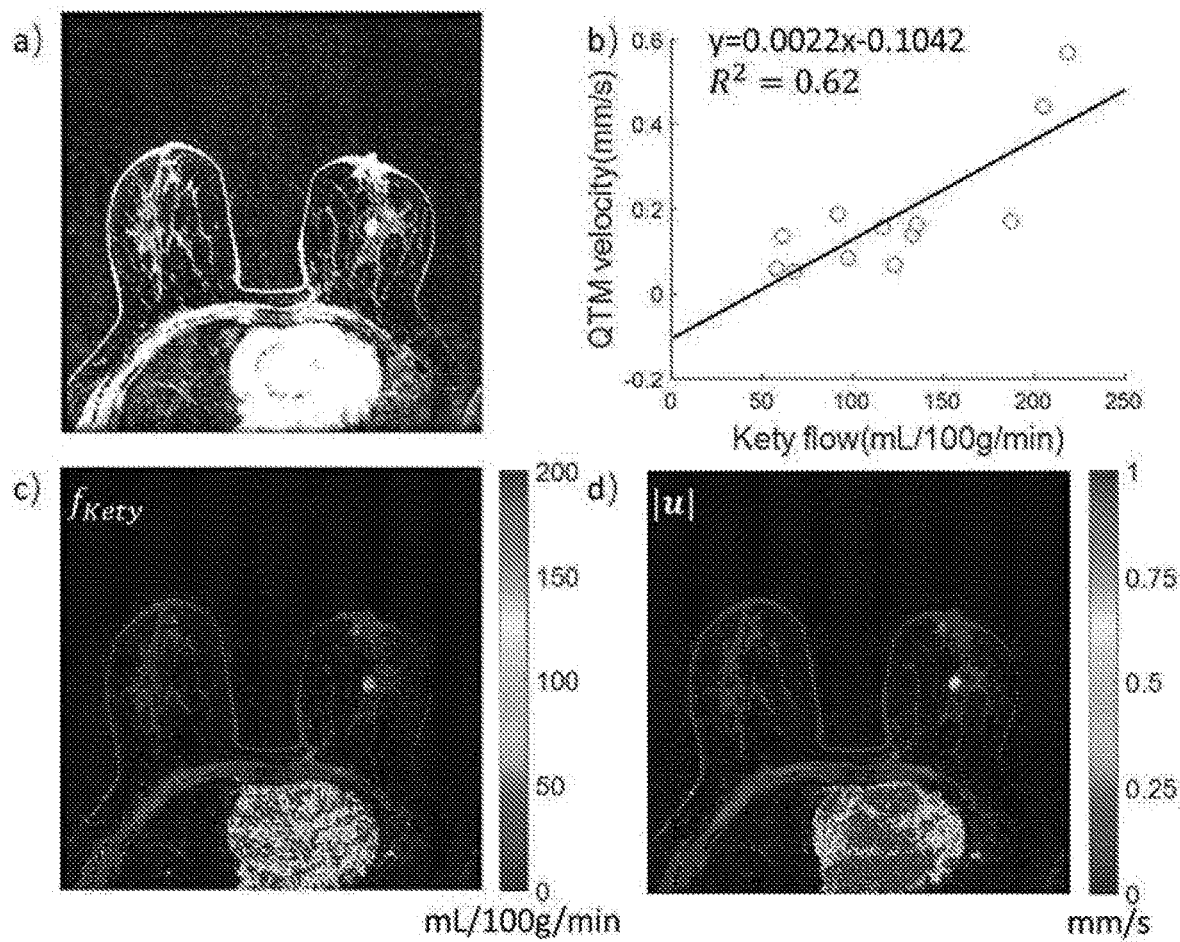
FIG. 25. Breast tumor with DCE imaging. Comparison between Kety's flow and QTM velocity |u| in a slice demonstrating breast carcinoma: a) post-Gd T1 weighted imaging showing tumor (red ROI), b) regression between $f_{Kety}$ and velocity |u| across tumors in all patients, c) Kety's blood flow $f_{Kety}$ and d) QTM velocity |u| corresponding to a). Linear regression (b) showed good agreement with coefficient of determination 0.62.

DISCO images, QTM velocity maps and $f_{Kety}$ maps for a malignant lesion are shown in FIG. 25. The lesion was well visualized on both QTM velocity map and $f_{Kety}$ map. Linear regression demonstrated a good correlation between QTM velocity and Kety's flow ($R^2$=0.62).

Figure 26:
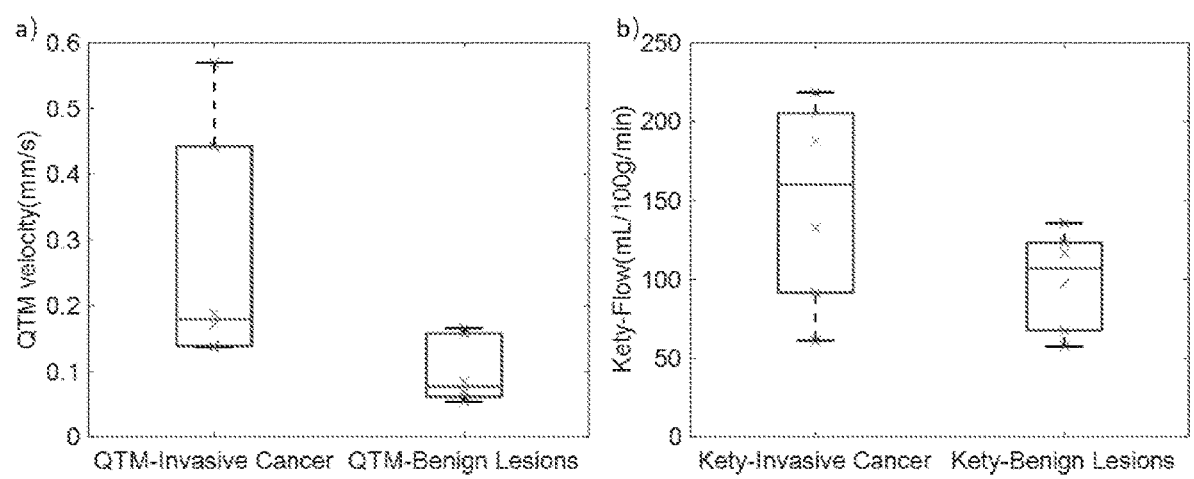
FIG. 26. Differentiating invasive breast cancer from benign breast lesions: a) QTM velocity demonstrated significance difference (p=0.04), but b) Kety's flow did not show significance difference (p=0.12).

In FIG. 26, a box plot shows the mean QTM velocity and Kety's flow for all lesions.

Paired t-tests demonstrated a statistically significant difference between malignant and benign lesions using QTM velocity (p=0.04), but no statistically significant difference using $f_{Kety}$ (p=0.12) (FIG. 26).

4.5. Conclusions

The preliminary data demonstrate the feasibility of computing drift velocity map from time-resolved image data of tracer concentration for a physics-based quantitative description of transport in tissue. This quantitative transport mapping (QTM) approach eliminates a major practical hurdle of selecting and a fundamental theoretical difficulty of using an arterial input function (AIF) in traditional Kety's method for quantitatively interpreting time-resolved imaging of tracer transport. For use in routine clinical practice, the elimination of AIF makes QTM fully-automated and user-friendly, more robust than Kety's method. Preliminary data suggests that the drift velocity map from QTM is promising for characterizing tumor blood flow.

The transport partial differential equations (Eqs.31-35) reflect the physics law of mass conservation and dynamic changes at a location: temporal change in a local quantity is only related to relevant local quantities. The voxelization by integrating the solution to the transport equations over the intravoxel tissue microstructure provides a systematic way to build tissue compartments based on fundamental tissue properties, which may be a desirable alternative to traditional phenomenological compartments. Fitting time-resolved tracer image data to the mass conservation equation has been used to quantify blood flow of an artery in high resolution x-ray projection angiography without concern of voxelization. Voxelization of the transport equations using microstructure is required to understand tissue transport, including regional blood flow, transport pressure, vessel wall permeability and diffusion in tissue. In this first report of QTM, an approximation for a porous medium with large flow is presented as the physical mass conservation law, which eliminates the fundamental AIF required in Kety's method used in all current perfusion quantification techniques in medical imaging.

Historically, Kety's equation is an extension of the Fick principle of mass conservation between blood input and output to an organ by accounting for exchange of diffusible tracers in tissue as described by the blood partition coefficient or regional blood volume. The fundamental flaw in the current perfusion quantification methods is to extend Kety's equation of global quantities for characterizing the whole organ to voxel perfusion that must be based on local quantities or fields. Kety's equation treats a whole organ as a lumped element in a manner similar to that Ohm's law treats a conductor as a lumped element without considering the field distribution within the conductor. As in electrodynamics, local tissue perfusion requires considering distributional physical quantities that are characterized by the vector and tensor fields and their corresponding partial differential equation (PDE) governing local variations.

The preliminary QTM data of drift velocity reported here characterize various tumors where flow is large and vessel wall is porous. While a coarse correlation among Kety's flow and QSM velocity is observed, QTM is substantially different from Kety's method. The first difference is the use of manual ROI for defining AIF in Kety's method, while QTM is fully automated with elimination of AIF. It is well known that directly or indirectly estimated AIF causes the poor reproducibility for perfusion imaging, as observed here in tumor data of the brain and liver. Attempts to estimate local AIFs or to include a delay as an unknown variable cannot determine the important local dispersion of AIF. Perhaps more importantly, it is often difficult to perform manual drawing of arterial ROI, making Kety's method difficult to use and reproduce in practice.

The second difference is indicated in that quantitative correlation of QTM velocity and Kety's flow is variable from tumor to tumor. Particularly, QTM velocity demonstrated a statistically significant difference between malignant and benign lesions in the breast, while Kety's flow failed to do so. The better sensitivity of QTM over Kety's method may be due to 1) proper biophysics modeling of contrast agent transport in tumor and 2) elimination variance typically associated with manual input in data processing. This very encouraging preliminary finding warrants further investigation over a large cohort of patients to establish the relationship between flow velocity and tumor malignancy.

The third difference is that the drift velocity map from QTM is directional, while the flow map from Kety's method is a scalar. Tissue perfusion as a transport process is directional and should be treated as directional in interpreting data. This QTM work brings physics principles of transport equations into previous attempts in introducing direction to perfusion interpretation. The directional information from QTM may be very useful in guiding lesion intervention. For example, in interventional delivery of therapy via endovascular catheters or intratissue injection, it is important to know transport direction for upstream injection.

The mean velocity magnitude in tumor ROIs observed here are in range from 0.1 mm/s to 1 mm/s. This velocity magnitude is a volume average of tracer drift velocity inside voxel. Although tumor blood flow has been measured and discussed in many studies, tumor blood velocity has not been well explored quantitatively. Recent studies on tumor blood velocity measurement using convectional MRI, capillaroscopy and finite element method simulation reported similar velocity range in tumor tissue (from 0.1 mm/s to 0.8 mm/s in rodent tumor vessels with diameter ranging from 20 μm to 70 μm, and 0.2 mm/s in porous liver tumor tissue). This indicates that QTM method provides a reasonable estimation of blood velocity in tumor. The inventors have thus validated that QTM provides an accurate estimate of flow velocity in a tube, consistent with x-ray angiography results and suggest the merit of validation the accuracy of QTM velocity in, and application to, various imaging situations.

This first attempt to solve QTM is limited to modeling tissue as a uniform porous media with weak microstructure for a simple formulation of the forward problem. Important future work to further develop QTM includes adding vascular microstructure information in voxelizing the transport equations, which would allow voxel-specific averaging of the drift velocity, tissue diffusion and vessel permeability, as well as calculation of flow into/out of the voxel. Vessel wall permeability deserves particular considerations because of its clinical importance in distinguishing pathological tissue from normal. Vascular permeability has been defined as the flux through a wall over the concentration gradient, particularly in MRI literature, or as the flux through a wall over the pressure gradient as in Starling's equation; both definitions are equivalent, because chemical osmotic pressure likely dominates the pressure gradient and can be approximated by the van't Hoff equation. A radial velocity in vessels can be used to account for tracer leaking from the vascular compartment, but this radial velocity may be small in many applications.

The determination of transport parameters p, D, ψ from time resolved image data and the inverse problem of Eqs. 31-35 can be solved using deep learning. An artificial neural network (ANN) such as the U-Net described above can be trained by simulated data over a range of p, D, ψ values covering all possible pathophysiological values for these parameters. The simulation can be performed according to Eqs.31-35, tissue information including vasculature details, and other relevant imaging signal equations with addition of appropriate noise added to simulated image signal. This simulation approach applies to MRI, CT, PET and other imaging modalities. The simulated image data approximating data obtained from patients is input for ANN, and p, D, ψ as "label" of imaging data are output for ANN. Then the trained ANN can be used on in vivo imaging data acquired from subjects to generate maps of transport parameters.

Other important future work includes extending the physics based QTM for perfusion quantification to other imaging modalities and validating QTM against a reference standard. QTM, applied here to DCE MRI data, can be extended to other imaging modalities including CT, PET and single-photon emission computed tomography (SPECT), as well as to arterial spin labeling data in MRI. A major issue in quantitative perfusion imaging is the lack of validation against the truth, and Kety's method seems yet to be validated experimentally with respect to a true flow map that is determined by a method independent of Kety's method. This critical validation of perfusion quantification of any methods, including both Kety's method and QTM, must be performed in the future using an experimental setup where perfusion is known.

In summary, quantitative transport mapping (QTM) by fitting the local transport equations to time-resolved imaging (4D image data) of tracer transport in tissue overcomes the fundamental AIF limit in Kety's method. QTM under the weak microstructure approximation can process time-resolved imaging data to automatically generate a drift velocity map that is promising for characterizing blood flow in brain, breast and liver tumors.

5. Cerebral Metabolic Oxygen Extraction Fraction (OEF) Mapping

Implementations of the abovementioned techniques can be used in a variety of applications. As examples, the following section describes the application of one or more of these techniques to numerical simulation, phantom experiments, and human brain imaging, particularly for determining deoxyheme iron concentration and tissue oxygen extraction fraction using a cluster analysis of time evolution method that significantly improves SNR and robustness of OEF mapping.

5.1. Introduction

The cerebral metabolic rate of oxygen (CMRO2) and oxygen extraction fraction (OEF) are important markers of brain tissue viability and function, such as in stroke, and their mapping using MRI has received great interest. Quantitative models have been proposed to investigate the effect of deoxyhemoglobin in blood, a strong paramagnetic source, on the MRI signal: 1) magnitude signal modeling methods such as quantitative imaging of extraction of oxygen and tissue consumption (QUIXOTIC), calibrated fMRI, and quantitative blood oxygen level dependent (BOLD) contrast (qBOLD), and 2) phase signal modeling methods for whole brain CMRO2 and a voxel-wise quantitative susceptibility mapping (QSM)-based CMRO2 method.

Recently, a combined model of the QSM-based method and qBOLD (QSM+qBOLD) was introduced to remove assumptions in individual models and to consider the effect of OEF on both magnitude and phase signal from the same underlying gradient echo (GRE) data. While it addressed issues in the separate QSM and qBOLD based methods, shortcomings remained. For instance, the qBOLD model is nonlinear with strong coupling between venous oxygenation (Y) and venous blood volume (v), such that its inversion is a difficult non-convex optimization that is highly sensitive to data acquisition noise. This can lead to substantial errors in the estimated parameters for typical SNR levels. Since the QSM+qBOLD model relies partly on the qBOLD model, it suffers from sensitivity to noise as well.

In this study is introduced a cluster analysis of time evolution (CAT) method to overcome the noise sensitivity of QSM+qBOLD to obtain more accurate model parameters, such as OEF, by improving the effective SNR. Voxels with similar GRE signal evolution should have similar parameter values. Using machine learning methods, the whole brain can be divided into a number of clusters much smaller than the number of voxels based on similarity in the GRE signal evolution. For each cluster, a single set of model parameters is assumed, therefore effectively increasing the SNR by an average over each cluster. This improvement in SNR is expected to lead to more accurate OEF values. The results from the CAT method are then used as the initial guesses for voxel-wise optimization. In both healthy subjects and ischemic stroke patients, the proposed CAT QSM+qBOLD method is compared with the prior QSM+qBOLD method (20) that used an OEF with a constant initial guess for the whole brain.

5.2. Theory

CMRO$_2$ (mol/100 g/min) and OEF (%) can be expressed as $$CMRO_2 = CBF \cdot OEF \cdot [H]_a, \quad OEF = 1 - \frac{Y}{Y_a},$$

where CBF is the cerebral blood flow (ml/100 g/min), $[H]_a$ is the oxygenated heme molar concentration in the arteriole (7.377 μmol/ml) based on a hematocrit of Hct=0.357, Y the venous oxygenation (dimensionless), and $Y_a$ the arterial oxygenation (set to 0.98). Assuming that deoxyheme irons are distributed in the draining venules and veins of cylindric geometry in random orientations while other susceptibility sources including nonheme irons are diffusely distributed in tissue, the qBOLD method models the gradient echo magnitude signal of a voxel as follows:

$$S_{qBOLD}(t) = S_0 \cdot e^{-R_2 \cdot t} \cdot F_{BOLD}(Y, v, \chi_{nb}, t) \cdot G(t) \quad [43]$$

where G(t) is the macroscopic field inhomogeneity contribution in GRE at time t, $F_{BOLD}$ is the GRE signal decay due to the presence of deoxygenated blood within a vessel network inside the voxel: $F_{BOLD}(Y, v, \chi_{nb}, t) = \exp[-v \cdot f_s(\delta\omega \cdot t)]$, where $f_s$ is the signal decay by the blood vessel network, and δω is the characteristic frequency due to the susceptibility difference between deoxygenated blood and the surrounding tissue:

$$\delta\omega(Y, \chi_{nb}) = \frac{1}{3} \cdot \gamma \cdot B_0 \cdot [Hct \cdot \Delta\chi_0 \cdot (1-Y) + \chi_{ba} - \chi_{nb}] \quad [44]$$

with γ the gyromagnetic ratio (267.513 MHz/T), $B_0$ the main magnetic field (3 T in the study), Hct hematocrit (0.357), $\Delta\chi_0$ the susceptibility difference between fully oxygenated and fully deoxygenated red blood cell (4π×0.27 ppm), and $\chi_{ba}$ the susceptibility of fully oxygenated blood, −108.3 ppb estimated using Hct 0.357.

Figure 27:
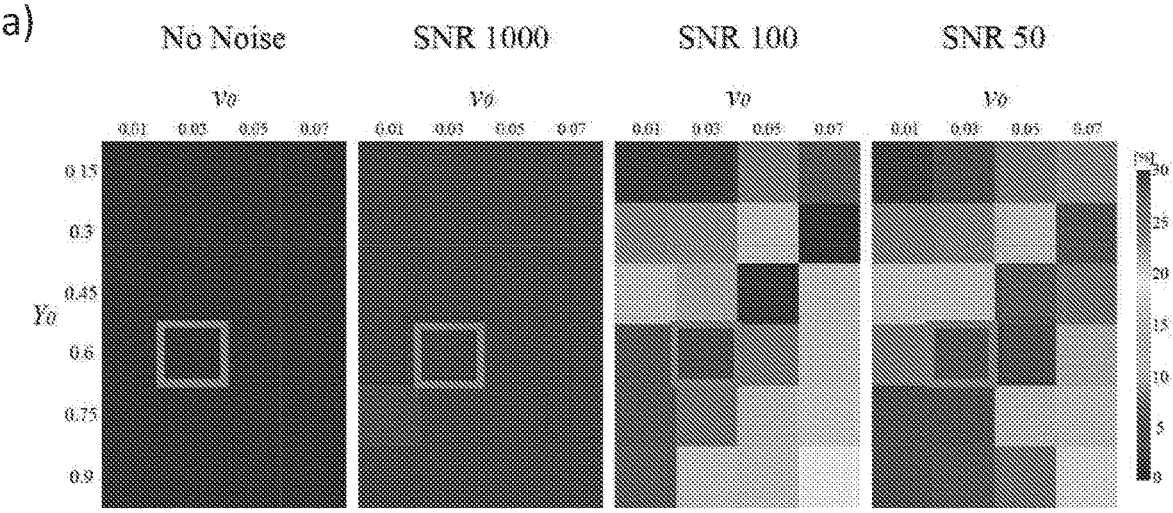
FIG. 27. a) Influence of SNR on the sensitivity of the estimated Y on the initial guess. Shown is the relative error between the estimated Y and the ground truth. $Y_0$ and $v_0$ are the initial guesses of Y and v, respectively. As SNR decreases, Y becomes increasingly more sensitive to the initial guess, resulting in larger errors when the initial guess is away from the ground truth value. The gray box indicates the ground truth values. b) Comparison between the OEF obtained using the prior QSM+qBOLD and CAT QSM+qBOLD at different SNRs in simulation. At all SNRs, CAT QSM+qBOLD captures low OEF values, whereas the prior QSM+qBOLD is not sensitive to low OEF values at low SNRs. The numbers in white indicate the OEF average and standard deviation in the whole brain, and black represents the root-mean-square error (RMSE)
Figure 27:
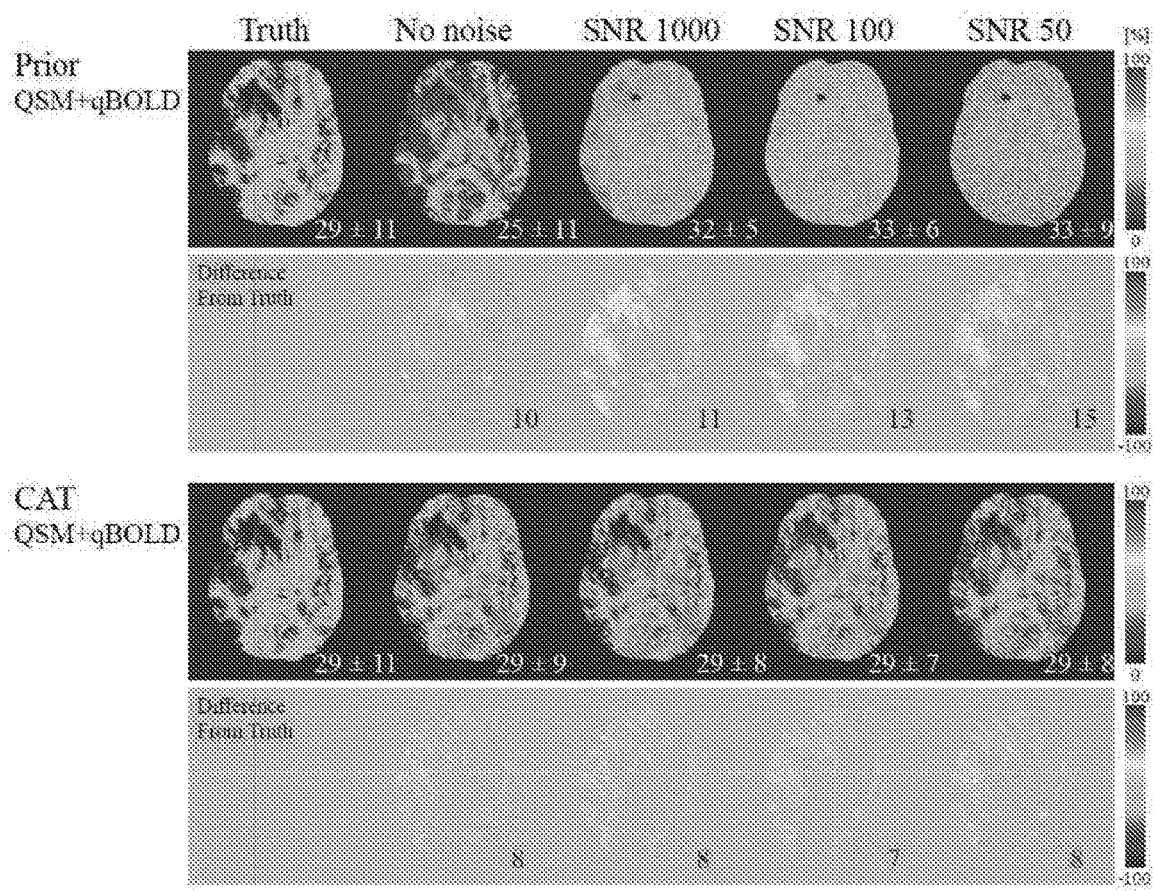

The optimization problem of fitting data to Eq.43 is non-convex, and $F_{BOLD}$ shows high coupling between v, Y, and $\chi_{nb}$. The accuracy of estimating v, Y, and $\chi_{nb}$ depends on initialization and is highly sensitive to SNR. The qBOLD sensitivity to noise propagates into the combined QSM+qBOLD model (FIG. 27a). Hence, high SNR is needed to obtain accurate OEF.

To increase the effective SNR before fitting, a novel Cluster Analysis of Time evolution method for QSM+qBOLD ("CAT QSM+qBOLD" hereafter) is presently proposed. Voxels with similar magnitude signal time-course $S_{qBOLD}(t)/G(t)$ have similar tissue parameters (Y, v, $R_2$) and form a cluster. A cluster is assumed to contain a substantial number of voxels, and clusters form a sparse representation of all voxel signal time-courses, which can be used as a powerful constraint to make QSM+qBOLD robust against noise. K-means clustering can be used to identify all clusters. The QSM+qBOLD problem is first solved with a cluster-wise optimization by assuming parameters Y, v, and $R_2$ to be constant within each cluster while $S_0$ and $\chi_{nb}$ vary from voxel to voxel, taking advantage of magnitude and phase signals dominantly depending on $S_0$ and $\chi_{nb}$. Then, a voxel-wise optimization is performed by using the solution from the cluster-wise optimization as the initial guess.

The joint QSM+qBOLD optimization is formulated as:

$$Y^*, v^*, R_2^*, S_0^*, \chi_{nb}^* = \underset{Y,v,R_2,S_0,\chi_{nb}}{\arg\min} \quad [45]$$

$$\left\{ w\|F_{QSM}(Y, v, \chi_{nb}) - \chi\|_2^2 + \|S(t) - S_{qBOLD}(S_0, Y, v, R_2, \chi_{nb}, t)\|_2^2 + \lambda(\overline{OEF(Y)} - OEF_{wb})^2 \right\}$$

where w is the weighting on the first QSM term which has $$F_{QSM}(Y, v, \chi_{nb}) = \quad [46]$$

$$\left[ \frac{\chi_{ba}}{\alpha} + \psi_{Hb} \cdot \Delta\chi_{Hb} \cdot \left( -Y + \frac{1-(1-\alpha) \cdot Y_a}{\alpha} \right) \right] \cdot v + \left(1 - \frac{v}{\alpha}\right) \cdot \chi_{nb}$$

with χ the measured susceptibility from QSM, $\chi_{ba}=\psi_{Hb} \cdot \chi_{oHb}+(1-\psi_{Hb}) \cdot \chi_p$ the susceptibility of fully oxygenated blood, α the ratio between the venous and total blood volume v/CBV (assumed to be constant 0.77), $\psi_{Hb}$ the hemoglobin volume fraction (set to 0.0909 for Hct=0.357), $\chi_p$ the blood plasma susceptibility (set to −37.7 ppb), $\Delta\chi_{Hb}$ the susceptibility difference between deoxy- and oxy-hemoglobin (12522 ppb), and $$Y_a = \frac{[H] - [dH]_a}{[H]}$$

the arterial oxygenation. The third term is the physiological regularization on Y such that the OEF averaged over the whole brain, $\overline{OEF(Y)}$, should be similar to $OEF_{wb}$, the whole brain OEF value estimated from the main draining vein, the straight sinus (SS): $OEF_{wb}=Hct_{vt} \cdot OEF_{ss}$ where $Hct_{vt}$ is the hematocrit ratio (0.759) between large vessels and brain tissue, and $OEF_{ss}=1-Y_{ss}/Y_a$ with $Y_{ss}$ estimated from the susceptibility in the SS with $\psi_{Hb}=0.1197$, v=1 and $\chi_{nb}=0$ in Eq.46. In Eq.45, S(t) is the measured GRE data. w and λ are the regularization strength determined by the L-curve method.

5.3. Methods and Materials

Simulations.

A simulation was performed to investigate the relationship between SNR and the dependency of OEF on the initial guess. The GRE signals and the QSM values were simulated using Eq.43 and Eq.46, respectively. The following input parameters were used: Y=60%, v=3%, $\chi_{nb}$=−0.1 ppm, $S_0$=1000 au, and $R_2$=20 Hz. The same 7 TEs acquired in healthy subjects (see below) were used: $TE_1/\Delta TE/TE_7$=2.3/3.9/25.8 ms. Then, Gaussian noise was added to the simulated GRE signals and the QSM values resulting in data sets with SNR: ∞ (no noise), 1000, 100, and 50. The Y and v were subsequently estimated as described below. To examine the dependency on the initial guess, the optimization was performed with different initial guesses for Y(0.15, 0.3, 0.45, 0.6, 0.75, 0.9) and v (0.01, 0.03, 0.05, 0.07) and using the ground truth as the initial values for $S_0$, $\chi_{nb}$ and $R_2$. This was repeated for 500 instantiations of the simulation noise. w/λ=5×10$^{-3}$/0. The relative error was computed as $$\frac{|Y_{result} - Y_{true}|}{|Y_{true}|}.$$

To compare the accuracies of the proposed CAT QSM+qBOLD to the prior QSM+qBOLD, a simulation was performed. First, the GRE signals and the QSM values for each brain voxel were simulated using Eq.43 and Eq.46, respectively. The input was the CAT QSM+qBOLD result from one stroke patient, who was imaged 6 days post onset. The same 8 TEs that were acquired in stroke patients (see below) were used: $TE_1/\Delta TE/TE_8$=4.5/5/39.3 ms. Gaussian noise was added to the simulated GRE signals and the QSM values, leading to data sets with SNR: ∞ (no noise), 1000, 100, and 50. The simulated data was processed into two ways: 1) prior QSM+qBOLD with a constant OEF initial guess for the whole brain and 2) CAT QSM+qBOLD. The same optimization setting was used in the healthy subjects and stroke patients. $OEF_{wb}$ was set to the average ground truth OEF across the brain (29%). For the CAT QSM+qBOLD, $w/\lambda=5\times10^{-3}/10^3$ (from L-curve analysis on 2 healthy subjects and 2 stroke patients). Root-mean-square error (RMSE) was calculated to measure the difference from the truth.

In Vivo Imaging Acquisition

Healthy subjects: This study was approved by the local Institutional Review Board. Healthy volunteers were recruited (n=11; 10 males, 1 female, mean age 34±12 years) for brain MRI on a 3 T scanner (HDxt, GE Healthcare) using an 8-channel brain receiver coil. After obtaining consent, all subjects were instructed to avoid caffeine or alcohol intake 24 hours prior to the MRI. MRI was performed in the resting state using a 3D fast spin echo (FSE) arterial spin labeling (ASL) sequence, a 3D multi-echo spoiled gradient echo (GRE) sequence, and an inversion prepared T1w SPGR sequence (BRAVO). The 3D FSE ASL sequence parameters were: 20 cm FOV, 1.56 mm in-plane resolution, 3.5 mm slice thickness, 1500 ms labeling period, 1525 ms post-label delay, 976.6 Hz/pixel bandwidth, spiral sampling of 8 interleaves with 512 readout points per leaf, 35 axial slices, 10.1 ms TE, 4533 ms TR, and 3 signal averages. The 3D GRE sequence parameters were: 0.78 mm in-plane resolution, 1.2 mm slice thickness, volume coverage identical to the 3D FSE ASL sequence, 7 equally spaced echoes, 2.3 ms for the first TE, 3.9 ms echo spacing, 30.5 ms TR, 488.3 Hz/pixel band width, and 15° flip angle. The pulse sequence was flow-compensated in all three directions. The inversion prepared T1w SPGR sequence parameters were: 0.78 mm in-plane resolution, 1.2 mm slice thickness, volume coverage identical to the 3D FSE ASL sequence, 2.92 ms TE, 7.69 ms TR, 450 ms prep time, 195.2 Hz/pixel bandwidth, and 15° flip angle.

QSM reconstruction was performed as follows: first, an adaptive quadratic-fit of the GRE phase was used to estimate the total field. Second, the Projection onto dipole fields (PDF) method was used to obtain the local field. Finally, the Morphology Enabled Dipole Inversion with automatic uniform cerebrospinal fluid zero reference (MEDI+0) algorithm was used to compute susceptibility. CBF maps (ml/100 g/min) were generated from the ASL data using the Func-Tool software package (GE Healthcare, Waukesha, WI, USA). All images were co-registered and interpolated to the resolution of the QSM maps using the FSL FLIRT algorithm.

Stroke patients: 5 patients with ischemic stroke underwent 3D ASL, 3D GRE, and DWI on a clinical 3 T scanner (GE MR Discovery 750) using a 32-channel brain receiver coil. The time interval between stroke onset and MRI examination ranged between 6 hours and 12 days. All lesions were located in unilateral cerebral artery territory. The 3D FSE ASL sequence parameters were: 24 cm FOV, 1.9 mm in-plane resolution, 2.0 mm slice thickness, 1500 ms labeling period, 1525 ms post-label delay, 976.6 Hz/pixel bandwidth, 68 axial slices, 14.6 ms TE, 4787 ms TR, and 3 signal averages. The 3D GRE sequence parameters were: 0.47 mm in-plane resolution, 2 mm slice thickness, volume coverage identical to the 3D FSE ASL sequence, 8 equally spaced echoes, 4.5 ms for the first TE, 4.9 ms echo spacing, 42.8 ms TR, 244.1 Hz/pixel band width, and 20° flip angle. DWI sequence parameters were: 24 cm FOV, 0.94 mm in-plane resolution, 3.2 mm slice thickness, 1953.1 Hz/pixel bandwidth, 0, 1000 s/mm² b-values, 71 ms TE, 3000 ms TR, and 4 signal averages.

QSM and CBF processing was the same as in the healthy subjects, except a linear-fit of the GRE phase was used to estimate the total field as 3D flow-compensation was not available on the scanner used in the patient studies.

Clustering

The magnitude of the acquired GRE signal S(t) was used for clustering after the macroscopic field inhomogeneity contribution, G was removed. The GRE signal for each voxel was normalized by the average signal across echoes. The k-means clustering algorithm was then applied to the normalized magnitude signal. Each voxel can be considered as a point in the vector space where the dimension is the number of echoes. The points which are close to each other (the voxels with similar signal evolution) fall into the same cluster. The cluster centroid indicates a representative signal evolution. The squared Euclidean distance was used to measure how close the points are in the vector space (how much similar signal evolution the voxels have). The proper number of clusters was automatically determined by the x-means method, a modified, fast k-means method. First, it performs a conventional k-means with a given initial number of clusters. Second, each centroid is replaced by two child centroids, and a local k-means (k=2) is performed within each cluster using the child centroids as initial guesses. This is done for each cluster obtained in the first step. Third, the decision of whether each cluster should be replaced by its two child clusters is made based on the Bayesian Information Criterion (BIC), which is the sum of the clustering log-likelihood and the penalty on the number of clusters. If, for instance, the BIC value is larger for the two children compared to that of the parent, then the child clusters should replace the parent cluster. As the number of clusters increases, so will the goodness of fitting (log-likelihood), but this can lead to overfitting to the noise. The penalty term on the number of clusters in BIC is addressed to reduce this possibility. The x-means algorithm stops when no more clusters can be split up or when the number of clusters reaches an a priori set maximum. Conventional k-means is then repeated one last time, setting the number of clusters to the value obtained with the x-means method. In this study, x-means used 1 for the initial number of clusters and 50 for the maximum number of clusters.

For speed, the x-means algorithm to obtain the number of clusters K was carried out on 10% of the total voxels, randomly selected. This process was repeated 10 times and the K with the largest BIC value among the 10 trials was selected. The corresponding centroids were then used as the initial centroids for the final k-means on all voxels.

Optimization

The QSM+qBOLD optimization (Eq.45) was solved by separating it into the following optimization problems: updating $S_0$ based on qBOLD (Eq.47); then $\chi_{nb}$ based on QSM+qBOLD optimization (Eq.48) and the computed susceptibility map $\chi$; and updating the Y, v, $R_2$ values based on the QSM+qBOLD optimization (Eq.49). Using k to denote iteration number, these steps are:

$$S_0^{k+1} = \arg\min_{S_0} \|S(t) - S_{qBOLD}(S_0, Y^k, v^k, R_2^k, \chi_{nb}^k)\|_2^2 \quad [47]$$

$$\chi_{nb}^{k+1} = \arg\min_{\chi_{nb}} \left\{ \begin{array}{l} w\|F_{QSM}(Y^k, v^k, \chi_{nb}) - \chi\|_2^2 \\ +\|S(t) - S_{qBOLD}(S_0^{k+1}, Y^k, v^k, R_2^k, \chi_{nb}^k)\|_2^2 \end{array} \right\} \quad [48]$$

$$Y^{k+1}, v^{k+1}, R_2^{k+1} = \arg\min_{Y, v, R_2} \quad [49]$$

$$\left\{ \begin{array}{l} w\|F_{QSM}(Y, v, \chi_{nb}^{k+1}) - \chi\|_2^2 + \\ \|S(t) - S_{qBOLD}(S_0^{k+1}, Y, v, R_2, \chi_{nb}^{k+1})\|_2^2 + \lambda(\overline{OEF(Y)} - OEF_{wb})^2 \end{array} \right\}$$

Eq.47 was solved using closed form expressions. Then, Eq.48 and Eq.49 was solved iteratively (see below).

First, rough initial guesses for Y, v, $R_2$ were obtained as follows: $Y_0$ was estimated from $OEF_{wb}$ in Eq.45. The SS mask was obtained automatically using global and regional thresholding on QSM combined with positional (inferior, posterior brain) and geometrical (straight) constraints. For initial guesses for v ($v_0$), the whole brain was roughly segmented into three parts, gray matter (GM), white matter (WM), and cerebral spinal fluid (CSF) with either T1w (11 healthy subjects and 4 stroke patients) or T2-FLAIR image (1 stroke patient without T1w image) via FSL FAST. $v_0$ was set to 3/1.5/1% for GM/WM/CSF, respectively based on literature. $\chi_{nb,0}$ was set to satisfy Eq.46 with $Y_0$ and $v_0$. The initial guess $S_{0,0}$ and $R_{2,0}$ were obtained by solving Eq.43, and fixing Y, v and $\chi_{nb}$ to these rough initial guesses. The resulting mono-exponential fit was performed using ARLO. Before fitting, 3D Gaussian smoothing was performed on S and G to improve SNR (kernel with standard deviation of 0.5 of the diagonal length of the voxel). Voxels with $R_2>100$ Hz or $R_2<2.5$ Hz were considered as outliers from all subsequent processing.

Second, a cluster-based optimization was performed, in which the unknowns Y, v, $R_2$ were assumed to be constant within each cluster. The average of the voxel-wise initial guess values for Y, v, $R_2$ was used as the initial value for the cluster-wise optimization. To improve convergence behavior during non-linear fitting, the unknowns Y, v, $\chi_{nb}$, $R_2$ were scaled to have roughly the same order of magnitude:

$$x \mapsto \frac{x}{c},$$

where x is the unknown in the original scale, c is the scaling factor: 0.5, 0.05, $|\chi_{nb,0}|$, avg($R_{2,0}$)+4·SD ($R_{2,0}$) for Y, V, $X_{nb}$, $R_2$, respectively. avg($R_{2,0}$) and SD($R_{2,0}$) denote the average and standard deviation of $R_{2,0}$ in the cluster, respectively. Lower and upper bounds were set to 0.0 and 0.98 before scaling for Y, 0.4 and 2 of the initial value for v, 0.5 and 1.5 of scaling for $R_2$. For $\chi_{nb}$, the lower and upper bounds were set to the value $\chi_{nb}$ calculated from Eq.46 with Y/v=0.98/0.1 and 0.0/0.1, respectively. The optimization was performed on all clusters jointly. At the start of each optimization, the qBOLD term in Eqs.48 and 49 was normalized by $\sqrt{|S(TE_1)|^2} \cdot N_{voxel} \cdot N_{TE}$ to compensate for the scale of the input MRI data, where $\sqrt{|S(TE_1)|}$ is the average of the magnitude of the first echo across the whole brain, $N_{voxel}$ the number of voxels, and $N_{TE}$ the number of echoes. The QSM term in Eq.48 and Eq.49 was also normalized by $\chi^2$. The regularization weighting factor ($\lambda$) and the weighting on the QSM (w) were chosen by performing L-curve analysis: $\lambda$ was first chosen with w=0, then w was chosen with previously decided $\lambda$. The limited-memory Broyden-Fletcher-Goldfarb-Shanno-Bound (L-BFGS-B) algorithm was used for the constrained optimization. The optimization was stopped when the relative residual $$r_n = \frac{E_n - E_{n-1}}{E_n},$$

with $E_n$ the energy of the nth iteration, was smaller than $10^{-5}$ for Eqs. 48 and 49. For the outer kth iteration, the optimization was stopped at $r_k<10^{-3}$. To prevent L-BFGS-B from not updating the Hessian because the residual fell below a preset threshold, the cost function was multiplied by a factor of $10^4$ before L-BFGS-B was started.

Third, the QSM+qBOLD optimization was repeated, but now allowed Y, v, and $R_2$ to vary from voxel to voxel. The cluster-based result was used as the initial guess. The scaling was the same as the cluster-wise optimization. The lower and upper bounds of the rescaled unknowns were set to 0.7 and 1.3 of the initial guesses except for Y to 0.0 and 0.98 before scaling. The same L-BFGS-B algorithm was used as in the cluster-wise optimization. The optimization stopped when the relative residual was smaller than $2\times10^{-4}$ for Eqs. 8 and 9, and $10^{-2}$ for outer iteration.

For Numerical Simulation 1, the same optimization settings were used as in the optimization for the healthy subjects and stroke patients, except for the fixed lower and upper bounds for v, 0.01 and 0.1 before scaling.

The CAT QSM+qBOLD method was compared with the prior QSM+qBOLD method with constant initial guess OEF for the whole brain ("prior QSM+qBOLD" hereafter). For QSM+qBOLD with a constant OEF initial guess based optimization (prior QSM+qBOLD), the optimization is described as follows. The weight on QSM (w) was set to 100 for healthy subjects and stroke patients based on L-curve analysis. The optimization was stopped when the relative residual was smaller than 0.005 for healthy subjects and 0.001 for the stroke patients, lower and upper bounds were set to the same as those used for the clustering method.

All algorithms were implemented in Matlab R2016a (Mathworks Inc., Natick, MA).

Statistical Analysis

ROI analyses (mean and standard deviation) and paired t-tests were performed to compare CMRO2 and OEF values between the prior QSM+qBOLD and CAT QSM+qBOLD. For the ROIs in the healthy subjects, cortical gray matter (CGM) masks were constructed based on T1-weighted images by an experienced neuroradiologist (S.Z. 7 years of experience). For the stroke patients, masks for the lesion and its corresponding contralateral side were constructed based on DWI by an experienced neuroradiologist (S.Z. 7 years of experience). To investigate the resulting dependency on the number of clusters, conventional k-means was performed where K=1, 5, 10, 15, 20 and the x-means' result (K=13 in a healthy subject and K=16 in a stroke patient, 6 days post-onset). The CAT QSM+qBOLD was subsequently performed for each K. The same optimization scheme was used as in the healthy subjects and stroke patients including $$\frac{w}{\lambda} = 5 \times 10^{-3}/1000.$$

To investigate the OEF difference among different K values, a repeated measures ANOVA was performed 5.4. Results In the optimal number of clusters determined by x-means, the difference between the 10% sub-sampling scheme and 100% sampling was on average<1 in 11 healthy subjects and 5 stroke patients (N=16). The 10% sub-sampling scheme (including the 10 trials) was 5-10 times faster than 100% sampling. The optimal number of clusters by the x-means method was 10±2 in healthy subjects (N=11) and 16±0 in stroke patients (N=5).

In the L-curve analysis, the corners for 4 randomly chosen subjects (2 healthy subjects and 2 stroke patients) are commonly located at $\lambda=1000$ and $w=5\times10^{-3}$. FIG. 27a shows the influence of SNR on the sensitivity of the estimated Y on the initial guess in the numerical simulation. Without noise, the relative error is low, but as SNR decreases from 1000 to 50, the relative error tends to increase when the initial guess deviates from the ground truth. For instance, at SNR 50, the relative error was 7.5% when $Y_0=0.6$ and $v_0=0.03$, but it was 29.1% when $Y_0=0.1$ and $v_0=0.03$.

FIG. 27b shows the comparison of the OEF maps obtained using the prior QSM+qBOLD and CAT QSM+qBOLD methods in the simulated stroke brain. CAT QSM+qBOLD provides a more accurate OEF map than the prior QSM+qBOLD, especially at low SNRs. For instance, at SNR 50, CAT QSM+qBOLD captures the low OEF area, whereas the prior QSM+qBOLD is not sensitive to low OEF values. CAT QSM+qBOLD provides lower RMSE than the prior QSM+qBOLD for all SNRs.

Figure 28:
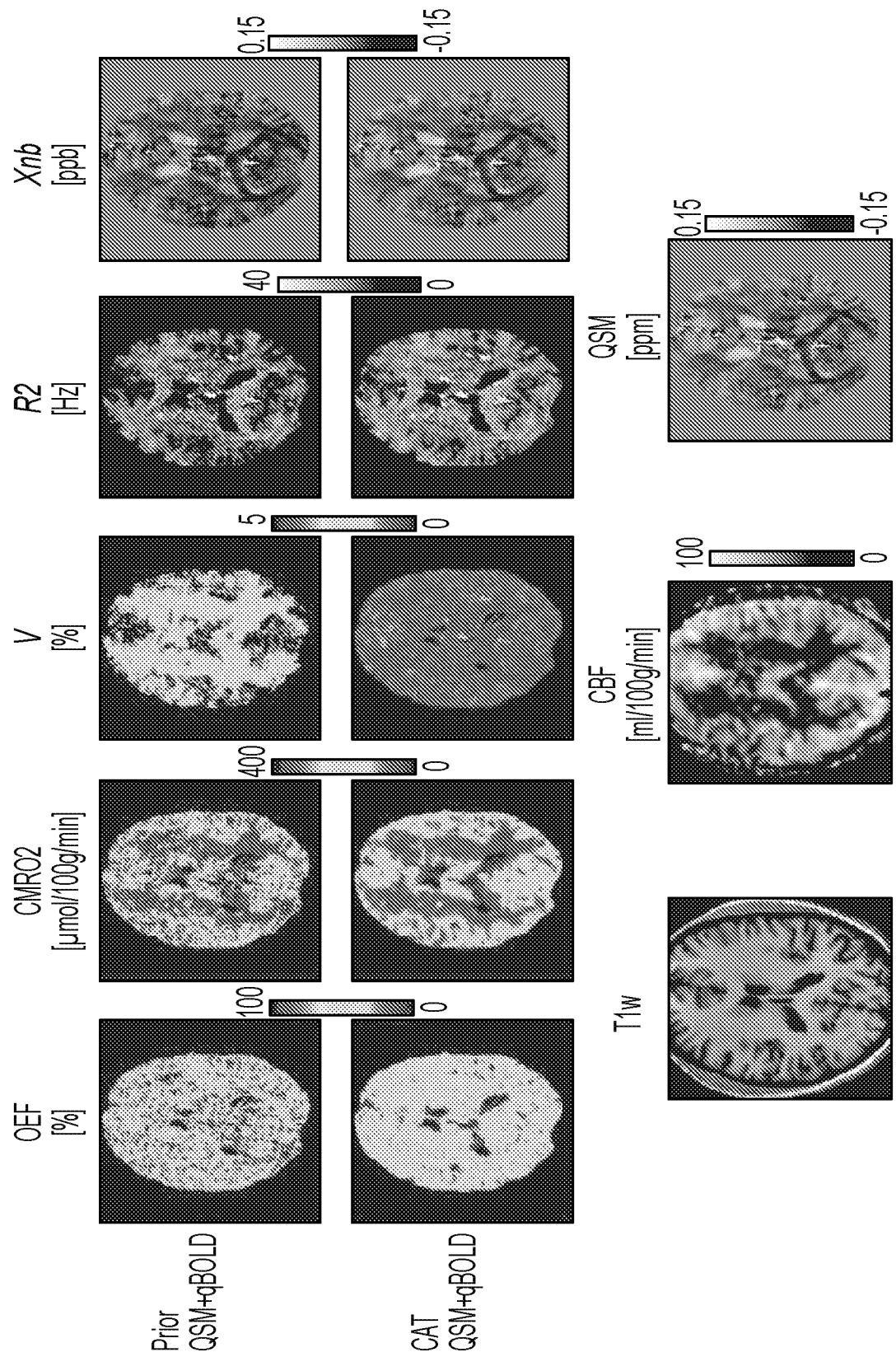
FIG. 28. Comparison of OEF, CMRO2, v, $R_2$, and $\chi_{nb}$ maps between the constant OEF initial guess based QSM+qBOLD (prior QSM+qBOLD) and the CAT-based QSM+qBOLD in a healthy subject. The CAT QSM+qBOLD shows a less noisy and more uniform OEF, and a good CMRO2 contrast between cortical gray matter and white matter without extreme values. The corresponding anatomy as depicted on a T1-weighted image, CBF map and susceptibility map are shown for reference.

FIG. 28 shows a comparison between prior QSM+qBOLD and CAT QSM+qBOLD. The OEF appears less noisy and more uniform, whereas the prior QSM+qBOLD is noisy and has extreme values, for example >80% in deep gray matters. CAT QSM+qBOLD shows a good CMRO2 contrast between CGM and WM without the presence of extreme values seen in the previous method. In the new method, v shows CGM/WM contrast and generally has lower values than the prior QSM+qBOLD.

Figure 29:
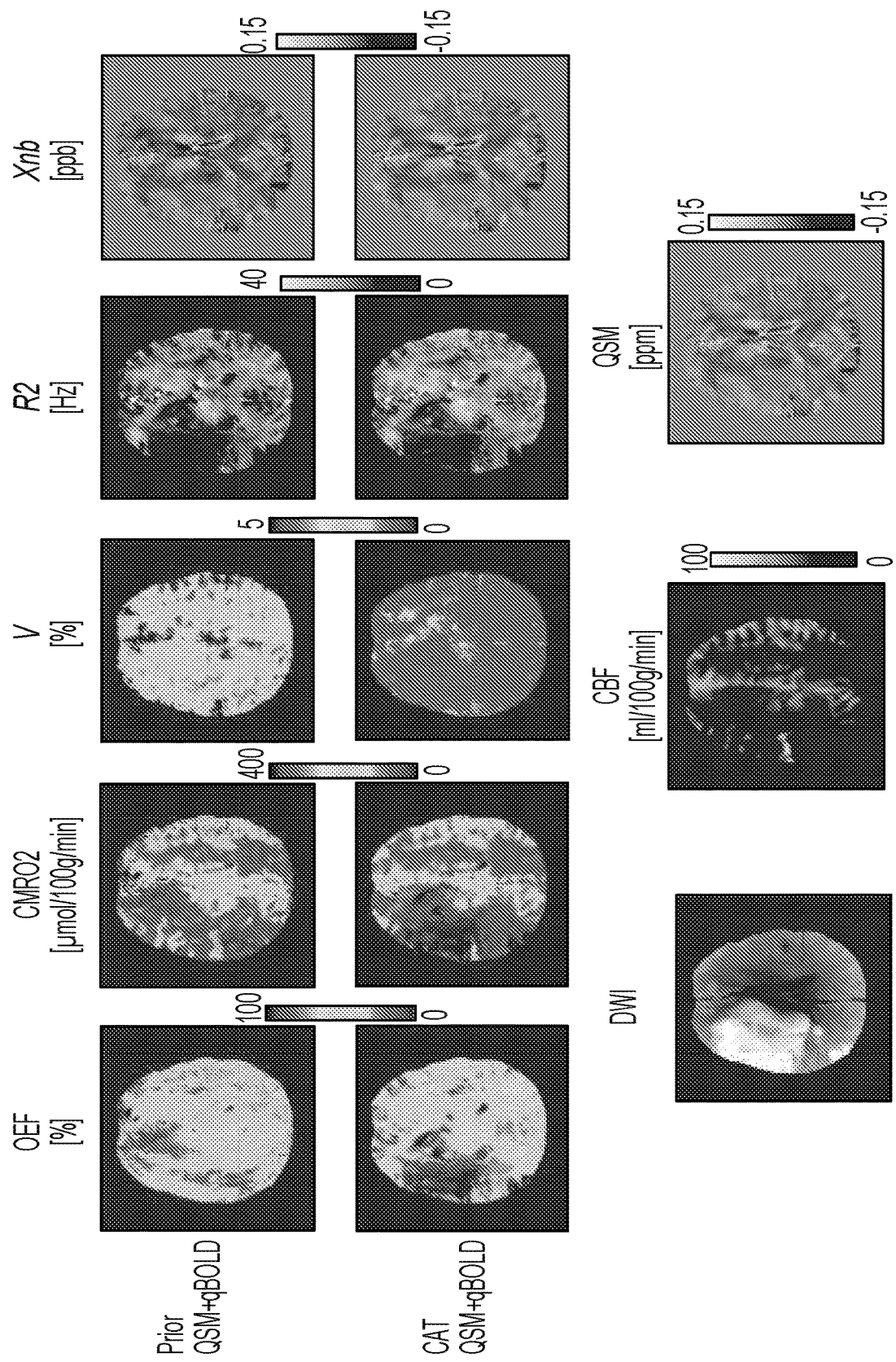
FIG. 29. Comparison of OEF, CMRO2, v, $R_2$, and $\chi_{nb}$ maps between the constant OEF initial guess based QSM+qBOLD (prior QSM+qBOLD) and the cluster analysis of time evolution (CAT)-based QSM+qBOLD in a stroke patient imaged 6 days post stroke onset. In the CMRO2 and OEF maps, the lesion can be distinguished more clearly with the CAT QSM+qBOLD. For CAT QSM+qBOLD, a low OEF area is clearly visualized and contained with the lesion area as defined on DWI, but a low OEF area obtained with the prior QSM+qBOLD method is not as well localized nor contained within the lesion as defined on DWI. The CAT QSM+qBOLD generally shows lower v in the DWI-defined lesion. The contrast in v in the prior QSM+qBOLD result is similar in appearance to that of CBF. The CAT QSM+qBOLD shows generally higher $R_2$ and $\chi_{nb}$ maps than the prior QSM+qBOLD.

FIG. 29 shows the OEF, CMRO2, v, $R_2$, and $\chi_{nb}$ maps in one stroke patient (imaged 6 days post stroke onset) using both the previous and the CAT QSM+qBOLD methods. In the OEF and CMRO2 maps, the lesion can be distinguished more clearly with the CAT QSM+qBOLD. The CAT QSM+qBOLD low OEF area is clearly contained within the lesion as defined on DWI. However, the prior QSM+qBOLD does not show a clearly localized low OEF area, neither within nor outside of the DWI-defined lesion. CAT QSM+qBOLD generally shows low v regions specific to the DWI defined lesion, while the prior QSM+qBOLD method shows similar v contrast to the one of CBF. CAT QSM+qBOLD shows generally higher $R_2$ and $\chi_{nb}$ maps than the prior QSM+qBOLD.

Figure 30:
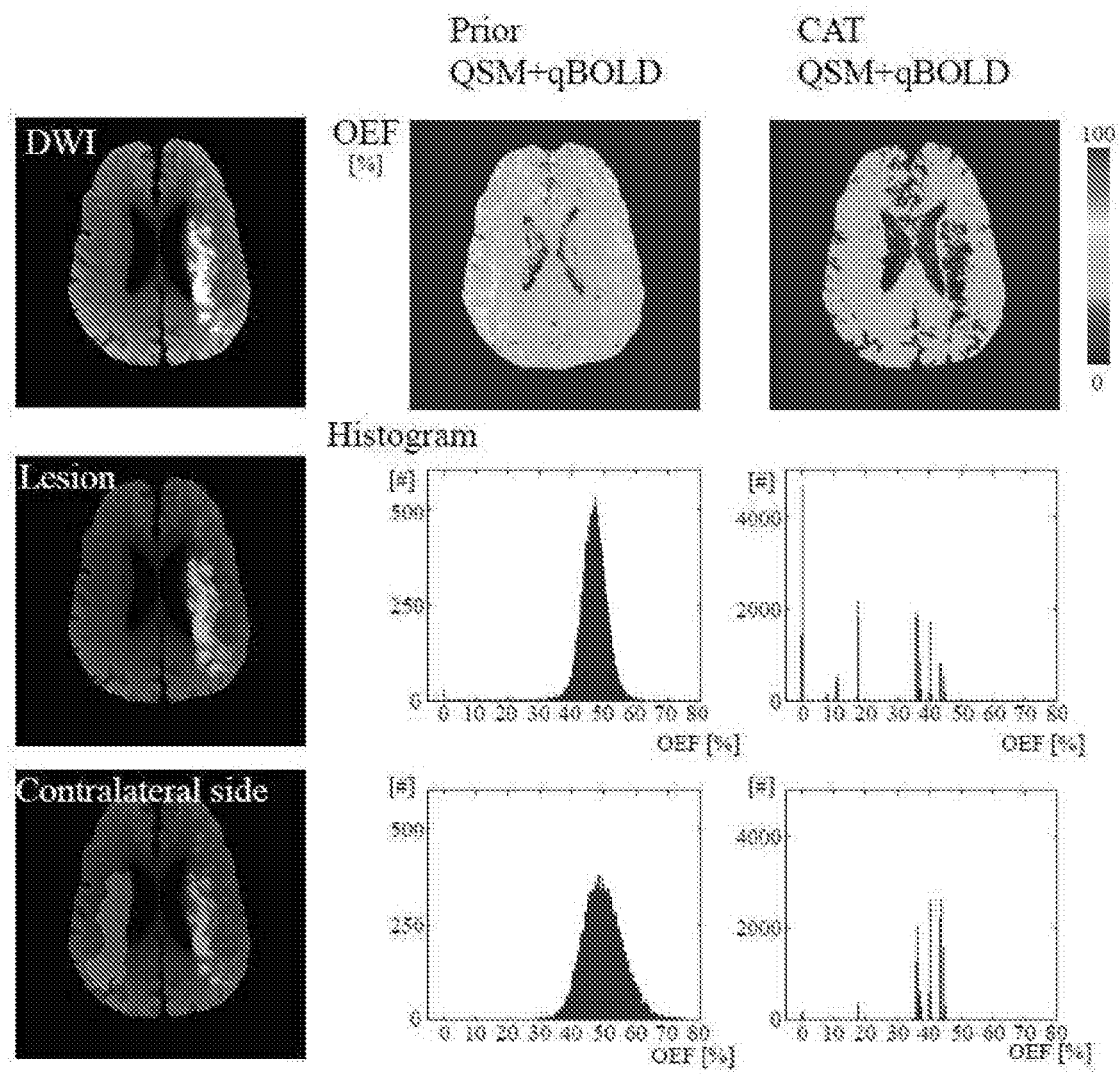
FIG. 30. The histogram of OEF values in the lesion and its contralateral side in a second stroke patient imaged 12 days post stroke onset. The CAT QSM+qBOLD shows a different distribution in the lesion as compared to mirror side. The lesion shows 8 peaks with the strongest two peaks at 0 and 17.5%, while the contralateral side has 6 peaks with dominant peaks at 35~45%. However, the prior QSM+qBOLD does not have a distribution specific to low OEF values in the lesion, but there are bell-shaped distributions for both the lesion and contralateral side (broader in the contralateral side) with peaks at 47% and 49%, respectively.

FIG. 30 shows the histogram of OEF values in the lesion and its contralateral region for both the previous and CAT QSM+qBOLD in a second stroke patient (imaged 12 days post stroke onset). The OEF for CAT QSM+qBOLD is distributed differently in the lesion as compared to the contralateral side. The lesion shows 8 peaks with the strongest two peaks at 0 and 17.5%, while the contralateral side has 6 peaks with dominant peaks at 35~45%. However, the prior QSM+qBOLD does not have a distribution specific to low OEF values in the lesion, but there are bell-shaped distributions for both the lesion and contralateral side (broader in the contralateral side) with peaks at 47% and 49%, respectively.

Figure 31:
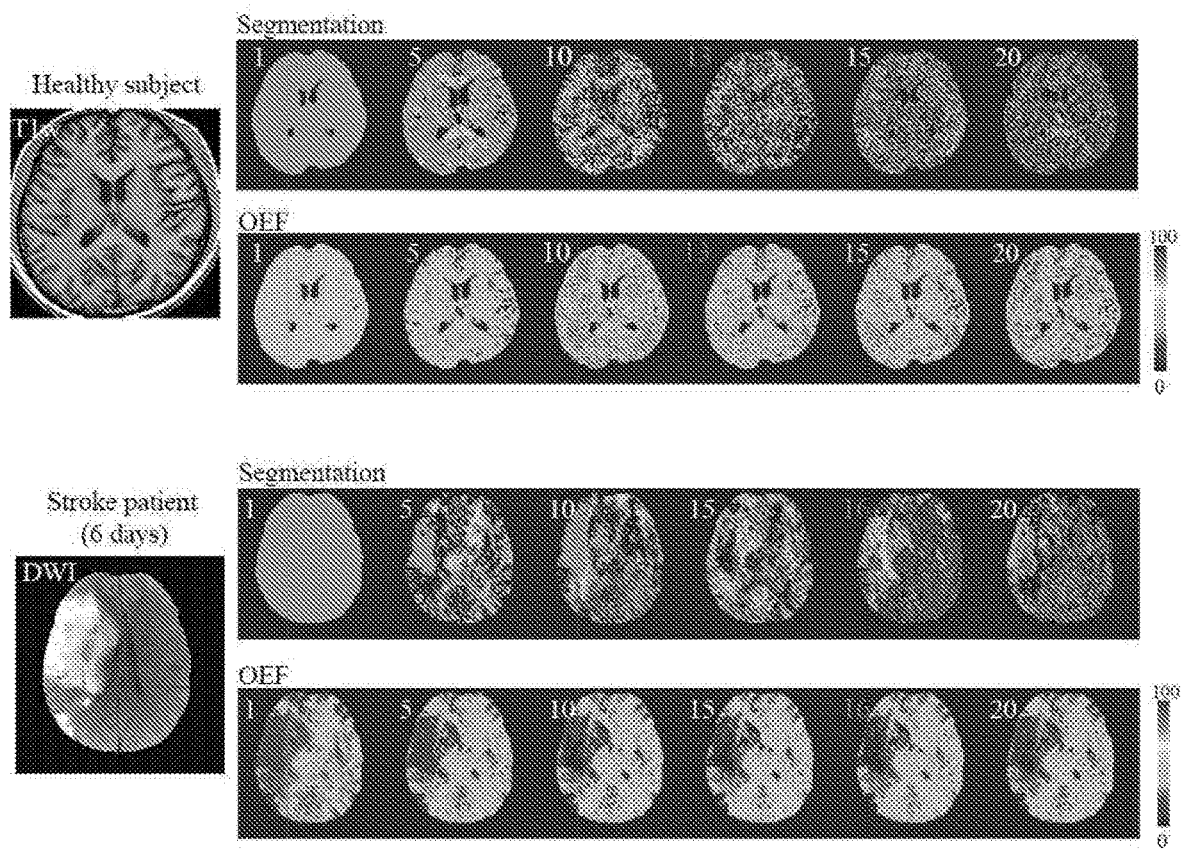
FIG. 31. The segmentations and resultant OEF maps using a different number of clusters (K=1, 5, 10, 15, 20, as well as the x-means result) in a healthy subject and a stroke patient (6 days post stroke onset). In the segmentations, different colors indicate different clusters. The resulting OEF appearance is nearly constant for K>5. The x-means method selected K=13 for the healthy subject and K=16 for the stroke patient (indicated in red).

In FIG. 31, the segmentations and resulting OEF maps are shown for a range of cluster numbers (K=1, 5, 10, 15, 20 and the x-means result in a healthy subject and a stroke patient (6 days post stroke onset)). The resultant OEF maps have a similar appearance for all K larger than 5, and were not significantly different among the Ks: p=1.0000, F(5, 5750075)=0.0022 for the healthy subject and p=0.9999, F(5, 12209016)=0.0152 for the stroke patient (repeated measures ANOVA). The x-means clustering automatically chose K=13 for the healthy subject and K=16 for the stroke patient.

Figure 32:
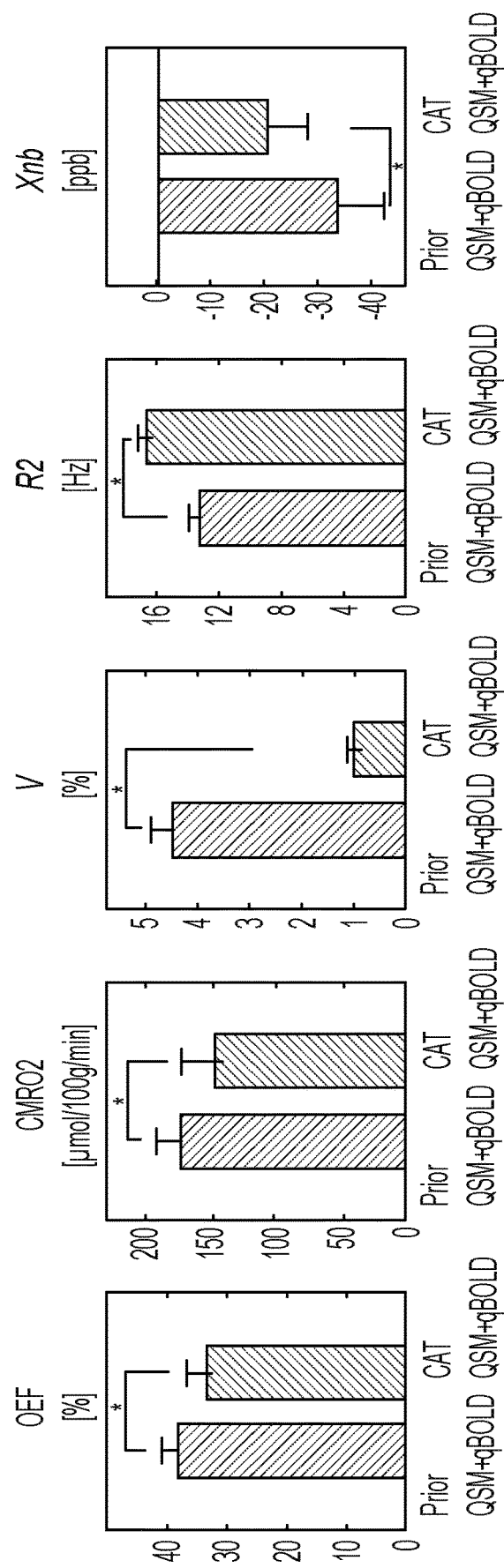
FIG. 32. Average and standard deviation of OEF, CMRO2, v, $R_2$, and $\chi_{nb}$ maps between the constant OEF initial guess based QSM+qBOLD (prior QSM+qBOLD) and the cluster analysis of time evolution (CAT) QSM+qBOLD in cortical gray matter from healthy subjects (N=11). The CAT QSM+qBOLD shows smaller average CMRO2, OEF and v than the prior QSM+qBOLD, but CAT QSM+qBOLD shows higher average $R_2$ and $\chi_{nb}$ values. * p<0.01 (paired t-test).

FIG. 32 shows the ROI analysis in the cortical gray matter (CGM) of healthy subjects between the previous QSM+qBOLD and CAT QSM+qBOLD. The CAT QSM+qBOLD shows smaller OEF, CMRO2 and v compared to the prior QSM+qBOLD: OEF is 32.7±4.0% and 37.9+3.1% (p<0.01), CMRO2 is 148.4+23.8 and 171.4+22.4 μmol/100 g/min (p<0.01), v is 1.00±0.2% and 4.45±0.39% (p<0.01). In comparison, CAT QSM+qBOLD shows higher $R_2$ and $\chi_{nb}$ values: $R_2$ was 16.5±0.5 Hz and 13.1±0.7 Hz (p<0.01), $\chi_{nb}$ is −20.2±8.1 ppb and −33.8±9.0 ppb (p<0.01).

5.5. Conclusions

The results demonstrate that the cluster analysis of time evolution (CAT)-based QSM+qBOLD method provides more a uniform and less noisy OEF map in healthy subjects than the prior QSM+qBOLD method. The low OEF areas are contained within the DWI-defined lesions of stroke patients, while no such clear pattern was observed using the previous QSM+qBOLD method. By using clustering to increase the effective SNR significantly, the prior QSM+qBOLD model obtained more accurate OEF maps in simulations. Finally, the CAT QSM+qBOLD estimates OEF from GRE data only, while the prior QSM+qBOLD method relied on CBF measurements.

Compared to the prior QSM+qBOLD method, OEF maps obtained using the new proposed method are more uniform and have less extreme values in healthy subjects (FIG. 28), in agreement with previous PET studies. The suppressed noise is likely due to the use of cluster-wise optimization, in which unknowns are assumed to be constant throughout the cluster, thereby creating an effective signal averaging. The simulations suggest that the resulting higher SNR makes the estimated parameters less sensitive to measurement error. The overall noise reduction in Y and v propagate into $\chi_{nb}$ and $R_2$ maps with reductions in noise as well, compared to the prior QSM+qBOLD method (FIG. 28).

CAT QSM+qBOLD shows smaller OEF values (FIGS. 27c and 32), e.g. 32.7±4.0% and 37.9±3.1% (p<0.01) in CGM for CAT and pre QSM+qBOLD, respectively. Both OEF values fall within the range previously reported for OEF obtained using PET: 35±7% and 40±9%, and with other MRI based techniques: 26±2%, 31.7±6.1%, 35±4%, and 38±14%. The smaller OEF values in the CAT QSM+qBOLD method are accompanied by higher $R_2$, as compared to the prior QSM+qBOLD method (16.5±0.5 Hz vs. 13.1±0.7 Hz). This is expected since, in order to obtain the same measured magnitude signal decay, OEF decreases if $R_2$ increases (Eqs.43 and 44).

The CAT QSM+qBOLD method shows smaller v values in healthy subjects compared to the prior QSM+qBOLD method: 1.00±0.2% vs 4.45±0.39 (p<0.01) in CGM. Compared to PET and other MR techniques, the v from the CAT and prior QSM+qBOLD is a bit smaller and larger, respectively: the v values obtained using PET, e.g. 1.9±0.5% and 2.0±0.2%, and other MR techniques: 1.75±0.13%, 1.9±0.5 2.46±0.28, 2.68±0.47%, 3.6±0.4%. Also, the new method shows greater $R_2$: 16.5±0.5 Hz and 13.1±0.7 Hz for CGM, which agrees well with the values calculated from other MR techniques, 14.9±0.2 Hz, 15.1±0.6 Hz, 17.1±2 Hz.

In ischemic stroke patients, low OEF regions obtained by CAT QSM+qBOLD are largely contained within the lesions defined by DWI (FIGS. 29 and 30), however, the OEF maps obtained by the prior QSM+qBOLD method did not identify the lesion. The low v area by CAT QSM+qBOLD generally agrees with the location of the lesion; this observation is consistent with the decrease in blood volume that occurs in ischemic stroke lesions. In contrast, the prior QSM+qBOLD method utilized a constant OEF initial guess, and the v map contrast was similar to that of the CBF map (FIG. 29). This indicates that the v result did not change much from the initial guess, which is based on the CBF through a phenomenological relationship.

In a stroke patient imaged 12 days post stroke onset, CAT QSM+qBOLD shows an OEF histogram from the lesion that is distinct from that of the contralateral region (FIG. 30): in the new method, there were the strongest two peaks OEF at 0% and 17.5%, and several peaks at high OEF at 35-45% which was similar to the contralateral normal OEF. This region of low OEF may indicate a region of dead tissue (OEF<10%), and another region with salvageable tissue (35-45%). The prior QSM+qBOLD results show no specific distribution specific to low OEF values in the lesion. These results suggest that the use of CAT makes QSM+qBOLD increasingly sensitive to the low OEF values that are expected in stroke lesions.

The described CAT QSM+qBOLD method can be further improved. The proper number of clusters was chosen automatically by the x-means method. This is based on a well-known metric, BIC. However, the optimal number of clusters might be different when using different metrics, e.g. Akaike information criterion. More generally, the clustering result might be different when using a different clustering method, e.g. hierarchical clustering. This might affect the resulting OEF map. In the study, the OEF map was not sensitive to the number of clusters (FIG. 31) chosen for k-means clustering. Furthermore, the voxel-wise optimization was performed after the cluster-wise optimization, which may alleviate the consequences of the imperfect clustering.

The optimization problem Eq.45 can be solved using deep learning. An artificial neural network (ANN) such as the U-Net described above can be trained by simulated data over a range of Y, v, $R_2$, $S_0$, $\chi_{nb}$ values covering all possible pathophysiological values for these parameters.

As reported here, the simulation can be performed according to Eqs.43 & 46 and other relevant MRI signal equations with Gaussian noise added to simulated complex data. The simulated complex multiecho MRI data approximating data obtained from patients is input for ANN, and Y, v, $R_2$, $S_0$, $\chi_{nb}$ as "label" of MRI data are output for ANN. As known from deep learning, the numerous weights in ANN would learn sparse representation of the MRI signal magnitude evolution over echo time and other feature and provide optimal denoising or robustness against noise. Then the trained ANN can be used an mGRE dataset acquired from a subject to generate OEF.

To improve CMRO2 estimation accuracy, CBF measurement accuracy should be increased as well. The ASL-measured CBF used in this study is low resolution (compared the gradient echo acquisition) and known to be less accurate in WM. OEF and v estimations in large veins might be inaccurate as they were treated in the same way as normal brain tissue, which could be mitigated by using v=1 for large veins. However, this would require prior segmentation of large veins, which has been done using thresholding the susceptibility map, similar to what was done in this study to segment the SS. The CAT QSM+qBOLD optimization is still non-linear, which means that convergence may be affected by solver implementation, parameter scaling, and stopping criterion. Finally, no ground truth or reference measurement was available, so a O15 PET study on a PET-MR scanner is needed to show accuracy in vivo.

In conclusion, the study demonstrated the feasibility of the cluster analysis of time evolution (CAT) for QSM+qBOLD in healthy subjects and in ischemic stroke patients, by effectively improving SNR. In simulations, the proposed method was more accurate than the prior QSM+qBOLD method. The CAT QSM+qBOLD provides a less noisy and more uniform OEF in healthy subjects. In ischemic stroke patients, low OEF areas are contained with the stroke lesion. CAT QSM+qBOLD may be readily applied to investigate tissue viability in various diseases, such as Alzheimer's disease, multiple sclerosis, tumor, and ischemic stroke.

6. Device System Implementation

Figure 33:
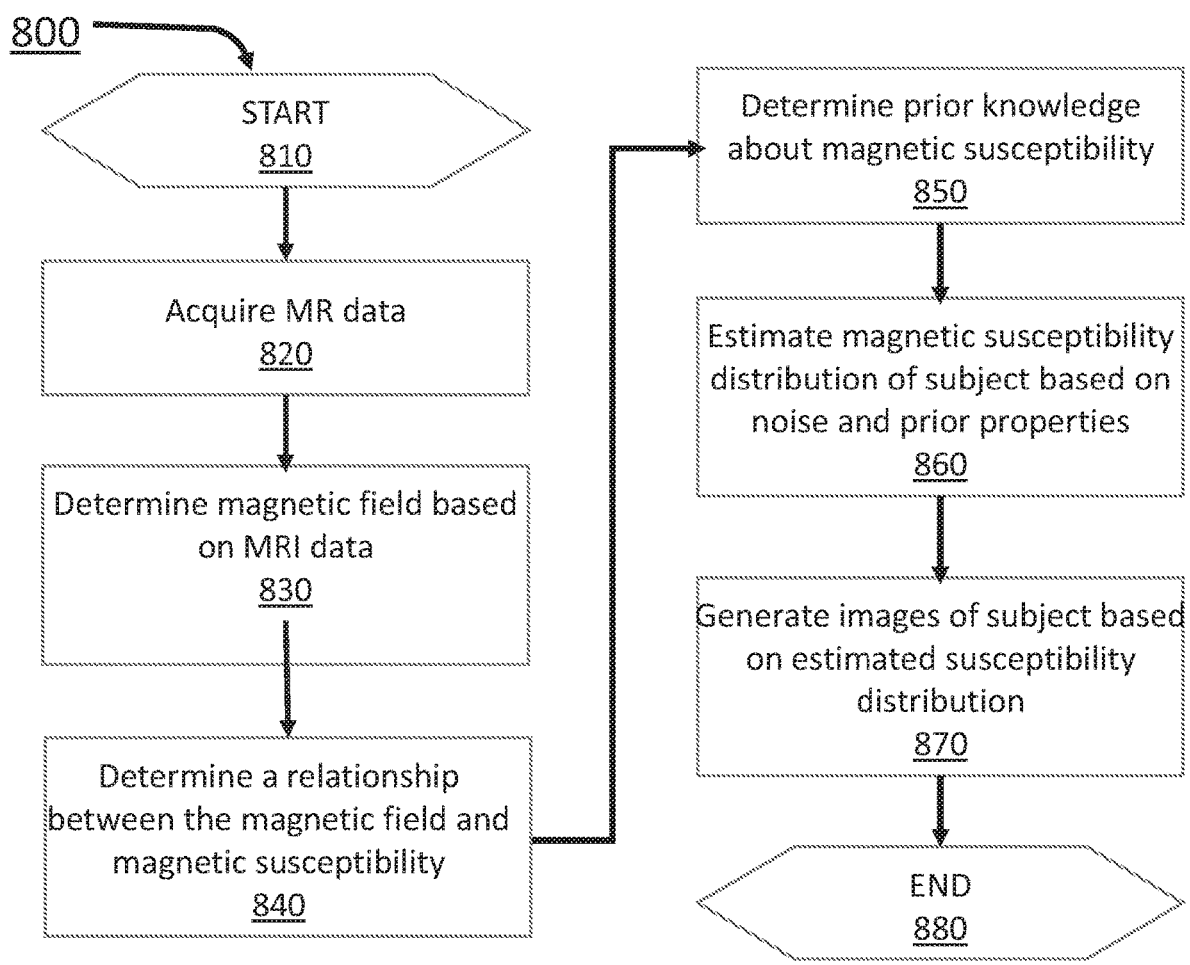
FIG. 33 shows an example process for a) mapping tissue magnetic susceptibility, b) mapping tissue transport parameters, and c) generating multiple contrast images.
Figure 33:
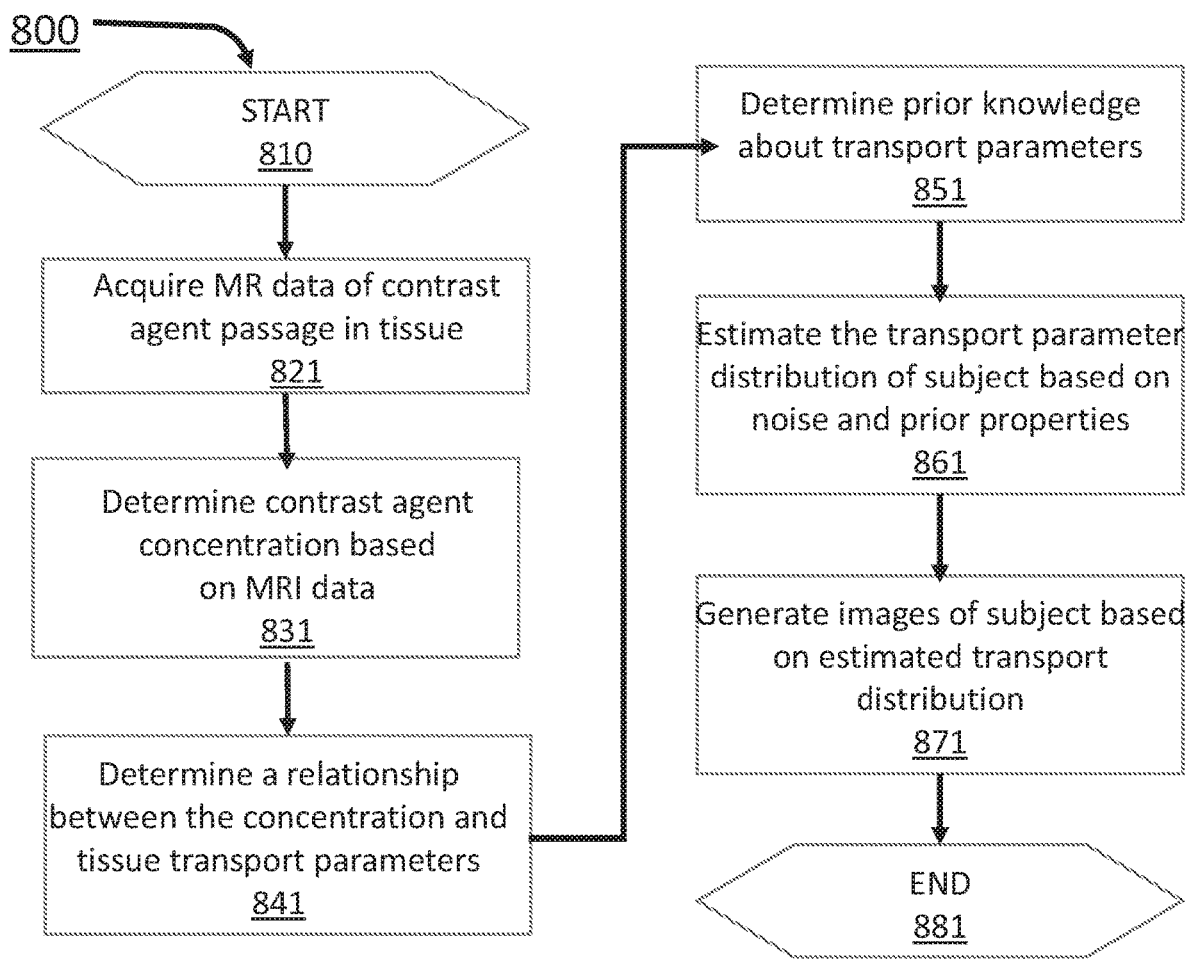
Figure 33:
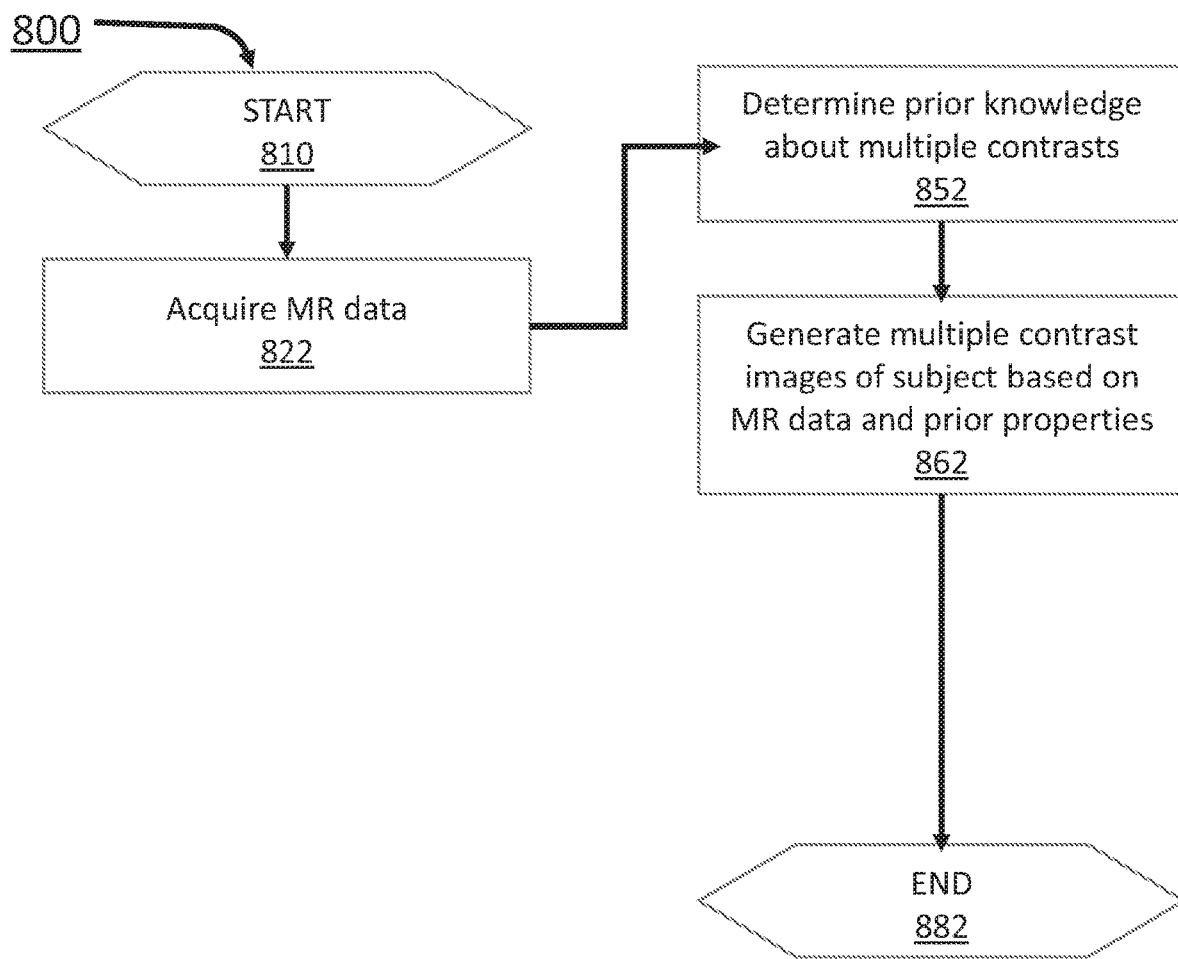

In some cases, one or more of the above quantitative mapping techniques can be implemented using the process 800 shown in FIG. 33. As an example, the process 800 can be used to map the tissue magnetic susceptibility of a subject, such as a patient (or portion of a patient) or an experimental sample (e.g., an imaging phantom, a sample of material or tissue, and so forth). In some implementations, the process 800 can be used to transform magnetic resonance (MR) signal data corresponding to a subject into multiple images that quantitatively depict the structure and/or composition and/or function of the subject. As an example, in some cases, the process 800 can be used to obtain multiecho MR data corresponding to a subject, and process this multiecho MR data to generate a quantitative susceptibility map of the subject. As another example, in some cases, the process 800 can be used to obtain rapidly undersampled multiple contrast MR data corresponding to a subject, and process this data to generate multiple contrast MR images. As another example, in some cases, the process 800 can be used to obtain time-resolved MR data corresponding a subject as a contrast agent passing through tissue in an organ of the subject, and process this time-resolved MR data to generate a quantitative transport map of the subject. Using these quantitative maps of physical properties and multiple contrasts, one or more images of the subject can be generated and displayed to a user. he user can then use these images for diagnostic, therapeutic or experimental purposes, for example to investigate the structure and/or composition and/or function of the subject, and/or to diagnose various conditions or diseases based, and/or to treat various conditions or diseases based, at least in part, on the images. As the process 800 can result in maps of physical quantities having higher quality and/or accuracy compared to other mapping techniques, implementations of the process 800 can be used to improve a user's understanding of a subject's structure and/or composition and/or function, and can be used to improve the accuracy of any resulting medical diagnoses, treatments or experimental analyses.

The process 800 begins by acquiring MR data corresponding to a subject (step 810). In some cases, the MR data can correspond to a patient (e.g., the entirety of a patient or a portion of a patient, such as a particular portion to the patient's body). In some cases, the MR data can correspond to one or more samples (e.g., an imaging phantom, a sample of one or more materials, a sample of one or more types of tissue, and/or one or more other objects).

In some implementations shown in FIG. 33a, the MR data can be acquired using an MRI scanner using one or more suitable pulse sequences. As an example, in some cases, MR data can be acquired using a gradient echo sequence that acquires MR data at a single echo time or at multiple echo times (e.g., two, three, four, five, and so forth). Various scan parameters can be used. As another example, MR data can be obtained using a 3D multi-echo spoiled gradient echo sequence on a 3 T scanner (e.g., a GE Excite HD MR scanner) using a pulse sequence that samples at different echo times (TE) (e.g., 4 TEs, such as 3.8, 4.3, 6.3 and 16.3 ms) in an interleaved manner, and with following imaging parameters: repetition time (TR)=22 ms; voxel size=. 5×0.5×0.5 mm$^3$, matrix size=256×64×64; bandwidth (BW) ±31.25 kHz; flip angle=15°. As another example, MR data can be obtained using a 3D multi-gradient echo sequence on a 3 T scanner using imaging parameters TE/ΔTE/#TE/TR/FA/BW/FOV/matrix size=5 ms/5 ms/8/50 ms/20°/±62.50 kHz/21.8×24×12.8 cm$^3$/232×256×64. Although an example sequences and example parameters are described above, these are merely illustrative. In practice, other sequences and parameters can be used, depending on various factors (e.g., the size of region to be examined, a known or assumed range of susceptibility values of the subject, scan time considerations, device limitations, and so forth).

After acquiring MR data corresponding to a subject, the process 800 continues by determining a magnetic field based on the MR data (step 820). As noted above, in some cases, the MRI signal phase is affected by the magnetic field corresponding to the magnetic susceptibility distribution of the subject and the chemical shift of tissue components.

The magnetic field can be determined from the complex MRI data by fitting the detected signal as a sum over tissue spectral components, where each component signal characterized by an exponent with a negative real part representing signal decay and an imaginary part representing phase dependent on the magnetic field and the chemical shift (step 830). This fitting for such a complex signal model can be performed on iteratively using numerical optimization. A robust initialization for numerical optimization can be estimated using a simplified single species model and graph cut separating smooth field against chemical shift and phase unwrapping.

After determining the magnetic field based on the MR data, the process 800 continues by determining a relationship between the magnetic field and magnetic susceptibility (step 840). As described above, in some implementations, the relationship between the magnetic field and magnetic susceptibility can be expressed as a relationship between the magnetic field at a given location to the magnetic susceptibility at that location. In some implementations, this field-susceptibility relationship can be expressed in integral form, or in differential form. In the differential form, the relationship between the magnetic field at a given location to the magnetic susceptibility at that location can include an equation where a Laplacian of the magnetic field equals one third of the Laplacian of the magnetic susceptibility minus a second order derivative of the magnetic susceptibility. In some implementations, this field-susceptibility relationship can be expressed in the weights of an artificial neural network.

After determining a relationship between the magnetic field and magnetic susceptibility, the process 800 continues by determining prior knowledge about tissue magnetic susceptibility distribution (step 850). One estimation of tissue susceptibility distribution is to use R2* values derived from the magnitude signal. High R2* values can be used to identify high susceptibility regions such as hemorrhages for preconditioning to accelerate the convergence of numerical optimization. An example of preconditioning is to separate the whole image volume into region with high susceptibility (including hemorrhages, air regions and background) and region with normal tissue susceptibility. Such preconditioning reduces the susceptibility search range and hence accelerates convergence. Another estimation of tissue susceptibility distribution is to use low (near zero) R2* regions for identifying regions of pure water such as cerebrospinal fluid in the ventricles in the brain, oxygenated arterial blood in the aorta, or regions of pure fat in the abdominal wall. As water and fat have known susceptibility values, they can be used to serve zero references (to water) to generate absolute susceptibility values using a minimal variance regularization.

After obtaining the susceptibility prior information and signal data noise property, the process 800 continues by estimating a magnetic susceptibility distribution of the subject based, at least in part, on the prior information and data noise property (step 860). In some implementations as described above, estimating the susceptibility distribution of the subject through optimization can include determining a cost function corresponding to a susceptibility distribution, the magnetic field, masks corresponding to regions of interest. The cost function includes a data fidelity term based on data noise property expressing the relationship between the magnetic field and tissue susceptibility in an integral or differential form, and a regularization term expressing prior information. The estimated susceptibility distribution of the subject can be determined by identifying a particular susceptibility distribution that minimizes one or more of these cost functions. As described above, in some implementations, this can be determined numerically using quasi Newton, alternating direction method of multipliers, or artificial neural network.

After estimating a magnetic susceptibility distribution of the subject, the process 800 continues by generating one or more images of the subject based on the estimated susceptibility distribution of the subject (step 870). These images can be electronically displayed on a suitable display device (e.g., an LCD display device, LED display device, CRT display device, or other display device that can be configured to show images) and/or physically displayed on a suitable medium (e.g., printed, etched, painted, imprinted, or otherwise physically presented on a sheet or paper, plastic, or other material). In some cases, the estimated susceptibility distribution of the subject can be visualized using a color scale, where each of several colors is mapped to a particular susceptibility value or range of susceptibility values. Accordingly, a two dimensional or three dimension image can be generated, where each pixel or voxel of the image corresponds to a particular spatial location of the subject, and the color of that pixel of voxel depicts the susceptibility value of the subject at that location. In some cases, the color scale can include a gradient of colors and/or a gradient of gray shades (e.g., a gray scale), in order to depict a range of susceptibility values. In some cases, for a color scale that includes a gradient of colors or a gradient of gray shades, one end of the gradient can correspond to the lowest susceptibility value in a particular window of susceptibility values (e.g., an arbitrarily selected window of values), and the other end of the gradient can correspond to the highest susceptibility value in the window of values. For instance, for gray scale that includes a gradient of gray shades between pure white and pure black, pure white can be used to indicate the highest susceptibility value in a particular arbitrary window of values, and pure black can be used to indicate the lowest susceptibility value in the window of values. Other relationships between a color/gray scale and susceptibility values is also possible. For example, in some cases, for gray scale that includes a gradient of gray shades between pure white and pure black, pure white can be used to indicate the lower susceptibility value in a particular arbitrary window of values, and pure black can be used to indicate the highest susceptibility value in the window of values. Although the examples are described in the context of gray scales, in practice, similar relationships between color scales and susceptibility values are also possible. Susceptibility values and colors can be mapped linearly (e.g., such that each absolute change in susceptibility value corresponds to a proportional change in color), logarithmically (e.g., such that each an exponential change in susceptibility value correspond to a linear change in color), or according to any other mapping. Although examples mapping between color scales and susceptibility values are described above, these are merely illustrative examples. In practice, other mappings are also possible, depending on the implementation.

In some implementations shown in FIG. 33b, the MR data can be acquired using an MRI scanner using one or more suitable pulse sequences repeatedly in a time-resolved manner during a contrast agent passage through tissue. As an example, in some cases, MR data can be acquired using a gradient echo sequence that acquires MR data at a single echo time with many time frames. Various scan parameters can be used. As another example, MR data can be obtained using a 3D spoiled gradient echo sequence on a 3 T scanner (e.g., a GE Excite HD MR scanner) with the following imaging parameters: 0.94×0.94×5 mm3 voxel size, 256× 256×16-34 matrix, 13-25° flip angle, 1.21-1.35 ms TE, 4.37-5.82 ms TR, 6.2-10.2 s temporal resolution and 30-40 time points. Although an example sequence and example parameters are described above, these are merely illustrative. In practice, other sequences and parameters can be used, depending on various factors (e.g., the size of region to be examined, a known or assumed range of susceptibility values of the subject, scan time considerations, device limitations, and so forth).

After acquiring MR data corresponding to a subject, the process 800 continues by determining contrast agent concentration based on the MR data (step 821). As noted above, in some cases, the MRI signal magnitude and phase are affected by the magnetic field corresponding to the magnetic susceptibility distribution of the highly paramagnetic contrast agent.

The contrast agent concentration at each time frame can be determined from the complex MRI data: QSM processing of the phase data, magnitude signal model fitting, or combining both (step 831). This fitting data to a complex signal model to extract agent concentration can be performed using numerical optimization.

After determining the agent or tracer concentration based on the MR data, the process 800 continues by determining a relationship between the tracer concentration and the underlying transport parameters (step 841). As described above, in some implementations, the concentration—transport relationship can be expressed as a relationship between the concentration at a given location to the transport parameters at that location, which includes the temporal change of concentration and the divergence of the mass flux. In some cases, the mass flux is the concentration times multiplied by a velocity of convection or drift.

After determining a relationship between the tracer concentration and the transport parameters (including velocity, diffusion, permeability and pressure gradient), the process 800 continues by determining prior knowledge about tissue transport parameter distribution (step 851). One estimation of tissue transport parameter distribution in space is tissue morphological information. In some cases, the velocity distribution can be sparsity characterized by a cost function of an L1 norm of gradient of the velocity spatial distribution. In some cases, tissue transport parameter distribution can be characterized by an artificial neural network.

After obtaining the transport spatial distribution prior information, the process 800 continues by estimating a transport distribution of the subject based, at least in part, on the prior information and concentration data (step 861). As described above, estimating the transport distribution of the subject can include determining a cost function corresponding to a transport-parameter (or transport for simplicity) distribution and the tracer concentration. The cost function includes a data fidelity term based on concentration data noise property and a regularization term expressing prior information. The estimated transport distribution of the subject can be determined by identifying a particular transport distribution that minimizes one or more of these cost functions. As described above, in some cases, this can be determined numerically using quasi Newton, alternating direction method of multipliers, or artificial neural network.

After estimating a transport distribution of the subject, the process 800 continues by generating one or more images of the subject based on the estimated transport distribution of the subject (step 871). These images can be electronically displayed on a suitable display device (e.g., an LCD display device, LED display device, CRT display device, or other display device that can be configured to show images) and/or physically displayed on a suitable medium (e.g., printed, etched, painted, imprinted, or otherwise physically presented on a sheet or paper, plastic, or other material). In some cases, the estimated transport distribution of the subject can be visualized using a color scale, where each of several colors is mapped to a particular transport value or range of transport values. Accordingly, a two dimensional or three dimensional image can be generated, where each pixel or voxel of the image corresponds to a particular spatial location of the subject, and the color of that pixel of voxel depicts the transport value of the subject at that location. In some cases, the color scale can include a gradient of colors and/or a gradient of gray shades (e.g., a gray scale), in order to depict a range of transport values. In some cases, for a color scale that includes a gradient of colors or a gradient of gray shades, one end of the gradient can correspond to the lowest transport value in a particular window of transport values (e.g., an arbitrarily selected window of values), and the other end of the gradient can correspond to the highest transport value in the window of values. For instance, for gray scale that includes a gradient of gray shades between pure white and pure black, pure white can be used to indicate the highest transport value in a particular arbitrary window of values, and pure black can be used to indicate the lowest transport value in the window of values. Other relationships between a color/gray scale and transport values is also possible. For example, in some cases, for gray scale that includes a gradient of gray shades between pure white and pure black, pure white can be used to indicate the lower transport value in a particular arbitrary window of values, and pure black can be used to indicate the highest transport value in the window of values. Although the examples are described in the context of gray scales, in practice, similar relationships between color scales and transport values are also possible. Transport values and colors can be mapped linearly (e.g., such that each absolute change in transport value corresponds to a proportional change in color), logarithmically (e.g., such that each an exponential change in transport values correspond to a linear change in color), or according to any other mapping. Although examples mapping between color scales and transport values are described above, these are merely illustrative examples. In practice, other mappings are also possible, depending on the implementation.

In some implementations shown in FIG. 33c, the MR data can be acquired using an MRI scanner using one or more suitable pulse sequences sensitizing multiple contrasts in tissue (step 822). As an example, in some cases, MR data can be acquired fully for T1 weighted image dataset, but at a small fraction for T2 weighted, T2 FLAIR and diffusion weighted image datasets. Various scan parameters can be used. As another example, MR data can be obtained using a T1 weighted sequence with 256×176 matrix size and 1 mm$^3$ isotropic resolution. Although example sequences and example parameters are described above, these are merely illustrative. In practice, other sequences and parameters can be used, depending on various factors (e.g., the size of region to be examined, a known or assumed range of contrast values of the subject, scan time considerations, device limitations, and so forth).

After acquiring MR data corresponding to a subject, the process 800 continues by determining prior knowledge about tissue structural information or morphology (step 852). One estimation of tissue morphology consistency among images of various tissue contrasts cane be sparsity characterized by a cost function of an L1 norm of gradient of the velocity spatial distribution. In some cases, morphology consistency can be characterized by an artificial neural network.

After obtaining tissue morphology prior information, the process 800 continues by reconstructing images of various contrasts of the subject based, at least in part, on the prior information and undersampled data (step 862). As described above, reconstructing images of the subject from undersampled noisy data can include determining a cost function that includes a data fidelity term based on concentration data noise property and a regularization term expressing prior information. The estimated transport distribution of the subject can be determined by identifying a particular image that minimizes one or more of these cost functions. As described above, in some cases, this can be determined numerically using quasi Newton, alternating direction method of multipliers, or artificial neural network.

After reconstruction images of various weights of the subject, the process 800 continues for displaying one or more images of the subject (step 872). These images can be electronically displayed on a suitable display device (e.g., an LCD display device, LED display device, CRT display device, or other display device that can be configured to show images) and/or physically displayed on a suitable medium (e.g., printed, etched, painted, imprinted, or otherwise physically presented on a sheet or paper, plastic, or other material). In some cases, the reconstructed images of the subject can be visualized using a color scale, where each of several colors is mapped to a particular intensity value or range of intensity values. Accordingly, a two dimensional or three dimensional image can be generated, where each pixel or voxel of the image corresponds to a particular spatial location of the subject, and the color of that pixel of voxel depicts the intensity value of the subject at that location. In some cases, the color scale can include a gradient of colors and/or a gradient of gray shades (e.g., a gray scale), in order to depict a range of intensity values. In some cases, for a color scale that includes a gradient of colors or a gradient of gray shades, one end of the gradient can correspond to the lowest intensity value in a particular window of intensity values (e.g., an arbitrarily selected window of values), and the other end of the gradient can correspond to the highest intensity value in the window of values. For instance, for gray scale that includes a gradient of gray shades between pure white and pure black, pure white can be used to indicate the highest intensity value in a particular arbitrary window of values, and pure black can be used to indicate the lowest intensity value in the window of values. Other relationships between a color/gray scale and intensity values is also possible. For example, in some cases, for gray scale that includes a gradient of gray shades between pure white and pure black, pure white can be used to indicate the lower intensity value in a particular arbitrary window of values, and pure black can be used to indicate the highest intensity value in the window of values. Although the examples are described in the context of gray scales, in practice, similar relationships between color scales and intensity values are also possible. Intensity values and colors can be mapped linearly (e.g., such that each absolute change in intensity value corresponds to a proportional change in color), logarithmically (e.g., such that each an exponential change in intensity values correspond to a linear change in color), or according to any other mapping. Although examples mapping between color scales and intensity values are described above, these are merely illustrative examples. In practice, other mappings are also possible, depending on the implementation.

Figure 34:
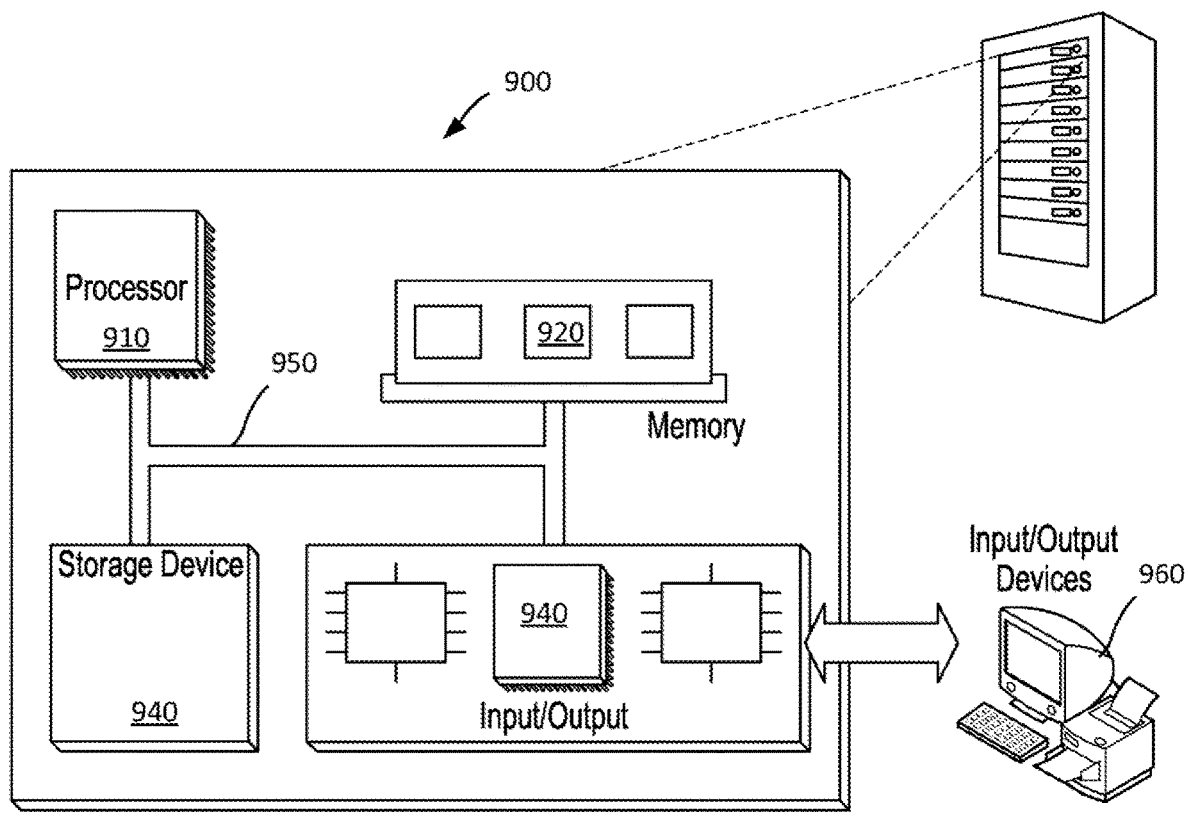
FIG. 34 is a block diagram of an example computer system that may be implemented with the disclosed example systems and methods.

Implementations of the above described techniques can be performed using a computer system. FIG. 34 is a block diagram of an example computer system 900 that can be used, for example, to perform implementations of the process 800. In some implementations, the computer system 900 can be communicatively connected to another computer system (e.g., another computer system 900), such that it receives data (e.g., MRI datasets), and analyzes the received data using one or more of the techniques described above.

The system 900 includes a processor 910, a memory 920, a storage device 930, and an input/output device 940. Each of the components 910, 920, 930, and 940 can be interconnected, for example, using a system bus 950. The processor 910 is capable of processing instructions for execution within the system 900. In some implementations, the processor 910 is a single-threaded processor. In some implementations, the processor 910 is a multi-threaded processor. In some implementations, the processor 910 includes graphic processing units. The processor 910 is capable of processing instructions stored in the memory 920 or on the storage device 930. The processor 910 may execute operations such as performing one or more of the techniques described above.

The memory 920 stores information within the system 900. In some implementations, the memory 920 is a computer-readable medium. In some implementations, the memory 920 is a volatile memory unit. In some implementations, the memory 920 is a non-volatile memory unit.

The storage device 930 is capable of providing mass storage for the system 900. In some implementations, the storage device 930 is a non-transitory computer-readable medium. In various different implementations, the storage device 930 can include, for example, a hard disk device, an optical disk device, a solid-state drive, a flash drive, magnetic tape, or some other large capacity storage device. In some implementations, the storage device 930 may be a cloud storage device, e.g., a logical storage device including multiple physical storage devices distributed on a network and accessed using a network. In some examples, the storage device may store long-term data. The input/output device 940 provides input/output operations for the system 900. In some implementations, the input/output device 940 can include one or more of a network interface devices, e.g., an Ethernet card, a serial communication device, e.g., an RS-232 port, and/or a wireless interface device, e.g., an 802.11 card, a 3G wireless modem, a 4G wireless modem, etc. A network interface device allows the system 900 to communicate, for example, transmit and receive data. In some implementations, the input/output device can include driver devices configured to receive input data and send output data to other input/output devices, e.g., a keyboard, a mouse, a printer, a sensor (e.g., a sensor that measures component or system-related properties, a sensor that measures environmental-related properties, or other types of sensors), and a display device 960. In some implementations, mobile computing devices, mobile communication devices, and other devices can be used.

A computing system can be realized by instructions that upon execution cause one or more processing devices to carry out the processes and functions described above, for example, storing, maintaining, and displaying artifacts. Such instructions can include, for example, interpreted instructions such as script instructions, or executable code, or other instructions stored in a computer readable medium. A computing system can be distributively implemented over a network, such as a server farm, or a set of widely distributed servers or can be implemented in a single virtual device that includes multiple distributed devices that operate in coordination with one another. For example, one of the devices can control the other devices, or the devices may operate under a set of coordinated rules or protocols, or the devices may be coordinated in another fashion. The coordinated operation of the multiple distributed devices presents the appearance of operating as a single device.

Although an example processing system has been described in FIG. 33, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification, such as performing one or more of the above described processes, can be implemented as one or more computer program products, e.g., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "processing module" may encompass all apparatus, devices, and machines for processing data, including by way of example a programmable processor, a computer, or multiple processors or computers. A processing module can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. Sometimes a server is a general purpose computer, and sometimes it is a custom-tailored special purpose electronic device, and sometimes it is a combination of these things. Implementations can include a back end component, e.g., a data server, or a middleware component, e.g., an application server, or a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

Certain features that are described above in the context of separate implementations can also be implemented in combination in a single implementation. Conversely, features that are described in the context of a single implementation can be implemented in multiple implementations separately or in any sub-combinations.

The order in which operations are performed as described above can be altered. In certain circumstances, multitasking and parallel processing may be advantageous. The separation of system components in the implementations described above should not be understood as requiring such separation.

A number of embodiments of the invention have been described. Nevertheless, it will be understood that various modifications may be made without departing from the spirit and scope of the disclosure. Accordingly, other embodiments are within the scope of the following claims.

For instance, in one example, a method for mapping tissue oxygen extraction fraction (OEF) of an object comprises the acts of receiving magnetic resonance imaging (MRI) signals obtained by a magnetic resonance scanner, wherein the MRI signals comprises multiecho magnitude and phase data;

performing physics modeling of both magnitude and phase data, wherein a combined model of a QSM-based method and qBOLD (QSM+qBOLD) is used to consider an effect of OEF on both magnitude and phase signal from the same underlying gradient echo data using an automated clustering analysis of signal evolution over echo time, wherein a cluster analysis of time evolution method is used to overcome a noise sensitivity of QSM+qBOLD in obtaining model parameters; and presenting, on a display device, one or more images of the object generated based on model parameters including OEF.

In some examples of the aforementioned method, clustering is performed using an x-means method.

In some examples of the aforementioned method(s), wherein the obtaining model parameters is solved using optimization.

In some examples of the aforementioned method(s), wherein the obtaining model parameters is solved using deep learning.

In some examples of the aforementioned method(s), wherein an artificial neural network for deep learning is trained on simulated complex multiecho MRI data.

In some examples of the aforementioned method(s), wherein the object comprises one or more of a cortex, a region of white matter, a region of deep gray matter, a region of ischemia of a brain, or a lesion of diseased tissue.

In another example, a system for mapping tissue oxygen extraction fraction (OEF) of an object, comprises a processor; a graphical output module communicatively coupled to the processor; an input module communicatively coupled to the processor; a non-transitory computer storage medium encoded with a computer program, the program comprising instructions that when executed by processor cause the processor to perform operations comprising: receiving magnetic resonance imaging (MRI) signals obtained by a magnetic resonance scanner, wherein the MRI signals comprises multiecho magnitude and phase data; performing physics modeling of both magnitude and phase data, wherein a combined model of the QSM-based method and qBOLD (QSM+qBOLD) is used to consider the effect of OEF on both magnitude and phase signal from the same underlying gradient echo data; using an automated clustering analysis of signal evolution over echo time, wherein a cluster analysis of time evolution method is used to overcome the noise sensitivity of QSM+qBOLD in obtaining model parameters; and presenting, on a display device, one or more images of the object generated based on model parameters including OEF.

What is claimed is:

1. A system for generating one or more images of an object, the system comprising:
    a processor;
    a display communicatively coupled to the processor;
    an input interface communicatively coupled to the processor;
    a non-transitory computer storage medium encoded with a computer program, the program comprising instructions that when executed by the processor cause the processor to perform operations comprising:
    acquiring time-resolved image data capturing tracer passage in tissue of the object;
    solving an inverse problem of fitting the image data to a transport equation or a concentration—transport relationship that is expressed as a relationship between a concentration of the tracer at a given location and transport parameters at that location, wherein the relationship comprises a temporal change of a local concentration at the given location and a local divergence of mass flux, wherein the mass flux comprises the concentration multiplied by a velocity, and wherein solving the inverse problem comprises:
    estimating a transport distribution of the tissue of the object using prior knowledge about a tissue transport parameter distribution characterized by an artificial neural network or using tissue morphological information having a sparsity characterized velocity distribution; and
    generating one or more images of the object based on the estimated transport distribution of the object; and
    presenting, on a display device, the one or more images of the object generated based on the solving of the inverse problem.

2. The system of claim 1, wherein solving the inverse problem comprises determining a tracer concentration time course from the time-resolved image data.

3. The system of claim 1, wherein solving the inverse problem comprises determining a cost function corresponding to the tissue transport parameter distribution and the tracer concentration.

4. The system of claim 1, wherein the velocity distribution is sparsity characterized by a cost function of an L1 norm of a gradient of a velocity spatial distribution or by the artificial neural network.

5. The system of claim 1, wherein solving the inverse problem comprises using a quasi Newton, alternating direction method of multipliers, or the artificial neural network.

6. The system of claim 1, wherein the image data is acquired using imaging modalities comprising dynamic contrast enhanced (DCE) magnetic resonance imaging (MRI), computed tomography (CT), positron emission tomography (PET), single-photon emission computed tomography (SPECT), or arterial spin labelling data in MRI.

7. A method for generating one or more images of an object, the method comprising:
    acquiring, by a processor of a computing system, time-resolved image data capturing tracer passage in tissue of the object;
    solving, by the processor of the computing system, an inverse problem of fitting the image data to a transport equation or a concentration—transport relationship that is expressed as a relationship between a concentration of the tracer at a given location and transport parameters at that location, wherein the relationship comprises a temporal change of a local concentration at the given location and a local divergence of mass flux, wherein the mass flux comprises the concentration multiplied by a velocity, and wherein solving the inverse problem comprises:
    estimating a transport distribution of the tissue of the object using prior knowledge about a tissue transport parameter distribution characterized by an artificial neural network or using tissue morphological information having a sparsity characterized velocity distribution; and
    generating one or more images relating to the object based on the estimated transport distribution of the object; and
    presenting, on a display device of the computing system, the one or more images of the object generated based on the solving of the inverse problem.

8. The method of claim 7, wherein solving the inverse problem comprises determining a tracer concentration time course from time-resolved imaging data.

9. The method of claim 8, wherein the velocity distribution is sparsity characterized by a cost function of an L1 norm of a gradient of a velocity spatial distribution or by the artificial neural network.

10. The method of claim 8, wherein the image data is acquired using imaging modalities comprising dynamic contrast enhanced (DCE) magnetic resonance imaging (MRI), computed tomography (CT), positron emission tomography (PET), single-photon emission computed tomography (SPECT), or arterial spin labelling data in MRI.

11. The method of claim 7, wherein solving the inverse problem comprising determining a cost function corresponding to the tissue transport parameter distribution and the tracer concentration.

12. The method of claim 11, wherein the velocity distribution is sparsity characterized by a cost function of an L1 norm of a gradient of a velocity spatial distribution or by the artificial neural network.

13. The method of claim 11, wherein the image data is acquired using imaging modalities comprising dynamic contrast enhanced (DCE) magnetic resonance imaging (MRI), computed tomography (CT), positron emission tomography (PET), single-photon emission computed tomography (SPECT), or arterial spin labelling data in MRI.

14. The method of claim 7, wherein the velocity distribution is sparsity characterized by a cost function of an L1 norm of a gradient of a velocity spatial distribution or by the artificial neural network.

15. The method of claim 14, wherein the image data is acquired using imaging modalities comprising dynamic contrast enhanced (DCE) magnetic resonance imaging (MRI), computed tomography (CT), positron emission tomography (PET), single-photon emission computed tomography (SPECT), or arterial spin labelling data in MRI.

16. The method of claim 7, wherein solving the inverse problem comprises using a quasi Newton, alternating direction method of multipliers, or the artificial neural network.

17. The method of claim 16, wherein the image data is acquired using imaging modalities comprising dynamic contrast enhanced (DCE) magnetic resonance imaging (MRI), computed tomography (CT), positron emission tomography (PET), single-photon emission computed tomography (SPECT), or arterial spin labelling data in MRI.

18. The method of claim 7, wherein the image data is acquired using imaging modalities comprising dynamic contrast enhanced (DCE) magnetic resonance imaging (MRI), computed tomography (CT), positron emission tomography (PET), single-photon emission computed tomography (SPECT), or arterial spin labelling data in MRI.

19. A non-transitory computer-readable medium having processor-executable instructions stored thereon for generating one or more images of an object, wherein the processor-executable instructions, when executed, facilitate performance of the following:

acquiring time-resolved image data capturing tracer passage in tissue of the object;

solving an inverse problem of fitting the image data to a transport equation or a concentration—transport relationship that is expressed as a relationship between a concentration of the tracer at a given location and transport parameters at that location, wherein the relationship comprises a temporal change of a local concentration at the given location and a local divergence of mass flux, wherein the mass flux comprises the concentration multiplied by a velocity, and wherein solving the inverse problem comprises:

estimating a transport distribution of the tissue of the object using prior knowledge about a tissue transport parameter distribution characterized by an artificial neural network or using tissue morphological information having a sparsity characterized velocity distribution; and generating one or more images relating to the object based on the estimated transport distribution of the object; and presenting, on a display device, the one or more images of the object generated based on the solving of the inverse problem.

* * * * *